(12) United States Patent
Hobson et al.

(10) Patent No.: US 10,772,970 B2
(45) Date of Patent: Sep. 15, 2020

(54) GLUCOCORTICOID RECEPTOR AGONIST AND IMMUNOCONJUGATES THEREOF

(71) Applicant: AbbVie Inc., North Chicago, IL (US)

(72) Inventors: Adrian Hobson, Shrewsbury, MA (US); Michael McPherson, Ashby, MA (US); Wendy Waegell, Brookfield, MA (US); Christian Goess, Sturbridge, MA (US); Axel Hernandez, Jr., Charlton, MA (US); Lu Wang, Northborough, MA (US); Lu Wang, Westborough, MA (US); Christopher C. Marvin, Grayslake, IL (US); Ling C. Santora, Shrewsbury, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 16/204,825

(22) Filed: Nov. 29, 2018

(65) Prior Publication Data

US 2019/0167804 A1 Jun. 6, 2019

Related U.S. Application Data

(60) Provisional application No. 62/593,776, filed on Dec. 1, 2017, provisional application No. 62/595,054, filed on Dec. 5, 2017.

(51) Int. Cl.
| | |
|---|---|
| *A61K 47/68* | (2017.01) |
| *A61P 19/02* | (2006.01) |
| *A61P 1/00* | (2006.01) |
| *A61K 38/19* | (2006.01) |
| *C07K 16/24* | (2006.01) |

(52) U.S. Cl.
CPC ........ *A61K 47/6803* (2017.08); *A61K 38/191* (2013.01); *A61K 47/6845* (2017.08); *A61K 47/6889* (2017.08); *A61P 1/00* (2018.01); *A61P 19/02* (2018.01); *C07K 16/241* (2013.01); *C07K 16/249* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| | | |
|---|---|---|
| 3,126,375 A | 3/1964 | Ringold et al. |
| 3,886,145 A | 5/1975 | Diamanti |
| 4,588,585 A | 5/1986 | Mark et al. |
| 5,010,176 A | 4/1991 | Barton |
| 5,225,539 A | 7/1993 | Winter |
| 5,545,807 A | 8/1996 | Surani et al. |
| 5,728,826 A | 3/1998 | Gutterer |
| 5,733,901 A | 3/1998 | Gutterer |
| 5,792,758 A | 8/1998 | Tjoeng et al. |
| 5,824,669 A | 10/1998 | Garvey et al. |
| 6,090,382 A | 7/2000 | Salfeld et al. |
| 6,258,562 B1 | 7/2001 | Salfeld et al. |
| 6,579,863 B1 | 6/2003 | Garvey et al. |
| 6,787,533 B1 | 9/2004 | Gutterer |
| 7,012,135 B2 | 3/2006 | Athwal et al. |
| 7,160,920 B2 | 1/2007 | Garvey et al. |
| 7,227,003 B2 | 6/2007 | Le et al. |
| 7,468,433 B2 | 12/2008 | Schmidt |
| 7,524,502 B2 | 4/2009 | Hellendoorn et al. |
| 7,709,226 B2 | 5/2010 | Foote |
| 7,744,885 B2 | 6/2010 | Le et al. |
| 8,158,780 B2 | 4/2012 | Phull et al. |
| 8,232,304 B2 | 7/2012 | Goldstein et al. |
| 8,371,292 B2 | 2/2013 | Bethke et al. |
| 8,501,906 B2 | 8/2013 | McTavish |
| 8,524,697 B2 | 9/2013 | Anthes et al. |
| 8,597,648 B2 | 12/2013 | Guo et al. |
| 8,747,854 B2 | 6/2014 | Okun et al. |
| 8,765,696 B2 | 7/2014 | Ishii |
| 8,822,439 B2 | 9/2014 | Glossop et al. |
| 8,877,194 B2 | 11/2014 | Hsieh et al. |
| 9,101,670 B2 | 8/2015 | Bossard et al. |
| 9,109,005 B2 | 8/2015 | Puder et al. |
| 9,422,327 B2 | 8/2016 | Schmidt |
| 9,428,540 B2 | 8/2016 | Myhren et al. |
| 2002/0022720 A1 | 2/2002 | Le et al. |
| 2003/0130189 A1 | 7/2003 | Senter et al. |
| 2003/0175837 A1 | 9/2003 | Le et al. |
| 2003/0199679 A1 | 10/2003 | Adair et al. |
| 2003/0235585 A1 | 12/2003 | Fischkoff et al. |
| 2004/0156869 A1 | 8/2004 | Bakthavatchalam et al. |
| 2005/0107408 A1 | 5/2005 | Goldstein |
| 2005/0143381 A1 | 6/2005 | Yu et al. |
| 2006/0073141 A1 | 4/2006 | Ignatovich et al. |

(Continued)

FOREIGN PATENT DOCUMENTS

| | | |
|---|---|---|
| CA | 2754589 A1 | 9/2010 |
| DE | 10055820 C1 | 7/2002 |

(Continued)

OTHER PUBLICATIONS

Aggarwal, B.B., "Historical Perspectives on Tumor Necrosis Factor and Its Superfamily: 25 Years Later, a Golden Journey," Blood 119(3):651-665, American Society of Hematology,United States (2012).

(Continued)

*Primary Examiner* — Karl J Puttlitz

(74) *Attorney, Agent, or Firm* — Womble Bond Dickinson (US) LLP; Cristin H. Cowles; Danielle L. Herritt

(57) ABSTRACT

Provided herein are glucocorticoid receptor agonist immunoconjugates, glucocorticoid receptor agonists, and methods of using the same.

6 Claims, 4 Drawing Sheets

Specification includes a Sequence Listing.

(56) References Cited

U.S. PATENT DOCUMENTS

| | | |
|---|---|---|
| 2006/0088523 A1 | 4/2006 | Andya et al. |
| 2006/0093601 A1 | 5/2006 | Fong et al. |
| 2007/0160617 A1 | 7/2007 | Ma et al. |
| 2008/0050310 A1 | 2/2008 | Ebens et al. |
| 2008/0305044 A1 | 12/2008 | McDonagh et al. |
| 2008/0312425 A1 | 12/2008 | Bonnerjea et al. |
| 2009/0227548 A1 | 9/2009 | Glossop et al. |
| 2009/0318396 A1 | 12/2009 | Baker et al. |
| 2010/0028346 A1 | 2/2010 | Lutz et al. |
| 2010/0034773 A1 | 2/2010 | Tran et al. |
| 2010/0056488 A1 | 3/2010 | Teicher et al. |
| 2010/0099654 A1 | 4/2010 | Finn et al. |
| 2010/0120733 A1 | 5/2010 | Gant et al. |
| 2010/0209508 A1 | 8/2010 | Baker et al. |
| 2010/0233079 A1 | 9/2010 | Jakob et al. |
| 2010/0266496 A1 | 10/2010 | Hansen et al. |
| 2010/0331539 A1 | 12/2010 | La Loggia et al. |
| 2011/0097322 A1 | 4/2011 | Alley et al. |
| 2011/0172278 A1 | 7/2011 | He et al. |
| 2011/0250130 A1 | 10/2011 | Benatuil et al. |
| 2011/0262368 A1 | 10/2011 | Anthes et al. |
| 2011/0287009 A1 | 11/2011 | Scheer et al. |
| 2011/0294766 A1 | 12/2011 | Burkamp et al. |
| 2011/0300150 A1 | 12/2011 | Eliasof |
| 2011/0318349 A1 | 12/2011 | Ghayur et al. |
| 2012/0059158 A1 | 3/2012 | Ishii |
| 2013/0017200 A1 | 1/2013 | Scheer et al. |
| 2013/0115269 A1 | 5/2013 | Smith et al. |
| 2013/0164256 A1 | 6/2013 | Hsieh et al. |
| 2014/0161804 A1 | 6/2014 | Cuff et al. |
| 2014/0179650 A1 | 6/2014 | Aven et al. |
| 2014/0200332 A1 | 7/2014 | Kaymakcalan et al. |
| 2014/0294813 A1 | 10/2014 | Ghayur et al. |
| 2015/0158943 A1 | 6/2015 | Robblee et al. |
| 2015/0250896 A1 | 9/2015 | Zhao |
| 2017/0196975 A1 | 7/2017 | Bossard et al. |
| 2018/0126000 A1 | 5/2018 | McPherson et al. |
| 2019/0262465 A1 | 8/2019 | McPherson et al. |

FOREIGN PATENT DOCUMENTS

| | | |
|---|---|---|
| EP | 0315456 A2 | 5/1989 |
| EP | 2641900 A1 | 9/2013 |
| GB | 933867 A | 8/1963 |
| JP | 2749778 B2 | 5/1998 |
| JP | 2016190798 A | 11/2016 |
| JP | 2017066075 A | 4/2017 |
| WO | 9425478 A1 | 11/1994 |
| WO | 9734871 A1 | 9/1997 |
| WO | 9809982 A1 | 3/1998 |
| WO | 0049993 A2 | 8/2000 |
| WO | 01/94585 A1 | 12/2001 |
| WO | 03031464 A2 | 4/2003 |
| WO | 2004/017904 A2 | 3/2004 |
| WO | 2004056847 A2 | 7/2004 |
| WO | 2004066957 A2 | 8/2004 |
| WO | 2005028495 A1 | 3/2005 |
| WO | 2005044759 A2 | 5/2005 |
| WO | 2005063777 A1 | 7/2005 |
| WO | 2005065435 A2 | 7/2005 |
| WO | 2005074924 A1 | 8/2005 |
| WO | 2006019447 A1 | 2/2006 |
| WO | 2006027377 A1 | 3/2006 |
| WO | 2006097458 A1 | 9/2006 |
| WO | 2006108556 A2 | 10/2006 |
| WO | 2006110593 A2 | 10/2006 |
| WO | 2006135479 A2 | 12/2006 |
| WO | 2007054974 A2 | 5/2007 |
| WO | 2007/117685 A2 | 10/2007 |
| WO | 2008015696 A2 | 2/2008 |
| WO | 2008052350 A1 | 5/2008 |
| WO | 2009003199 A1 | 12/2008 |
| WO | 09069032 A2 | 6/2009 |
| WO | 2009095478 A1 | 8/2009 |
| WO | 2010075249 A2 | 7/2010 |
| WO | 2010080538 A1 | 7/2010 |
| WO | 2010126953 A1 | 11/2010 |
| WO | 2010132743 A1 | 11/2010 |
| WO | 2010136940 A1 | 12/2010 |
| WO | 2011039510 A2 | 4/2011 |
| WO | 2011072124 A1 | 6/2011 |
| WO | 2011081937 A1 | 7/2011 |
| WO | 2012040228 A2 | 3/2012 |
| WO | 2012040229 A1 | 3/2012 |
| WO | 2012082947 A1 | 6/2012 |
| WO | 2012089247 A1 | 7/2012 |
| WO | 2012/131053 A1 | 10/2012 |
| WO | 2013087912 A1 | 6/2013 |
| WO | 2013149959 A1 | 10/2013 |
| WO | 2013170761 A1 | 11/2013 |
| WO | 2014058389 A1 | 4/2014 |
| WO | 2014152247 A1 | 9/2014 |
| WO | 2015012904 A2 | 1/2015 |
| WO | 2015047510 A1 | 4/2015 |
| WO | 2015073884 A2 | 5/2015 |
| WO | 2015127685 A1 | 9/2015 |
| WO | 2015151078 A2 | 10/2015 |
| WO | 2015151079 A2 | 10/2015 |
| WO | 2015153401 A1 | 10/2015 |
| WO | 2015155753 A2 | 10/2015 |
| WO | 2016003869 A1 | 1/2016 |
| WO | 2016042163 A2 | 3/2016 |
| WO | 2016120891 A1 | 8/2016 |
| WO | 2017210471 A1 | 12/2017 |
| WO | 2018089373 A2 | 5/2018 |

OTHER PUBLICATIONS

Alley, S.C., et al., "Contribution of Linker Stability to the Activities of Anticancer Immunoconjugates," Bioconjugate Chemistry 19(3):759-765, American Chemical Society, United States (2008).

Alperovich, A. and Younes, A., "Targeting CD30 Using Brentuximab Vedotin in the Treatment of Hodgkin Lymphoma," Cancer Journal 22(1):23-26, Lippincott Williams & Wilkins, United States (2016).

Ashton, et.al., "Anti-inflammatory 17b-Thioalkyl-16a, 17a-ketal and-acetal Androstanes: A New Class of Airway Selective Steroids for the Treatment of Asthma," J.Med.Chem., 39, 25, 4888-4896.

Belvisi, M.G., et al., "Preclinical Profile of Ciclesonide, a Novel Corticosteroid for the Treatment of Asthma," Journal of Pharmacology and Experimental Therapeutics 314(2):568-574, Williams and Wilkins, United States (Aug. 2005).

Berger, W.E., "Ciclesonide: A Novel Inhaled Corticosteroid for the Treatment of Persistent Asthma—A Pharmacologic and Clinical Profile," Therapy 2(2):167-178 (2005).

Bidard F.C. and Tredan, O., "Trends in Cancer-targeted Antibody-drug Conjugates," Targeted Oncology 9(1):1-8, Springer-Verlag France, France (2014).

Bodor, N. and Buchwald, P., Corticosteroid Design for the Treatment of Asthma: Structural Insights and the Therapeutic Pharmaceutical Design 12(25):3241-3260, Bentham Science Publishers, Netherlands (2006).

Boero, S., et al., "Modulation of Human Lung Fibroblast Functions by Ciclesonide: Evidence for Its Conversion Into the Active Metabolite Desisobutyryl-ciclesonide," Immunology Letters 112(1):39-46, Elsevier/North-Holland Biomedical Press, Netherlands (2007).

Bradley, J.R., "TNF-mediated Inflammatory Disease," The Journal of Pathology 214(2):149-160, John Wiley and Sons, England (2008).

Brandish, P.E., et al., "Development of Anti-CD74 Antibody-Drug Conjugates to Target Glucocorticois to Immune Cells," Bioconjugate Chemistry (2018).

Brandt, "Steroid Chemistry and Steroid Hormone Action," Endocrine, pp. 1-18.

Breedveld, F.C., et al., "The Premier Study: A Multicenter, Randomized, Double-blind Clinical Trial of Combination Therapy With Adalimumab Plus Methotrexate Versus Methotrexate Alone or Adalimumab Alone in Patients With Early, Aggressive Rheumatoid Arthritis Who Had Not Had Previous Methotrexate Treatment," Arthritis and Rheumatism 54(1):26-37, Wiley-Blackwell, United States (2006).

(56) References Cited

OTHER PUBLICATIONS

Buchwald, P., "Glucocorticoid Receptor Binding: A Biphasic Dependence on Molecular Size as Revealed by the Bilinear LinBiExp Model ," Steroids 73(2):193-208, Elsevier, United States (2008).
Cardillo, et.al.,"Sacitizimab Govitecan (IMMU-132), an Anti-Trop-2/SN-38 Antibody-Drug Conjugate: Characterization and Efficacy in Pancreatic, Gastric, and other Cancers," Bioconj Chem, 26, 919-931, 2015.
Carter, P., et al., "Humanization of an Anti-p185HER2 Antibody for Human Cancer Therapy," Proceedings of the National Academy of Sciences USA 89(10):4285-4289, National Academy of Sciences, United States (May 1992).
Chiang, M.J., et al., "An Fc Domain Protein-small Molecule Conjugate as an Enhanced Immunomodulator," Journal of the American Chemical Society 136(9):3370-3373, American Chemical Society, United States (2014).
Christie, R.J., et.al., "Stabilization of cysteine-linked antibody drug conjugates with N-aryl maleimids," Journal of Controlled Release, 2015, 660-670, 220, Elsevier B.V.
Dahl, R.., "Ciclesonide for the Treatment of Asthma," Therapeutics and Clinical Risk Management 2(1):25-37, Dove Medical Press, New Zealand (2006).
Deora, et.al, "Transmembranes TNF-dependent Uptake of Anti-TNF Antibodies," mABS, 9:4, 680-695 (2017).
Derendorf, H., "Pharmacokinetic and Pharmacodynamic Properties of Inhaled Ciclesonide," Journal of Clinical Pharmacology 47(6):782-789, Wiley, England (2007).
Domain, E., "Modifications of the Self-Immolative Spacer PABOH in Antibody Drug Conjugates," 42 pages (2014).
Doronina, et.al., "Development of potent monoclonal antibody auristatin conjugates for cancer therapy," Nat. Biotechnol, 21, 7, 778-784, 2003.
Doygan et.al., "2-(Maleimidomethyl)-1,3-Dioxanes (MD): a Serum-Stable Self-hydrolysable Hydrophilic Alternative to Classical Maleimide Conjugation," Scientific Reports 6:1, 30835, 2016.
Drug Bank, Certolizumab Pegol, Accession No. DB08904, Biotech, Accessed at HYPERLINK "http://www.drugbank.ca/drugs/DB08904." \h http://www.drugbank.ca/drugs/DB08904.
Edman K., et al., "Ligand Binding Mechanism in Steroid Receptors: From Conserved Plasticity to Differential Evolutionary Constraints," Structure, Dec. 2015, vol. 23 (12), pp. 2280-2290, Cambridge, Mass : Cell Press.
Elias, D.J., et al., "Phase I Clinical Comparative Study of Monoclonal Antibody KS1/4 and KS1/4-methotrexate Immunconjugate in Patients with Non-small Cell Lung Carcinoma," Cancer Research 50(13):4154-4159, American Association for Cancer Research, United States (1990).
Elkady, E.F. and Fouad, M.A., "Forced Degradation Study to Develop and Validate Stability-indicating RP-LC Method for the Determination of Ciclesonide in Bulk Drug and Metered Dose Inhalers," Talanta 87:222-229, Elsevier, Netherlands (2011).
Endo, N., et al., "Nature of Linkage and Mode of Action of Methotrexate Conjugated With Antitumor Antibodies: Implications for Future Preparation of Conjugates," Cancer Research 48(12):3330-3335, American Association for Cancer Research, United States (1988).
Eran Sella, "The Chemistry Behind Antibody-Drug Conjugation," Baran Lab Group Meeting, pp. 1-14.
Everts, M., et al., "Selective Intracellular Delivery of Dexamethasone into Activated Endothelial Cells Using an E-Selectin-Directed Immunoconjugate," The Journal of Immunology 168(2):883-889, American Association of Immunologists, United States (2002).
Fried, J., et al., "Stereochemistry of Unsymmetrically Substituted 16a,17a-methylenedioxyprogesterones," Hormonal Steroids 2:15-21 (1964).
Fukase, H., "Single Dose Study of Ciclesonide in Healthy Male Volunteers: Phase I Study," Japanese Pharmacology & Therapeutics 34(11):1191-1199 (2006).
Gonzalez, D., et al., "Ciclesonide in the Management of Asthma," Clinical Medicine: Therapeutics 1:1437-1449 (2009).
Govindan, et.al., "Milatuzumab-SN-38 Conjugates for the Treatment of CD74+ Cancers," Mol Cancer Ther., 12(6), 968-978, 2013.
Graversen, J.H. and Moestrup, S.K., "Drug Trafficking into Macrophages via the Endocytotic Receptor CD163," Membranes 5(2):228-252, MDPI Publishing, Switzerland (2015).
Graversen, J.H., et al., "Targeting the Hemoglobin Scavenger Receptor CD163 in Macrophages Highly Increases the Anti-inflammatory Potency of Dexamethasone," Molecular Therapy 20(8):1550-1558, Cell Press, United States (2012).
Hamann, et.al., "Monoclonal antibody-drug conjugates," Expert Opinion on Therapeutic Patents, 15, 9, 1087-1103, 2005.
Hamblett, K.J., et al., "Effects of Drug Loading on the Antitumor Activity of a Monoclonal Antibody Drug Conjugate," Clinical Cancer Research 10(20):7063-7070, American Association for Cancer Research, United States (2004).
Jain, N., et al., "Current ADC Linker Chemistry," Pharmaceutical Research 32(11):3526-3540, Kluwer Academic/Plenum Publishers, United States (2015).
Junutula, et.al., "Rapid identification of reactive cysteine residues for site-specific labeling of antibody Fabs," J., Immunol. Methods, 332, 41-52, 2008.
Junutula, et.al., "Site-specific conjugation of a cytotoxic drug to an antibody improves the therapeutic index," Nat. Biotechnol, 26, 925-935, 2008.
Kern, J.C., et al., "Discovery of Pyrophosphate Diesters as Tunable, Soluble, and Bioorthogonal Linkers for Site-Specific Antibody-Drug Conjugates," Journal of the American Chemical Society 138(4):1430-1445, American Chemical Society, United States (2016).
Kroszczynski, W., et al., "Effective High-pressure Cleavage of Sterically Hindered Steroid Esters," Helvetica Chimica Acta 87(6):1488-1492 (2004).
Kvirkvelia, N., et al., "Human Anti-a3(IV)NC1 Antibody Drug Conjugates Target Glomeruli to Resolve Nephritis," American Journal of Physiology Renal Physiology 309(8):F680-F684, American Physiological Society, United States (2015).
Leal, et.al., "Antibody-drug conjugates: an emerging modality for the treatment of cancer," Ann.N.Y.Acad.Sci., 1321, 41-54, 2014.
Levin, A.D., et al., "Mechanism of Action of Anti-TNF Therapy in Inflammatory Bowel Disease," Journal of Crohn's and Colitis 10(8):989-997, Oxford University Press, England (2016).
Lin, J., et al., "TNFalpha Blockade in Human Diseases: An Overview of Efficacy and Safety," Clinical Immunology 126(1):13-30, Academic Press, United States (2008).
Lyon, R.P., et al., "Self-hydrolyzing Maleimides Improve the Stability and Pharmacological Properties of Antibody-drug Conjugates," Nature Biotechnology 32(10):1059-1065, Nature America Publishing, United States (2014).
Mack, F., et al., "The Next Generation of Antibody Drug Conjugates," Seminars in Oncology 41(5):637-652, W.B. Saunders, United States (2014).
Majumdar, S., et al., "MTX-cIBR Conjugate for Targeting Methotrexate to Leukocytes: Conjugate Stability and in vivo Efficacy in Suppressing Rheumatoid Arthritis," Journal of Pharmaceutical Sciences 101(9):3275-3291, Elsevier, United States (2012).
Mark et al., Proceedings of the National Academy of Sciences, USA 81:5662-5666 (1984).
Mars, U., et al., "Tissue Accumulation Kinetics of Ciclesonide-Active Metabolite and Budesonide in Mice," Basic and Clinical Pharmacology and Toxicology112(6):401-411,Blackwell, England (Jun. 2013).
Mascher, H.J., et al., "Sensitive Simultaneous Determination of Ciclesonide, Ciclesonide-m1-metabolite and Fluticasone Propionate in Human Serum by HPLC-MS/MS with APPI," Journal of Chromatography. B, Analytical Technologies in the Biomedical and Life Sciences 869(12):84-92, Elsevier, Netherlands (2008).
McRae, B.L., et al., "Fc Receptor-mediated Effector Function Contributes to the Therapeutic Response of Anti-TNF Monoclonal Antibodies in a Mouse Model of Inflammatory Bowel Disease," Journal of Crohn's & Colitis 10(1):69-76, Oxford University Press, England (2016).

(56) References Cited

OTHER PUBLICATIONS

Millan, D.S., et al., "Design and Synthesis of Long Acting Inhaled Corticosteroids for the Treatment of Asthma," Bioorganic & Medicinal Chemistry Letters 21(19):5826-5830, Elsevier Science Ltd, England (2011).

Mok, C.C., et al., "Immunogenicity of Anti-TNF Biologic Agents in the Treatment of Rheumatoid Arthritis," Expert Opinion on Biological Therapy 16(2):201-211, Taylor & Francis, England (2016).

Moller, L.N., et al., "Anti-CD163-dexamethasone Protects Against Apoptosis After Ischemia/reperfusion Injuries in the Rat Liver," Annals of Medicine and Surgery 4(4):331-337, Elsevier, England (2015).

Moore, A.R., et al., "Collagen II Antibody-induced Arthritis in Tg1278TNFko Mice: Optimization of a Novel Model to Assess Treatments Targeting Human TNFa in Rheumatoid Arthritis," Journal of Translational Medicine 12(1):285, BioMed Central, England (2014).

Nareshkumar, et.al., "Current ADC Linker Chemistry," Pharm Res, 32:3526-3540, 2015.

Nave, R., et al., "Pharmacokinetics of [14C]ciclesonide After Oral and Intravenous Administration to Healthy Subjects," Clinical Pharmacokinetics 43(7):479-486, ADIS Press, Switzerland (2004).

Nave, R., et al., "Safety, Tolerability, and Exposure of Ciclesonide Nasal Spray in Healthy and Asymptomatic Subjects With Seasonal Allergic Rhinitis," Journal of Clinical Pharmacology 46(4):461-467, Wiley, England (2006).

Neffen, H. and Wingertzahn, M.A., "Ciclesonide, A Hypotonic Intranasal Corticosteroid," Allergy and Asthma Proceedings 31(1):S29-S37, OceanSide Publications, United States (2010).

Nolting, B., "Linker Technologies for Antibody-Drug Conjugates," Methods in Molecular Biology 1045:71-100, Humana Press, United States (2013).

Pace, et.al., "Asparagine Deamidation Dependence on Buffer Type, pH, and Temperature," J. Pharm Sci, 102(6), 1712-1723, 2013.

Panowski, S., et al., "Site-specific Antibody Drug Conjugates for Cancer Therapy," mAbs 6(1):34-45, Taylor & Francis, United States (2014).

Perez, C., et al., "A Nonsecretable Cell Surface Mutant of Tumor Necrosis Factor (TNF) Kills by Cell-to-cell Contact," Cell 63(2):251-258, Cell Press, United States (1990).

Pietersz, G.A., et al., "Specific in Vitro Anti-tumour Activity of Methotrexate-monoclonal Antibody Conjugates Prepared Using Human Serum Albumin as an Intermediary," Immunology and Cell Biology 66(Pt 1):43-49, Nature Publishing Group, England (1988).

Polakis, P., "Antibody Drug Conjugates for Cancer Therapy", Pharmacol Rev, 68, 3-19, 2016.

Ritchie, M., et al., "Implications of Receptor-mediated Endocytosis and Intracellular Trafficking Dynamics in the Development of Antibody Drug Conjugates," mAbs 5(1):13-21, Taylor & Francis, United States (2013).

Rosen, J. and Miner, J.N., "The Search for Safer Glucocorticoid Receptor Ligands," Endocrine Reviews 26(3):452-464, Oxford University Press, United States (2005).

Schacke, H., et al., "Mechanisms Involved in the Side Effects of Glucocorticoids," Pharmacology & Therapeutics 96(1):23-43, Pergamon Press, England (2002).

Shen, B.Q., et al., "Conjugation Site Modulates the in Vivo Stability and Therapeutic Activity of Antibody-Drug Conjugates," Nature Biotechnology 30(2):184-189, Nature America Publishing, United States (2012).

Shin, J.M., et al., "Hyaluronic Acid-methotrexate Conjugate for Targeted Therapy of Rheumatoid Arthritis," Revised Electronic Supplementary Information for Chemical Communications, 13 pages (2014).

Stoeck, M., et al., "In Vitro and In Vivo Anti-Inflammatory Activity of the New Glucocorticoid Ciclesonide," Journal of Pharmacology and Experimental Therapeutics 309(1):249-258, Williams & Wilkins, United States (Apr. 2004).

Storz, U., "Antibody-drug Conjugates: Intellectual Property Considerations," mAbs 7(6):989-1009, Taylor and Francis, United States (2015).

Strop, et.al. "Location Matters: Site of Conjugation Modulates Stability and Pharmacokinetics of Antibody Drug Conjugates," Chemistry & Biology, 20(2), 161-167, 2013.

Tumey, L.N., et al., "Mild Method for Succinimide Hydrolysis on ADSs: Impact on ADC Potency, Stability, Exposure, and Efficacy," Bioconjugate Chemistry 25(10):1871-1880, American Chemical Society, United States (2014).

Umemoto, et.al., "Preparation and In Vitro Cytotoxicity of a Methotrexate-anti-MM46 Monoclonal Antibody Conjugate via an Oligopeptide Spacer," Int. J.Cancer, 43, 677-684, 1989.

Van Der Moot, et.al., "Trastuzumab emtansine in advanced human epidermal growth factor receptors 2-positive breast cancer," Expert Opinion on Biological Therapy, 15, 5, 749-160.

Wang, et.al., "Addition of the keto functional group to the genetic code of *Escherichia coli*", Proc, Nat Acad Sci, 100, 1, 56-61, 2003.

Wei, C., et al., "Where Did the Linker-Payload Go? A Quantitative Investigation on the Destination of the Released Linker-Payload from an Antibody-Drug Conjugate with a Maleimide Linker in Plasma," Analytical Chemistry 88(9):4979-4986, American Chemical Society, United States (2016).

Yao, H., et al., "Methods to Design and Synthesize Antibody-Drug Conjugates (ADCs)," International Journal of Molecular Sciences 17(2):16 pages, MDPI, Switzerland (2016).

Verma, et al., "The cryptophycins as potent payloads for antibody drug conjugates," Bioorganic & Medicinal Chemistry Letters 25(4):864-868 (2015).

Gébleux, et al., "Antibody-drug conjugates: Current status and future perspectives," Pharmacology & Therapeutics 167:48-59 (2016).

Rivkin, "Certolizumab Pegol for the Management of Crohn's Disease in Adults," Clinical Therapeutics 31(6):1158-1176 (2009).

Sau, et al., "Cationic lipid-conjugated dexamethasone as a selective antitumor agent," European Journal of Medicinal Chemistry 83:433-447 (2014).

Patel, et al., "Adalimumab: efficacy and safety in psoriasis and rheumatoid arthritis," Dermatologic Therapy 17:427-431 (2004).

U.S. Appl. No. 16/408,602, US 2019-0262465 A1, allowed.

GLUCOCORTICOID RECEPTOR AGONIST AND IMMUNOCONJUGATES THEREOF

RELATED APPLICATIONS

This application claims priority to U.S. Provisional Application No. 62/593,776, filed Dec. 1, 2017 and U.S. Provisional Application No. 62/595,054, filed Dec. 5, 2017, each of which is incorporated by reference in its entirety.

SEQUENCE LISTING

The instant application contains a Sequence Listing which has been submitted electronically in ASCII format and is hereby incorporated by reference in its entirety. Said ASCII copy, created on Nov. 28, 2018, is named A103017_1490WO_SL.txt and is 14,758 bytes in size.

TECHNICAL FIELD

Tumor Necrosis Factor α (TNFα) plays a central role in the pathophysiology of several human disorders, and anti-TNFα agents have clinically validated therapeutic utility in the treatment of autoimmune and inflammatory disorders, such as rheumatoid arthritis, psoriasis and inflammatory bowel disease. Despite their success in the clinic, anti-TNFα biologics are still limited in the maximal efficacy they can achieve in patients, necessitating the identification and development of more potent and effective therapeutics. Patients treated with anti-TNFα biologics may also develop an immunogenic response to the therapeutic thus limiting its effectiveness. Therefore anti-TNFα therapies with lower immunogenicity and high efficacy would be useful for further controlling disease.

Synthetic glucocorticoid receptor agonists are a potent class of small molecules used in the treatment of inflammatory disorders, but their utility in the chronic treatment of disease is limited due to severe side effects. There is a need to develop therapeutics with enhanced efficacy and longer duration of action compared to anti-TNF antibodies and with minimal unwanted effects.

SUMMARY

The present disclosure provides glucocorticoid receptor agonist immunoconjugates useful for treating autoimmune diseases.

In one aspect, the present disclosure provides an antibody drug conjugate comprising:
(a) an anti-TNFα antibody comprising a heavy chain set forth as SEQ ID NO: 3 and a light chain set forth as SEQ ID NO: 4; and (b) a glucocorticoid receptor agonist comprising a radical represented by the formula:

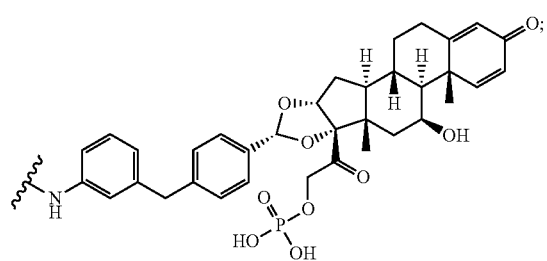

and wherein the antibody is conjugated to the glucocorticoid receptor agonist via a linker represented by the formula:

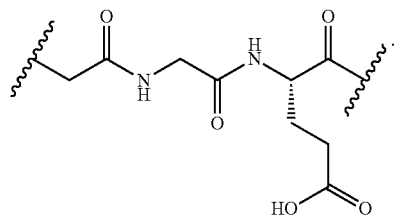 [SMILES: *CC(=O)NCC(=O)N[C@@H](CCC(=O)O)C(*)=O]

In one embodiment, the present disclosure provides an antibody drug conjugate according to the formula:

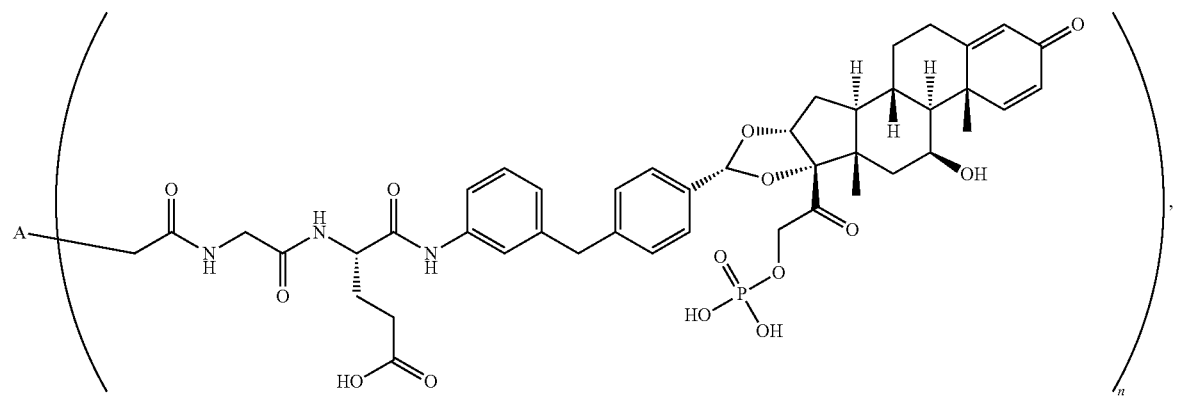

wherein A is the antibody and n is an integer from 1-10.

In one aspect, the present disclosure provides an antibody drug conjugate comprising: (a) an anti-TNFα antibody comprising a heavy chain set forth as SEQ ID NO: 3 and a light chain set forth as SEQ ID NO: 4; and (b) a glucocorticoid receptor agonist comprising a radical represented by the formula:

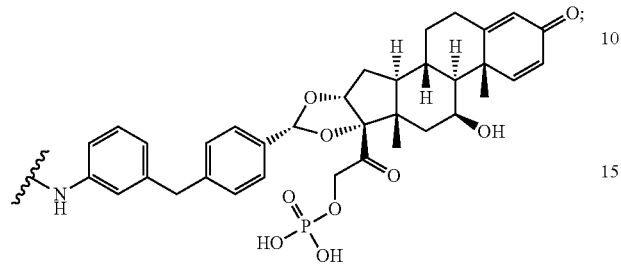

and wherein the antibody is conjugated to the glucocorticoid receptor agonist via a linker represented by the formula:

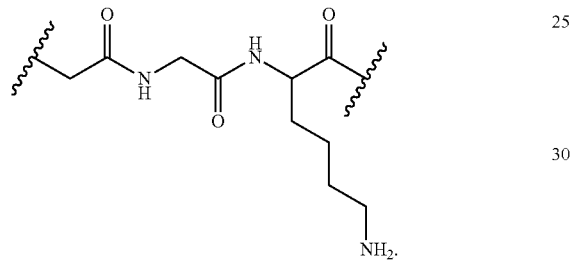

In one embodiment, the present disclosure provides an antibody drug conjugate according to the formula:

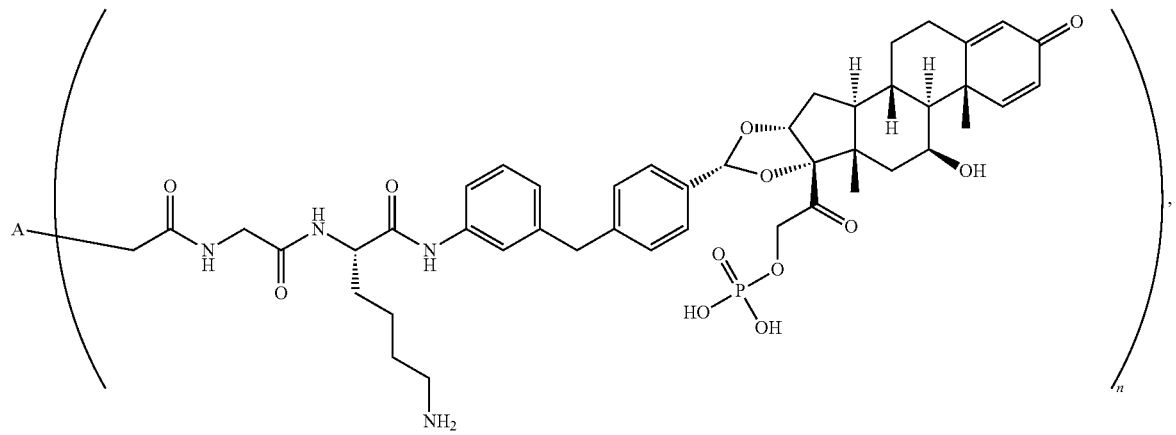

wherein A is the antibody and n is an integer from 1-10.

In one embodiment, the present disclosure provides the antibody drug conjugate of any preceding embodiment, wherein the drug loading is 1, 2, 3, 4, 5, 6, 7, 8, 9, or 10. In one embodiment, the present disclosure provides the antibody drug conjugate of any preceding embodiment, wherein the drug loading is 4, for example, n in the foregoing antibody drug conjugate formula equals 4. In one embodiment, the present disclosure provides the antibody drug conjugate of any preceding embodiment, wherein the drug loading is 2, for example, n in the foregoing antibody drug conjugate formula equals 2.

In one embodiment, the present disclosure provides a method of making the antibody drug conjugate of any preceding embodiment, comprising the step of conjugating the antibody to the glucocorticoid receptor agonist. In one embodiment, the present disclosure provides the method of the preceding embodiment, further comprising the step of introducing a PO₄ moiety on the glucocorticoid receptor agonist before conjugating the antibody to the glucocorticoid receptor agonist. In one embodiment, the present disclosure provides the method of any preceding embodiment, wherein the conjugating comprises partially reducing the antibody, and alkylating the partially reduced antibody with a compound according to the formula:

In one embodiment, the present disclosure provides a pharmaceutical composition comprising the antibody drug conjugate of any preceding embodiment and a pharmaceutically acceptable carrier. In one embodiment, the present disclosure provides the pharmaceutical composition of any of the preceding embodiments, comprising a drug to antibody ratio (DAR) of 1-10.

In one preferred embodiment, the present disclosure provides an antibody drug conjugate according to the formula:

wherein A is adalimumab and n is 4.

In one preferred embodiment, the present disclosure provides an antibody drug conjugate according to the formula:

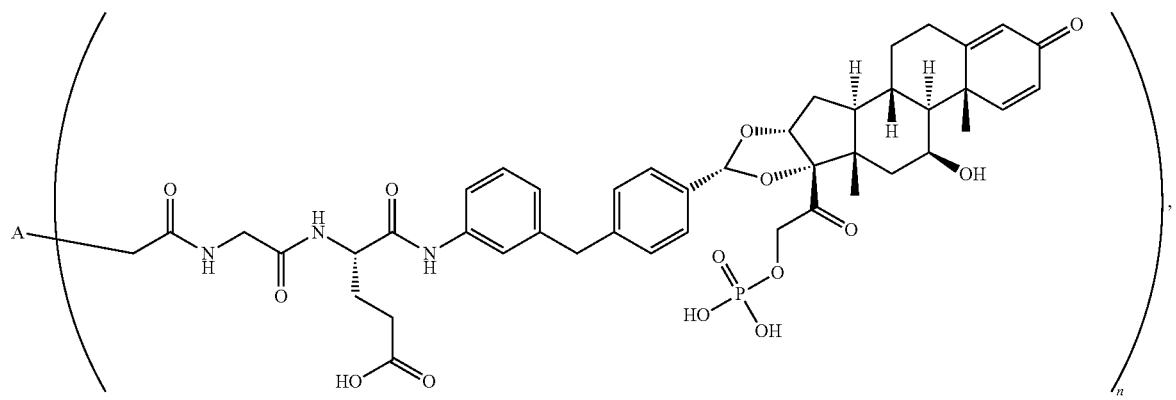

wherein A is an anti-TNFα antibody comprising a heavy chain set forth as SEQ ID NO: 3 and a light chain set forth as SEQ ID NO: 4, and n is 4.

In another preferred embodiment, the present disclosure provides an antibody drug conjugate according to the formula:

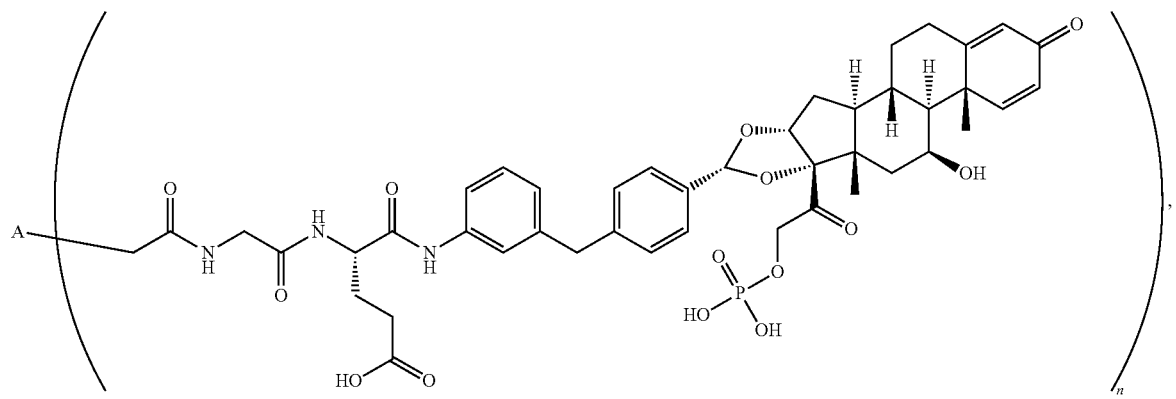

wherein A is adalimumab and n is 2. In another preferred embodiment, the present disclosure provides an antibody drug conjugate according to the formula:

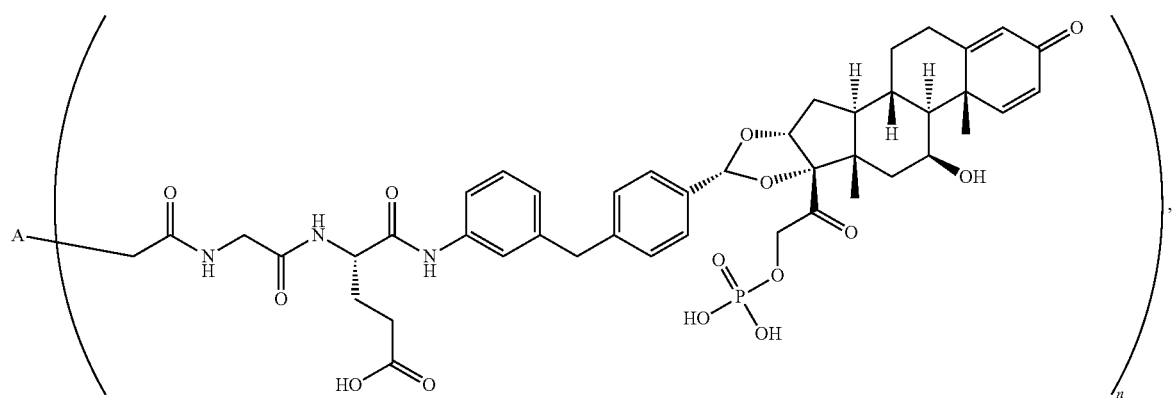

wherein A is an anti-TNFα antibody comprising a heavy chain set forth as SEQ ID NO: 3 and a light chain set forth as SEQ ID NO: 4, and n is 2.

In one preferred embodiment, the present disclosure provides the pharmaceutical composition of any preceding embodiment, comprising a drug to antibody ratio (DAR) of 2.0.

In one preferred embodiment, the present disclosure provides the pharmaceutical composition of any preceding embodiment, comprising a drug to antibody ratio (DAR) of 4.0.

In one embodiment, the present disclosure provides a method of treating a condition selected from rheumatoid arthritis, ankylosing spondylitis, psoriatic arthritis, plaque psoriasis, ulcerative colitis, adult Crohn's disease, pediatric Crohn's disease, uveitis, hidradenitis suppurativa, and juvenile idiopathic arthritis in a subject, comprising administering an effective amount of the antibody drug conjugate of any preceding embodiment or the pharmaceutical composition of any preceding embodiment to the subject.

In one embodiment, the present disclosure provides the antibody drug conjugate of any preceding embodiment or the pharmaceutical composition of any preceding embodiment for use in the treatment of a condition selected from rheumatoid arthritis, ankylosing spondylitis, psoriatic arthritis, plaque psoriasis, ulcerative colitis, adult Crohn's disease, pediatric Crohn's disease, uveitis, hidradenitis suppurativa, and juvenile idiopathic arthritis.

In one embodiment, the present disclosure provides use of the antibody drug conjugate of any preceding embodiment or the pharmaceutical composition of any preceding embodiment for preparation of a medicament for treating a condition selected from rheumatoid arthritis, ankylosing spondylitis, psoriatic arthritis, plaque psoriasis, ulcerative colitis, adult Crohn's disease, pediatric Crohn's disease, uveitis, hidradenitis suppurativa, and juvenile idiopathic arthritis.

In one embodiment, the present disclosure provides a kit comprising: (a) a container comprising the antibody drug conjugate of any preceding embodiment or the pharmaceutical composition of any preceding embodiment; and (b) a label or package insert on or associated with the one or more containers, wherein the label or package insert indicates that the antibody drug conjugate or pharmaceutical composition is used for treating a condition selected from rheumatoid arthritis, ankylosing spondylitis, psoriatic arthritis, plaque psoriasis, ulcerative colitis, adult Crohn's disease, pediatric Crohn's disease, uveitis, hidradenitis suppurativa, and juvenile idiopathic arthritis.

In one embodiment, the present disclosure provides a method of delivering a glucocorticoid receptor agonist to a TNFα-expressing cell, comprising the step of contacting the cell with the antibody drug conjugate of any preceding embodiment. In one embodiment, the present disclosure provides a method of determining anti-inflammatory activity of an antibody drug conjugate comprising: (a) contacting a TNFα-expressing cell with the antibody drug conjugate of any preceding embodiment; and (b) determining release of pro-inflammatory cytokines from the cell as compared to a control cell.

DETAILED DESCRIPTION

Figure 1:
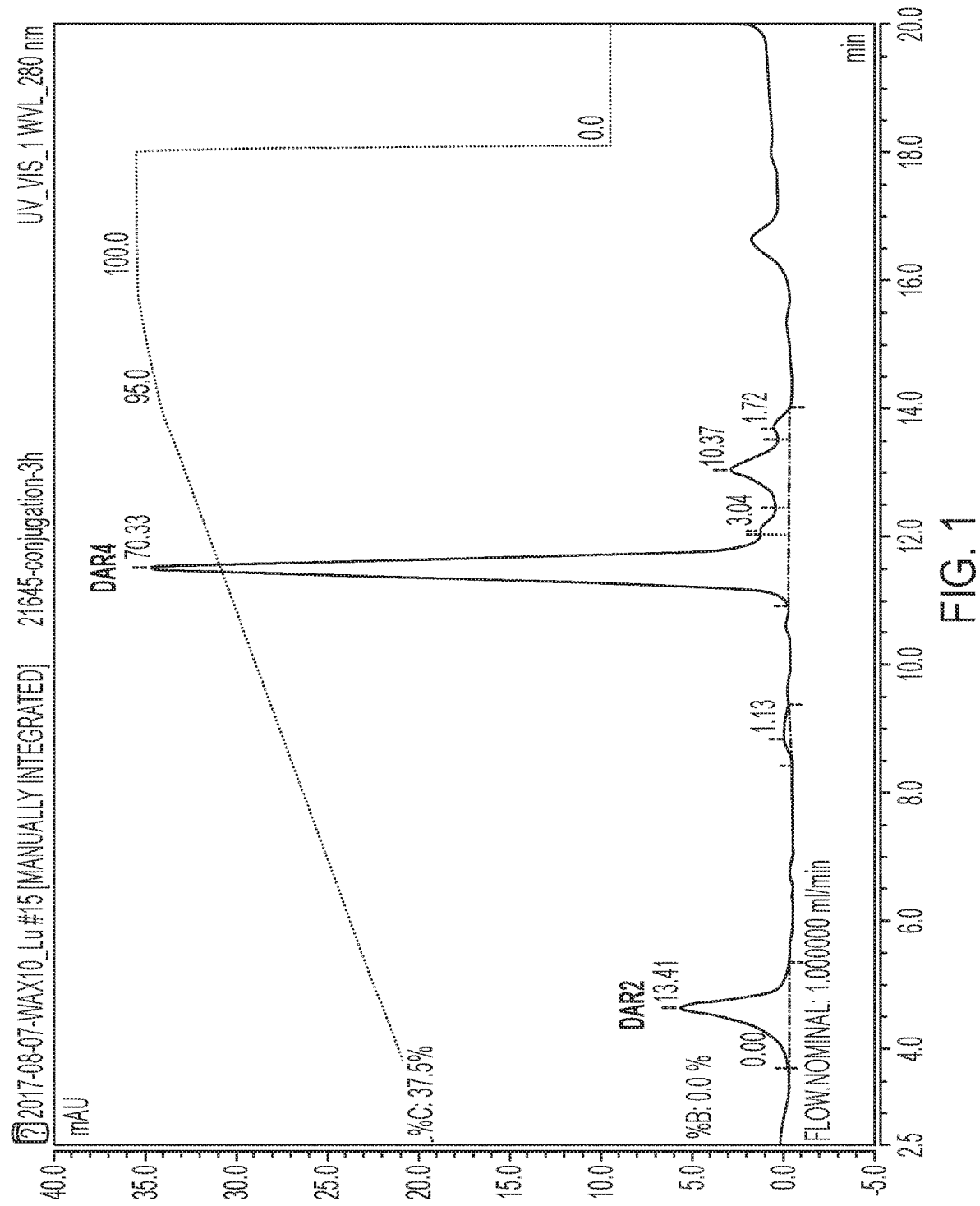
FIG. 1 provides a chromatographic resolution of BrAc-Gly-Glu-glucocorticoid receptor modulator (GRM)-PO$_4$, as performed and described in Example 7. As shown, the ADC is a heterogeneous ADC mixture containing ADCs with two drug linker molecules attached, and ADCs with four drug linker molecules attached.

Provided herein are glucocorticoid receptor agonist immunoconjugates, glucocorticoid receptor agonists, and methods of making and using the same.

Provided herein is an antibody drug conjugate according to the formula:

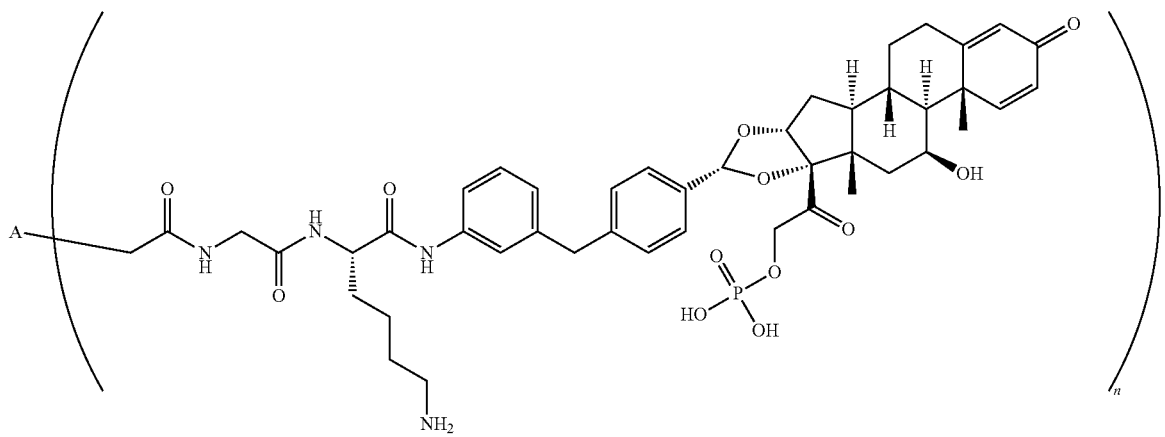

wherein A is adalumimab and n is 4. As demonstrated in Example 7 below, this ADC (i.e., ADC4 below) demonstrates in vitro activity, stability in plasma, and minimal aggregation.

Also provided are methods of making and methods of using ADC4.

I. Definitions

To facilitate an understanding of the present disclosure, a number of terms and phrases are defined below.

The term "anti-TNFα protein" refers to proteins that are capable of (i) binding to TNFα and (ii) inhibiting binding of soluble TNFα to cell surface TNF receptors (p55 and/or p75) and/or lysing surface TNFα or TNFα receptor expressing cells in vitro in the presence of complement. In some embodiments, the anti-TNF antibody, can bind to TNF alpha on the surface of a cell and become internalized. For example, US 2014/0294813, which is herein incorporated by reference in its entirety, discloses anti-TNF antibodies that exhibit cellular internalization upon binding to cell surface human TNF. Anti-TNFα proteins include, for example, anti-TNFα antibodies (e.g., adalimumab, infliximab, and golimumab). Anti-TNFα antibodies are actively internalized upon binding to transmembrane TNF on monocyte-derived DCs and rapidly enter the lysosomes where they are degraded. (Deora et.al. MABS, 2017, Vol. 9, No. 4, 680-694).

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "anti-TNFα antibody" or "an antibody that binds to TNFα" refers to an antibody that is capable of binding TNFα, e.g., with sufficient affinity such that the antibody is useful as a therapeutic agent in targeting TNFα. The extent of binding of an anti-TNFα antibody to an unrelated, non-TNFα protein can be less than about 10% of the binding of the antibody to TNFα as measured, e.g., by a radioimmunoassay (RIA). In certain embodiments, an antibody that binds to TNFα has a dissociation constant (Kd) of ≤1 μM, ≤100 nM, ≤10 nM, ≤1 nM, or ≤0.1 nM.

The term "immunoconjugate," "conjugate," "antibody-drug conjugate," or "ADC" as used herein refers to a compound or a derivative thereof that is conjugated to a protein such as a cell binding agent (e.g., an anti-TNFα antibody) Such immunoconjugates can be defined by a generic formula: $(SM-L-Q)_n$-A, wherein SM=radical derived from a small-molecule glucocorticoid receptor agonist, e.g., a glucocorticosteroid, L=linker, Q=heterobifunctional group or is absent, and A=a protein (e.g., an antibody), and n=1-10. Immunoconjugates can also be defined by the generic formula in reverse order: A-$(Q-L-SM)_n$.

In the present disclosure, the term "linker" refers to a chemical moiety capable of linking the anti-TNFα protein (e.g antibody) to a glucocorticosteroid. Linkers may be susceptible to cleavage (a "cleavable linker") thereby facilitating release of the glucocorticosteroid. For example, such cleavable linkers may be susceptible to peptidase-induced cleavage, at conditions under which the glucocorticosteroid and/or the antibody remains active.

In particular, the cleavable linker component disclosed herein comprises a peptide comprising two to three amino acid residues (a dipeptide or tripeptide) and specifically to dipeptides and tripeptides selected from the group consisting of alanine-alanine (Ala-Ala), glycine-glutamic acid (Gly-Glu), glutamic acid-alanine-alanine (Glu-Ala-Ala), and glycine-lysine (Gly-Lys). The peptide allows for cleavage of the linker by a protease, thereby facilitating release of the glucocorticosteroid upon exposure to intracellular proteases, such as lysosomal enzymes (Doronina et al. (2003) Nat. Biotechnol. 21:778-784).

In the present disclosure, the term "glucocorticosteroid" refers to a naturally-occurring or synthetic steroid hormone that interacts with glucocorticoid receptors, and specific glucocorticosteroids are disclosed in detail herein. A "radical of a glucocorticosteroid" is derived by the removal of one or more hydrogen atoms from a parent glucocorticosteroid. The removal of hydrogen atom(s) facilitates the attachment of the parent glucocorticosteroid to a linker. In the present disclosure, the hydrogen atom is removed from any suitable $-NH_2$ group of the parent glucocorticosteroid. In particular, the "radical of a glucocorticosteroid" is a monovalent radical derived from the removal of one hydrogen atom from a parent glucocorticosteroid.

In the present disclosure, the term "heterobifunctional group" refers to a chemical moiety that connects the linker and the anti-TNFα protein (e.g antibody). Heterobifunctional groups are characterized as having different reactive groups at either end of the chemical moiety.

The term "drug antibody ratio" or "DAR" refers to the number of SMs (e.g., radical derived from a small-molecule glucocorticoid receptor agonist, e.g., a glucocorticosteroid) linked to A (e.g., an antibody). Thus, in the immunoconjugate having the generic formula $(SM-L-Q)_n$-A, the DAR is defined by drug loading per antibody drug conjugate, for example, "n".

When referring to a compound having formula $(SM-L-Q)_n$-A representing an individual immunoconjugate, the term "compound DAR" refers to the number of SMs linked to the individual A (e.g., drug loading or n as an integer of 1 to 10).

When referring to a compound having formula $(SM-L-Q)_n$-A representing a population of immunoconjugates, the term "population DAR" refers to the average number of SMs linked to the As (e.g., drug loading or n as an integer or fraction of 1 to 10±0.5, ±0.4, ±0.3, ±0.2, ±0.1).

The term "subject" refers to humans, non-human primates, and the like, which is to be the recipient of a particular treatment. Typically, the terms "subject" and "patient" are used interchangeably herein in reference to a human subject.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an immunoconjugate as disclosed herein is an amount sufficient to carry out a specifically stated purpose. An "effective amount" can be determined in relation to the stated purpose.

The term "therapeutically effective amount" refers to an amount of an immunoconjugate effective to "treat" a disease or disorder in a subject or mammal A "prophylactically effective amount" refers to an amount effective to achieve the desired prophylactic result.

Terms such as "treating" or "treatment" or "to treat" or "alleviating" or "to alleviate" refer to therapeutic measures that cure, slow down, lessen one or more symptoms of, and/or slow or halt progression of a diagnosed pathologic condition or disorder ("therapeutic treatment"). Thus, those in need of therapeutic treatment include those already diagnosed with or suspected of having the disorder. Prophylactic or preventative measures refer to measures that prevent the development of a targeted pathological condition or disorder ("prophylactic treatment"). Thus, those in need of prophylactic treatment include those prone to have the disorder and those in whom the disorder is to be prevented.

II. Proteins for Linkage to Glucocorticoid Receptor Agonists

The present disclosure provides immunoconjugates containing glucocorticoid receptor agonists linked to proteins, for example, antibodies. In some embodiments, the antibody is human, humanized, chimeric, or murine. In some embodiments, the protein, e.g., antibody, can bind to a target on the surface of a cell and become internalized.

The present disclosure also provides immunoconjugates containing glucocorticoid receptor agonists linked to anti-TNFα proteins. In certain embodiments, the anti-TNFα proteins are antibodies. In certain embodiments, the anti-TNFα proteins are antibodies that bind to TNFα (e.g., soluble TNFα and/or membrane bound TNFα). In certain embodiments, the anti-TNFα proteins are soluble TNF receptor proteins, e.g., soluble TNF receptor proteins fused to a heavy chain constant. In some embodiments, the anti-TNFα protein, e.g., anti-TNFα antibody, binds to TNFα on the surface of a cell and become internalized. For example, US patent application publication no. 2014/0294813, incorporated herein by reference, discloses anti-TNFα proteins that exhibit cellular internalization upon binding to cell surface human TNFα.

In certain embodiments, the antibodies bind to human and/or mouse TNFα.

The full-length amino acid sequence for membrane bound human TNFα is:

MSTESMIRDVELAEEALPKKTGGPQGSRRCL-
FLSLFSFLIVAGATTLFCLLHFGVIGPQRE
EFPRDLSLISPLAQAVRSSSRTPSDKPVAHVVAN-
PQAEGQLQWLNRRANALLANGVELRDNQLVVPS
EGLYLIYSQVLFKGQGCPSTHVLLTHTISRIAVSYQT-
KVNLLSAIKSPCQRETPEGAEAKPWYEPIYLG
GVFQLEKGDRLSAEINRPDYLDFAESGQVYFGIIAL
(SEQ ID NO:1). Soluble human TNFα contains amino acids 77-233 of SEQ ID NO:1. The full-length amino acid sequence for membrane bound murine TNFα is:
MSTESMIRDVELAEEALPQKMGGFQNSRRCL-
CLSLFSFLLVAGATTLFCLLNFGVIGPQRDEKFPNGL
PLISSMAQTLTLRSSSQNSSDKPVAHVVANHQVE-
EQLEWLSQRANALLANGMDLKDNQLVVPADG LYL-
VYSQVLFKGQGCPDYVLLTHTVSRFAISYQEKVNLL-
SAVKSPCPKDTPEGAELKPWYEPIYLGG
VFQLEKGDQLSAEVNLPKYLDFAESGQVYFGVIAL
(SEQ ID NO:2). Soluble murine TNFα contains amino acids 80-235 of SEQ ID NO:2.

In some embodiments, the anti-TNFα antibody binds to human TNFα.

In some embodiments, the anti-TNFα antibody binds to murine TNFα.

In certain embodiments, the anti-TNFα antibody has one or more of the following effects: neutralizes human TNFα cytotoxicity in an in vitro L929 assay with an IC50 of $1\times10^{-7}$ M or less; blocks the interaction of TNFα with p55 and p75 cell surface receptors; and/or lyses surface TNF expressing cells in vitro in the presence of complement.

In certain embodiments, the anti-TNFα antibody does not bind to TNF-beta.

Anti-TNFα antibodies include, for example, adalimumab, which is a recombinant human antibody Amino acid sequences corresponding to the CDR and variable regions of adalimumab are described in U.S. Pat. No. 6,258,562 in reference to antibody D2E7, i.e., SEQ ID Nos: 1 to 8.

The international nonproprietary name (INN) adalimumab is provided in the WHO INN listing site: Year 2000, List 44 (*WHO Drug Information* (2000) Vol. 14(3)).

In certain embodiments, an anti-TNFα antibody comprises sequences of adalimumab, e.g., the complementarity-determining regions (CDRs), the variable heavy domain (VH), and/or the variable light domain (VL). Exemplary sequences are provided in Table 1.

TABLE 1

Exemplary adalimumab antibody region sequences

| Antibody Region | Amino Acid Sequence |
|---|---|
| Heavy chain | EVQLVESGGGLVQPGRSLRLSCAASGFTFDDYAMHWVRQAPGKG<br>LEWVSAITWNSGHIDYADSVEGRFTISRDNAKNSLYLQMNSLRAE<br>DTAVYYCAKVSYLSTASSLDYWGQGTLVTVSSASTKGPSVFPLAP<br>SSKSTSGGTAALGCLVKDYFPEPVTVSWNSGALTSGVHTFPAVLQS<br>SGLYSLSSVVTVPSSSLGTQTYICNVNHKPSNTKVDKKVEPKSCDK<br>THTCPPCPAPELLGGPSVFLFPPKPKDTLMISRTPEVTCVVVDVSHE<br>DPEVKFNWYVDGVEVHNAKTKPREEQYNSTYRVVSVLTVLHQD<br>WLNGKEYKCKVSNKALPAPIEKTISKAKGQPREPQVYTLPPSRDEL<br>TKNQVSLTCLVKGFYPSDIAVEWESNGQPENNYKTTPPVLDSDGSF<br>FLYSKLTVDKSRWQQGNVFSCSVMHEALHNHYTQKSLSLSPGK<br>(SEQ ID NO: 3) |
| Light chain | DIQMTQSPSSLSASVGDRVTITCRASQGIRNYLAWYQQKPGKAPKL<br>LIYAASTLQSGVPSRFSGSGSGTDFTLTISSLQPEDVATYYCQRYNR<br>APYTFGQGTKVEIKRTVAAPSVFIFPPSDEQLKSGTASVVCLLNNFY<br>PREAKVQWKVDNALQSGNSQESVTEQDSKDSTYSLSSTLTLSKAD<br>YEKHKVYACEVTHQGLSSPVTKSFNRGEC (SEQ ID NO: 4) |

TABLE 1-continued

Exemplary adalimumab antibody region sequences

| Antibody Region | Amino Acid Sequence |
| --- | --- |
| Heavy chain variable region | EVQLVESGGGLVQPGRSLRLSCAASGFTFDDYAMHWVRQAPGKG LEWVSAITWNSGHIDYADSVEGRFTISRDNAKNSLYLQMNSLRAE DTAVYYCAKVSYLSTASSLDYWGQGTLVTVSS (SEQ ID NO: 5) |
| Light chain variable region | DIQMTQSPSSLSASVGDRVTITCRASQGIRNYLAWYQQKPGKAPKL LIYAASTLQSGVPSRFSGSGSGTDFTLTISSLQPEDVATYYCQRYNR APYTFGQGTKVEIK (SEQ ID NO: 6) |
| VH-CDR1 | DYAMH (SEQ ID NO: 7) or GFTFDDYAMH (SEQ ID NO: 8) |
| VH-CDR2 | AITWNSGHIDYADSVEG (SEQ ID NO: 9) |
| VH-CDR3 | VSYLSTASS (SEQ ID NO: 10) or VSYLSTASSLDY (SEQ ID NO: 11) |
| VL-CDR1 | RASQGIRNYLA (SEQ ID NO: 12) |
| VL-CDR2 | AASTLQS (SEQ ID NO: 13) |
| VL-CDR3 | QRYNRAPYT (SEQ ID NO: 14) |

In certain embodiments, the anti-TNFα antibody comprises the CDRs of SEQ ID NOs: 3 and 4. In some embodiments, the CDRs comprise SEQ ID NOs: 7 or 8, 9, 10 or 11, 12, 13, and 14. In certain embodiments, the anti-TNFα antibody comprises the heavy chain of SEQ ID NO:3 and/or the light chain of SEQ ID NO:4.

The present disclosure further embraces variants and equivalents which are substantially homologous to anti-TNFα antibodies set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The isolated anti-TNFα antibodies described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., Proc. Nat'l. Acad. Sci. USA 81:5662-5066 (1984) and U.S. Pat. No. 4,588,585.

In some embodiments a DNA sequence encoding an antibody of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest.

In certain embodiments, recombinant expression vectors are used to amplify and express DNA encoding anti-TNFα antibodies. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from Escherichia coli, including pCR 1, pBR322, pMB9 and their derivatives, wider host range plasmids, such as M13 and filamentous single-stranded DNA phages.

Suitable host cells for expression of anti-TNFα antibodies) include prokaryotes, yeast, insect or higher eukaryotic cells under the control of appropriate promoters. Prokaryotes include gram negative or gram positive organisms, for example E. coli or bacilli. Higher eukaryotic cells include established cell lines of mammalian origin. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985). Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823.

III. Immunoconjugates Containing Glucocorticoid Receptor Agonists

Immunoconjugates containing glucocorticoid receptor agonists are also provided. In some embodiments, an immunoconjugate binds to Fc gamma receptor. In some embodiments, an immunoconjugate is active in the GRE transmembrane TNFα reporter assay (as used herein the "GRE transmembrane TNFα reporter assay" refers to the assay used below Example 7 below). In some embodiments, an immunoconjugate shows reduced immunogenicity (reduced anti-drug immune response (ADA)) as compared to the protein in the immunoconjugate (e.g., the antibody) alone.

In one embodiment, disclosed herein is a compound having Formula I-a:

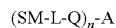  I-a, wherein:

A is an anti-tumor necrosis factor (TNF) α antibody, an anti-TNFα monoclonal antibody, or adalimumab;

L is a linker;
Q is a heterobifunctional group; or
Q is absent;
n is 1-10; and
SM is a monovalent radical of a glucocorticosteroid having any one of:
(1) Formula II-a
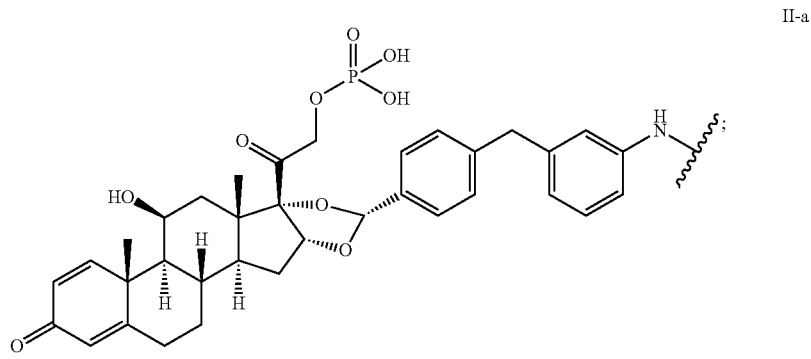
II-a
(2) Formula II-b
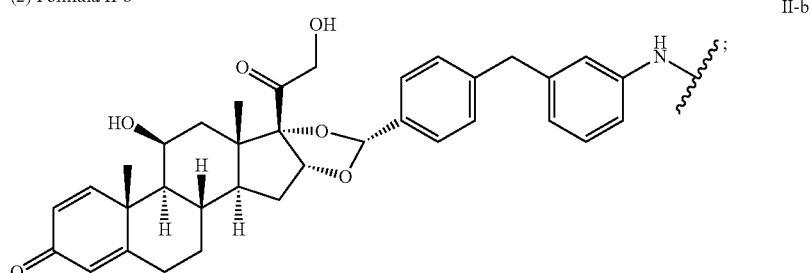
II-b
(3) Formula II-c
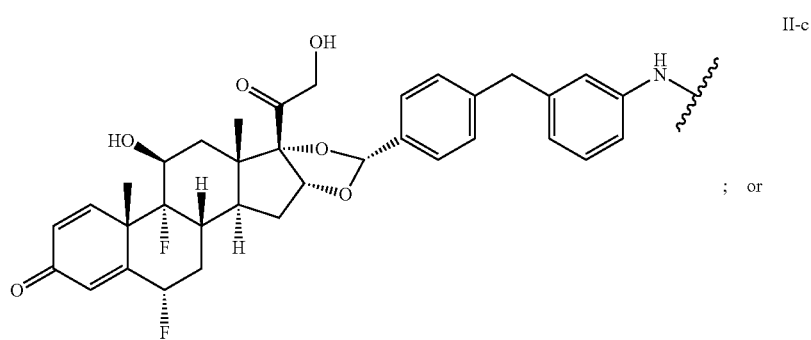
II-c
; or
(4) Formula II-d
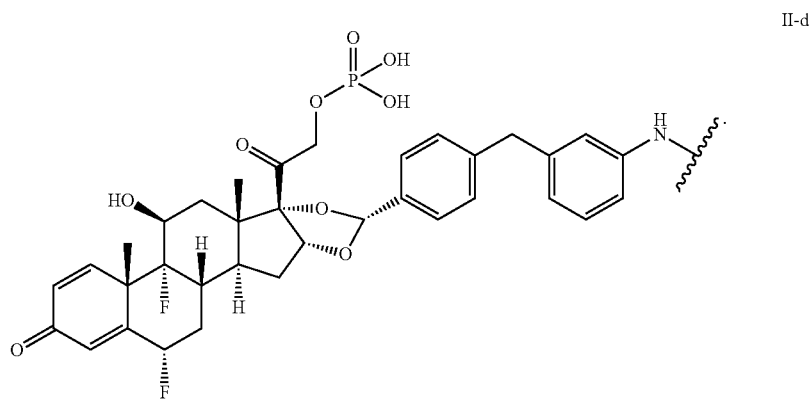
II-d In another embodiment, disclosed herein is a compound having Formula I-a, wherein SM is a monovalent radical of a glucocorticosteroid having any one of Formulae II-a, II-b, II-c, or II-d, wherein L is a cleavable linker comprising a dipeptide or tripeptide, Q is a heterobifunctional group or Q is absent and n is 1-10. In particular, L comprises a dipeptide or tripeptide selected from the group consisting of alanine-alanine (Ala-Ala), glycine-glutamic acid (Gly-Glu), glutamic acid-alanine-alanine (Glu-Ala-Ala), and glycine-lysine (Gly-Lys).

In another embodiment, disclosed herein is a compound having Formula I-a, wherein SM is a monovalent radical of a glucocorticosteroid having any one of Formulae II-a, II-b, II-c, and II-d, wherein Q is a heterobifunctional group represented by:

Q-1

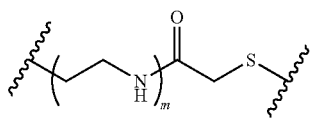

wherein m is 0 or 1.

In another embodiment, m is 0, and Q is represented by:

Q-1a

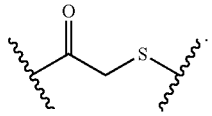

In another embodiment, m is 1, and Q is represented by:

Q-1b

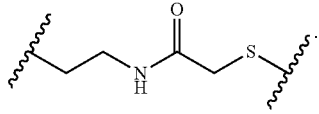

In another embodiment, disclosed herein is a compound having Formula I-a, wherein SM is a monovalent radical of a glucocorticosteroid having any one of Formulae II-a, II-b, II-c, and II-d, wherein -L-Q- is any one of the chemical structures of Table 2:

TABLE 2

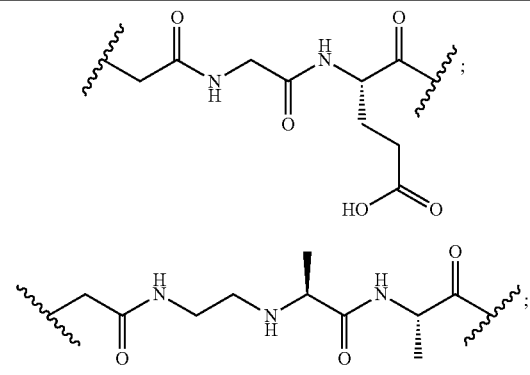

TABLE 2-continued

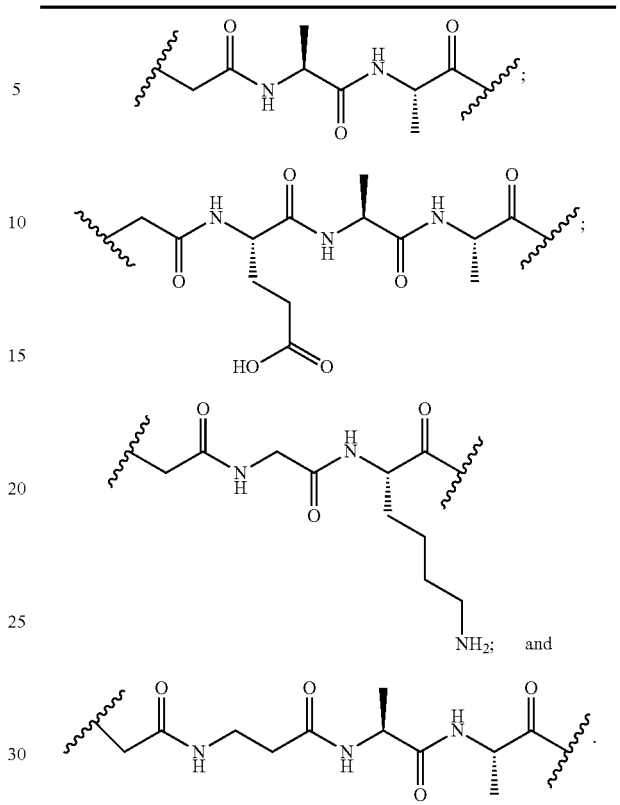

In another embodiment, disclosed herein is a compound having Formula I-a, e.g., a compound having Formula I-a wherein SM is a monovalent radical of a glucocorticosteroid having any one of Formulae II-a, II-b, II-c, and II-d, wherein n is 2-8. In another embodiment, n is 1-5. In another embodiment, n is 2-5. In another embodiment, n is 1. In another embodiment, n is 2. In another embodiment n is 3. In another embodiment, n is 4. In another embodiment, n is 5. In another embodiment, n is 6. In another embodiment, n is 7. In another embodiment, n is 8.

In another embodiment, disclosed herein is a compound having Formula I-a, e.g., a compound having Formula I-a, wherein SM is a monovalent radical of a glucocorticosteroid having any one of Formulae II-a, II-b, II-c, and II-d, wherein A is an antibody.

In another embodiment, disclosed herein is a compound having Formula I-a, e.g., a compound having Formula I-a, wherein SM is a monovalent radical of a glucocorticosteroid having any one of Formulae II-a, II-b, II-c, and II-d, wherein the antibody is murine, chimeric, humanized, or human In another embodiment, disclosed herein is a compound having Formula I-a, e.g., a compound having Formula I-a, wherein SM is a monovalent radical of a glucocorticosteroid having any one of Formulae II-a, II-b, II-c, and II-d, wherein A competitively inhibits binding of an antibody selected from the group consisting of adalimumab, infliximab, certolizumab pegol, and golimumab to TNFα.

In another embodiment, disclosed herein is a compound having Formula I-a, e.g., a compound having Formula I-a, wherein SM is a monovalent radical of a glucocorticosteroid having any one of Formulae II-a, II-b, II-c, and II-d, wherein A binds to the same TNFα epitope as an antibody selected from the group consisting of adalimumab, infliximab, certolizumab pegol, afelimomab, nerelimomab, ozoralizumab, placulumab, and golimumab.

In another embodiment, disclosed herein is a compound having Formula I-a, e.g., a compound having Formula I-a, wherein SM is a monovalent radical of a glucocorticosteroid having any one of Formulae II-a, II-b, II-c, and II-d, wherein A comprises the variable heavy chain CDR1, CDR2, and CDR3 sequences of SEQ ID NO:7 or 8, SEQ ID NO:9, and SEQ ID NO: 10 or 11, respectively, and the variable light chain CDR1, CDR2, and CDR3 sequences of SEQ ID NO:12, SEQ ID NO:13, and SEQ ID NO:14, respectively.

In another embodiment, disclosed herein is a compound having Formula I-a, e.g., a compound having Formula I-a, wherein SM is a monovalent radical of a glucocorticosteroid having any one of Formulae II-a, II-b, II-c, and II-d, wherein A is an anti-TNFα antibody comprising a heavy chain variable region set forth as SEQ ID NO: 5 and a light chain variable region set forth as SEQ ID NO: 6.

In another embodiment, disclosed herein is a compound having Formula I-a, e.g., a compound having Formula I-a, wherein SM is a monovalent radical of a glucocorticosteroid having any one of Formulae II-a, II-b, II-c, and II-d, wherein A is an anti-TNFα antibody comprising a heavy chain set forth as SEQ ID NO: 3 and a light chain set forth as SEQ ID NO: 4.

In another embodiment, disclosed herein is a compound having Formula I-a, e.g., a compound having Formula I-a, wherein SM is a monovalent radical of a glucocorticosteroid having any one of Formulae II-a, II-b, II-c, and II-d, wherein A blocks the interaction of TNFα with p55 and p75 cell surface receptors.

In another embodiment, disclosed herein is a compound having Formula I-a, e.g., a compound having Formula I-a, wherein SM is a monovalent radical of a glucocorticosteroid having any one of Formulae II-a, II-b, II-c, and II-d, wherein A lyses surface TNF expressing cells in vitro in the presence of complement.

In another embodiment, disclosed herein is a compound having Formula I-a, e.g., a compound having Formula I-a, wherein SM is a monovalent radical of a glucocorticosteroid having any one of Formulae II-a, II-b, II-c, and II-d, wherein A is etanercept.

In another embodiment, disclosed herein is a compound having Formula I-a, e.g., a compound having Formula I-a, wherein SM is a monovalent radical of a glucocorticosteroid having any one of Formulae II-a, II-b, II-c, and II-d, wherein A is adalimumab.

In another embodiment, disclosed herein is a compound having Formula I-a, which is any one of the chemical structures of Table 3:

TABLE 3

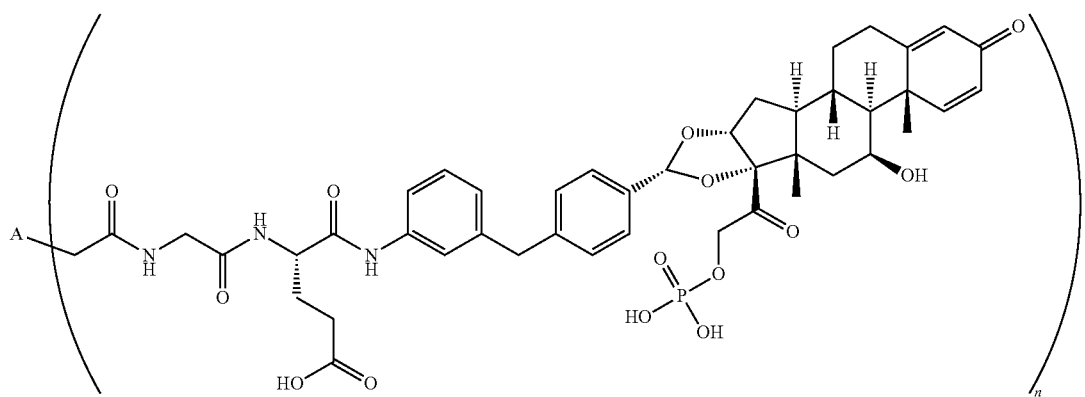

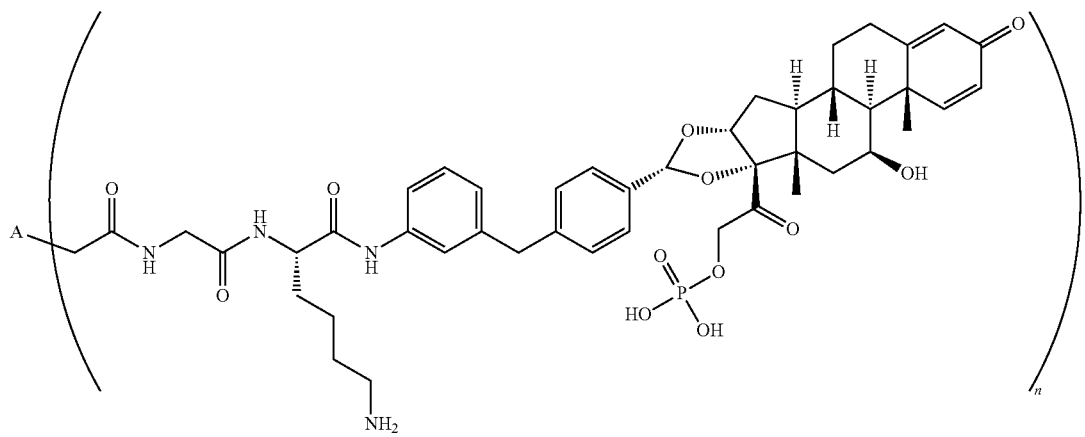

TABLE 3-continued
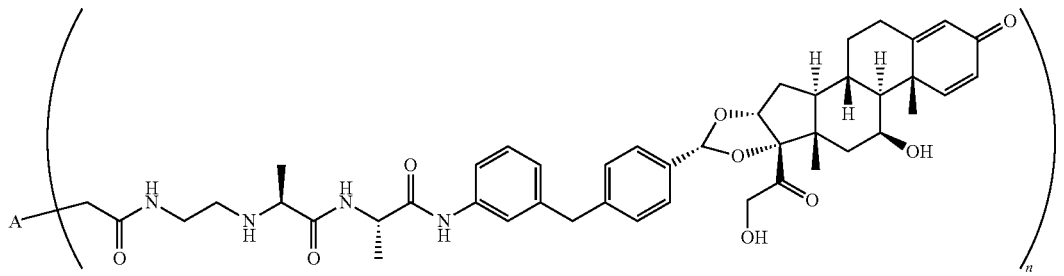
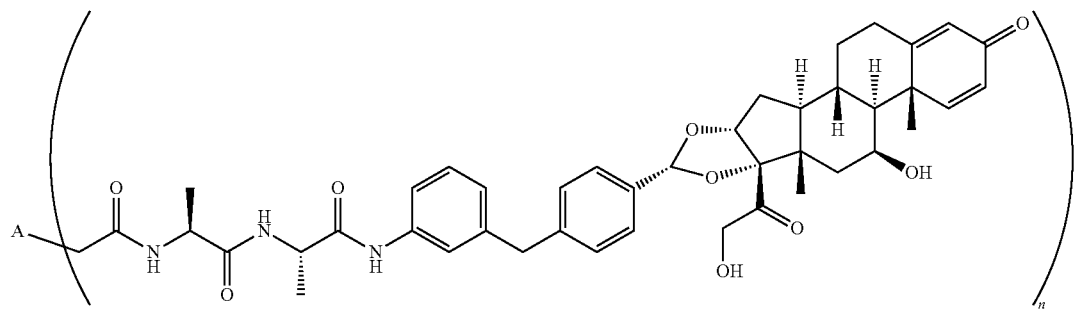
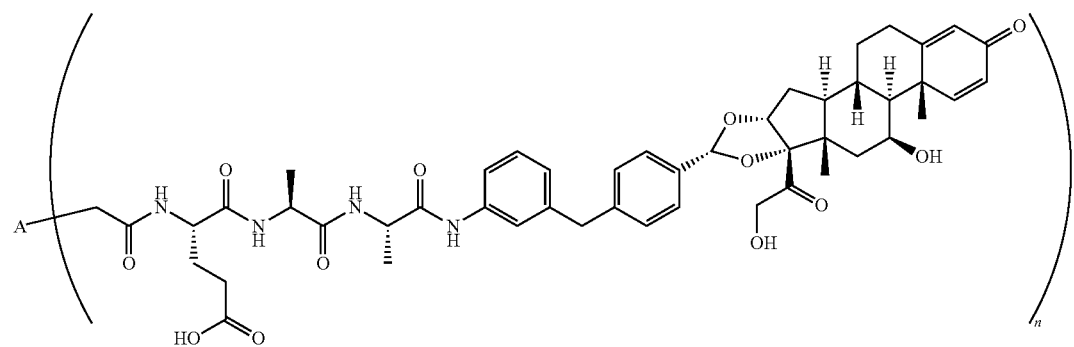
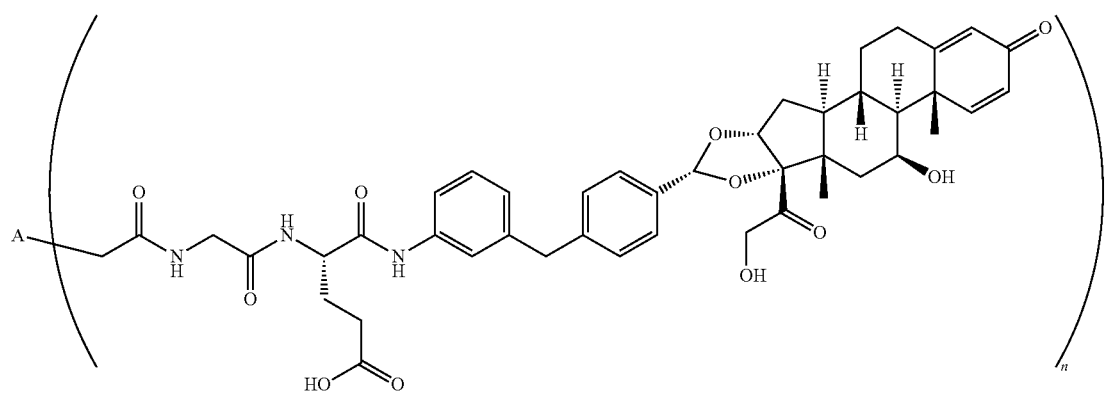

TABLE 3-continued
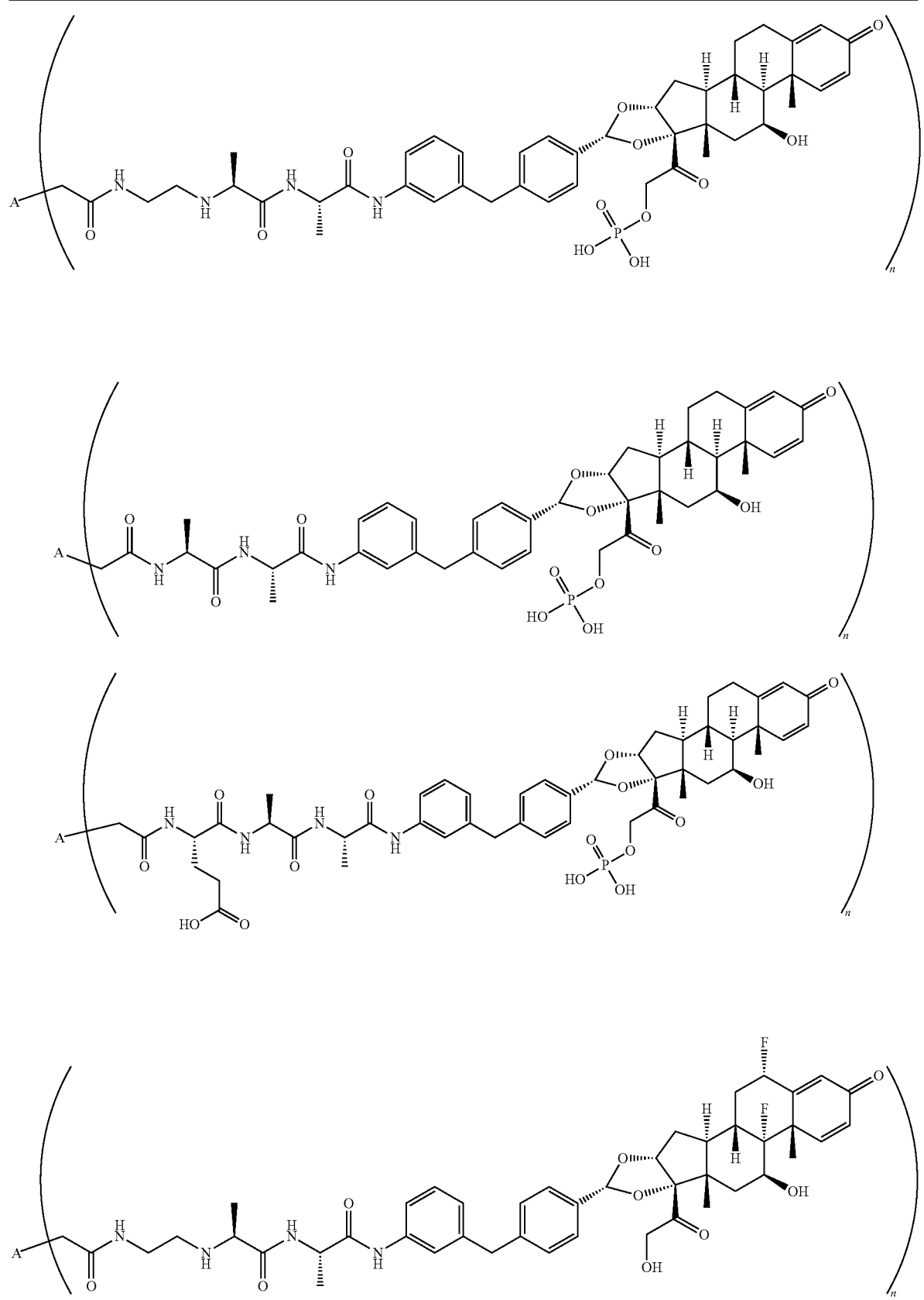

TABLE 3-continued
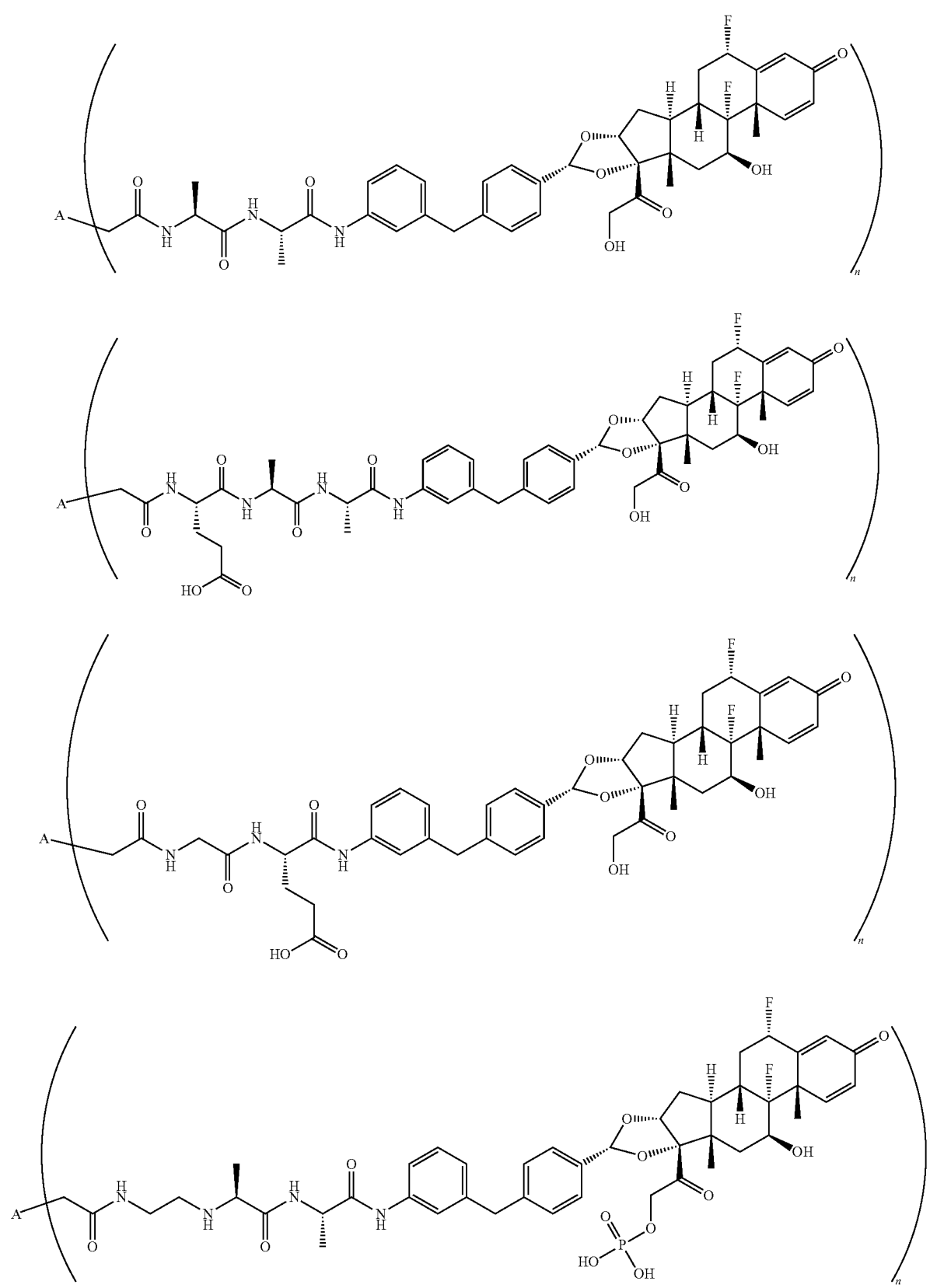

TABLE 3-continued
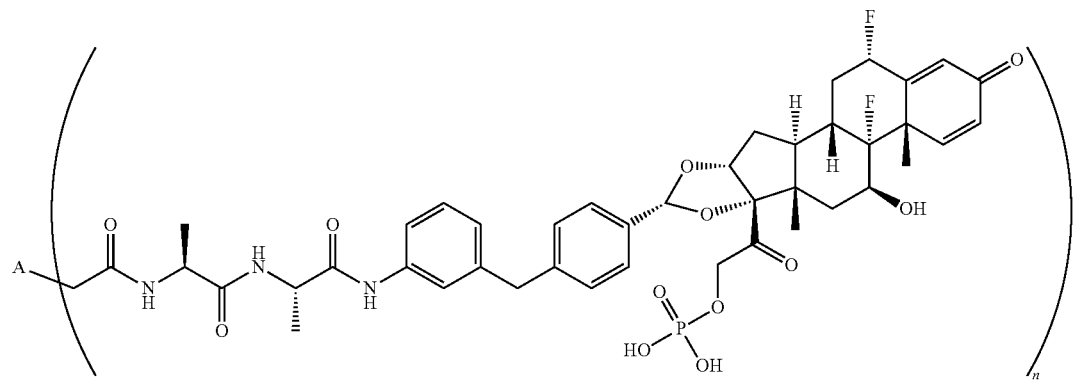
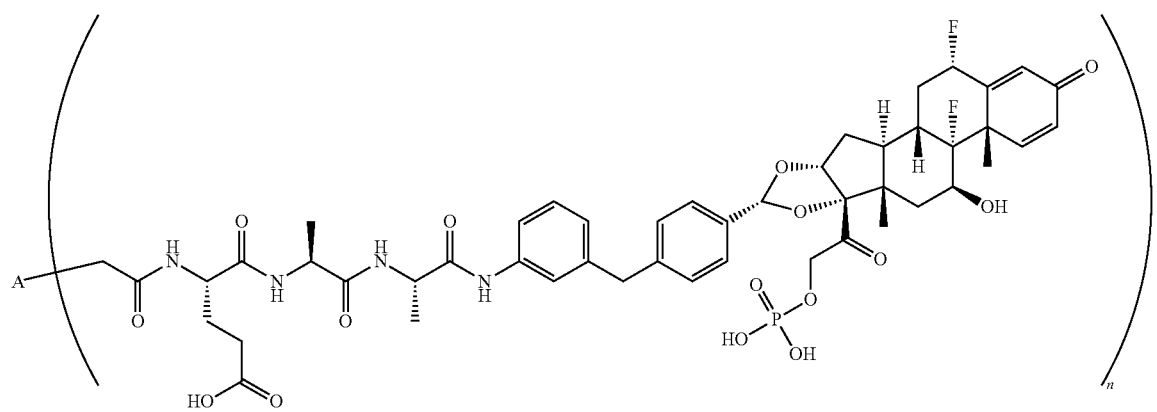
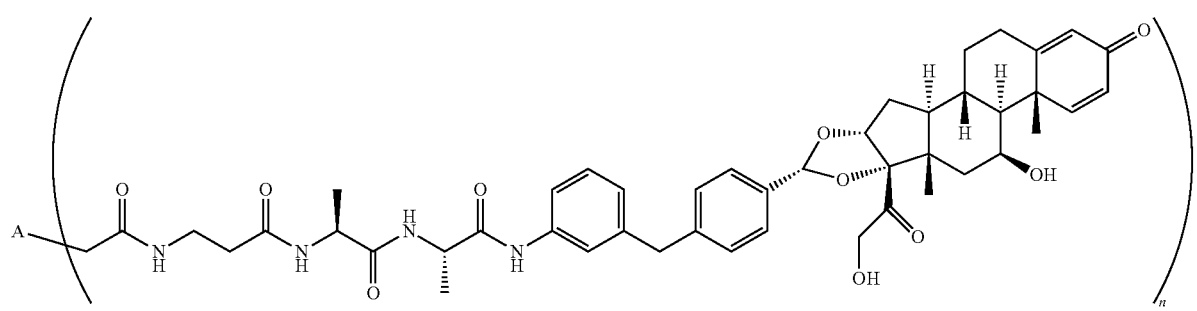
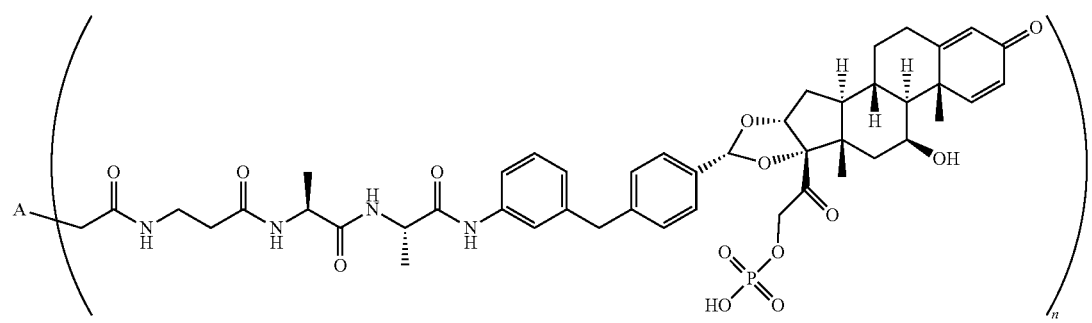

TABLE 3-continued

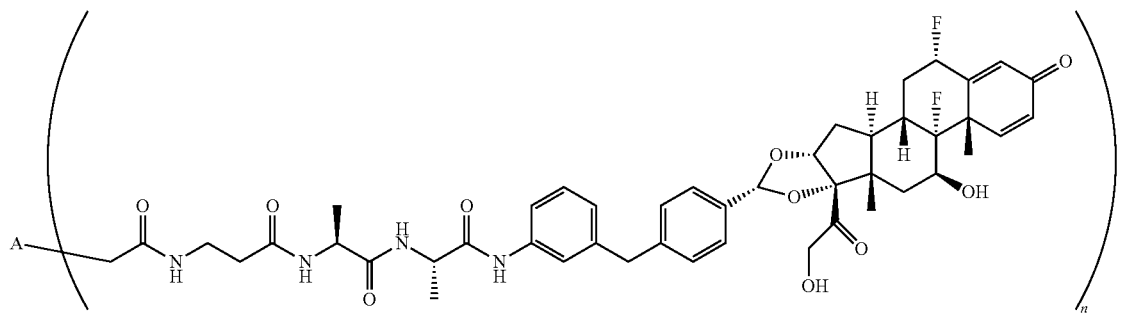

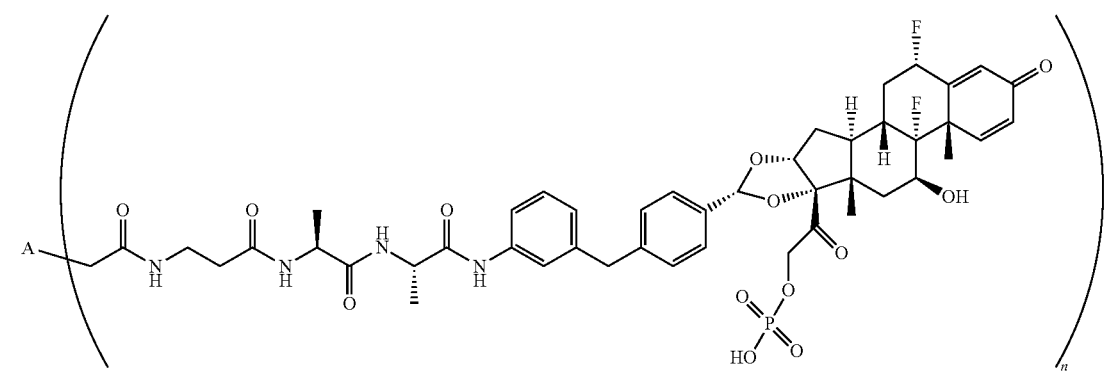

wherein n is 1-=and A is adalimumab.

In another embodiment, disclosed herein is an antibody drug conjugate according to the formula:

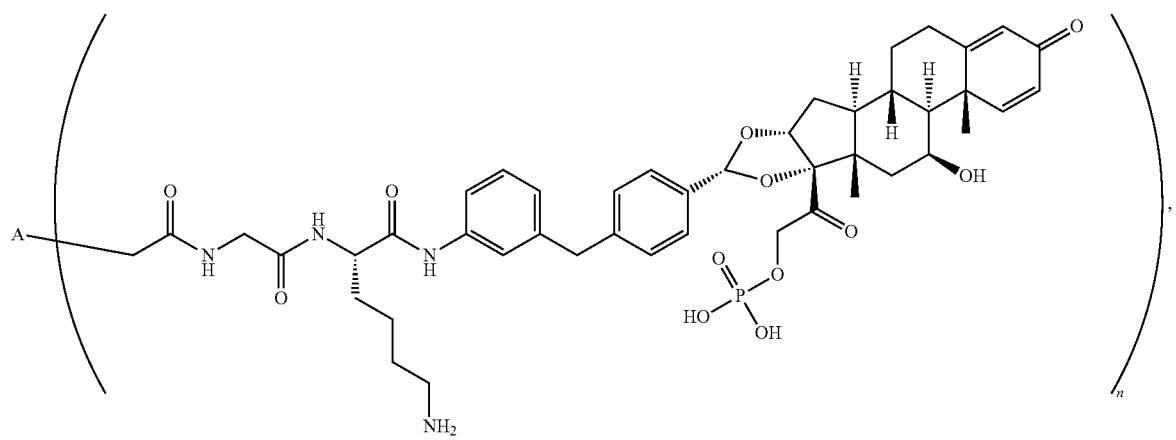

wherein A is adalumimab and n is 4. As demonstrated in Example 7 below, this ADC (i.e., ADC4 below) demonstrates in vitro activity, stability in plasma, and minimal aggregation.

IV. Methods of Making Immunoconjugates and Synthetic Intermediates

The general synthesis of various immunoconjugates of the disclosure involves reacting a NH$_2$-functionalized small molecule (SM) of any of Formulae III-a, III-b, III-c, or III-d below with a linker portion and functionalizing the resulting compound to give a bromoacetamide-functionalized intermediate. The bromoacetamide-functionalized intermediate is then reacted with HS-A, wherein HS-A is an antibody, for example adilumumab, having a limited number of reduced interchain disulfide bonds.

(1) Formula III-a

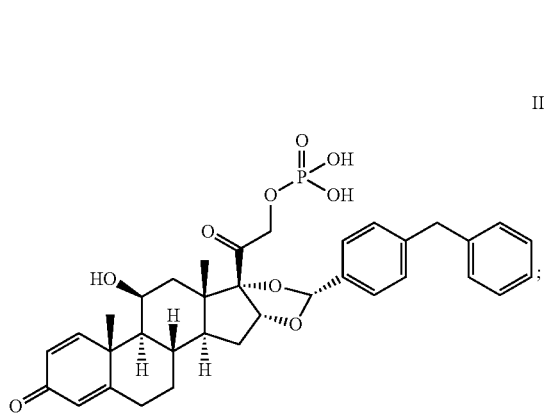

(2) Formula III-b

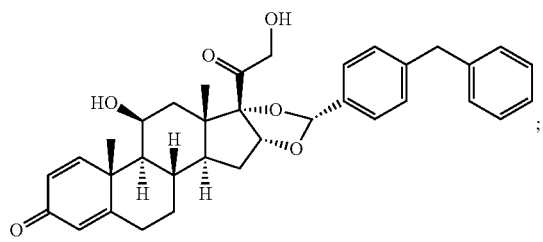

(3) Formula III-c

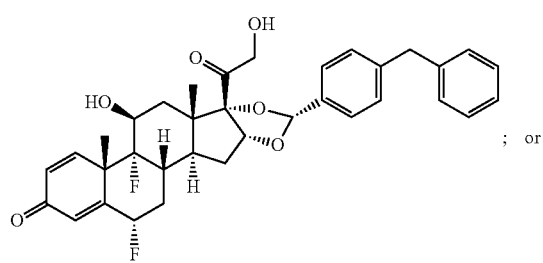

(4) Formula III-d

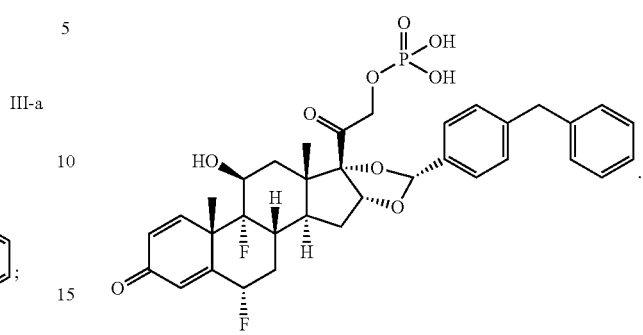

In another embodiment, disclosed herein is a method of making a compound having Formula IV-a:

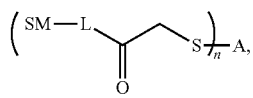

wherein:
A is adalimumab;
L is a linker;
n is 1-10; and
SM is a radical of a glucocorticosteroid having any one of Formulae III-a-IIId;
the method comprising:
a) conjugating a compound having Formula V:

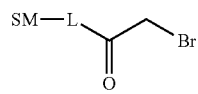

with an anti-tumor necrosis factor (TNF) α protein or a protein; and
b) isolating the compound having Formula IV-a.

In some embodiments, the disclosed method further comprises purifying the compound of Formula IV-a. In certain embodiments, anionic exchange chromatography (AEC) is used, which (due to charged moieties on the peptide portion of the linker in some embodiments and/or the phosphate group on the SM in some embodiments) can provide efficient separation of different DAR species.

In some embodiments, the disclosed method requires fewer synthetic steps than methods relying on standard maleimide-based linker chemistry. In particular, methods relying on standard maleimide-based linker chemistry can require a subsequent succinimide ring-opening hydrolysis step that is performed after purification of the appropriate DAR species. As such, in certain embodiments, the disclosed method significantly shortens the conjugation protocol with respect to standard maleimide-based linker chemistry.

In another embodiment, disclosed herein is a method of making a compound having Formula VI-a:

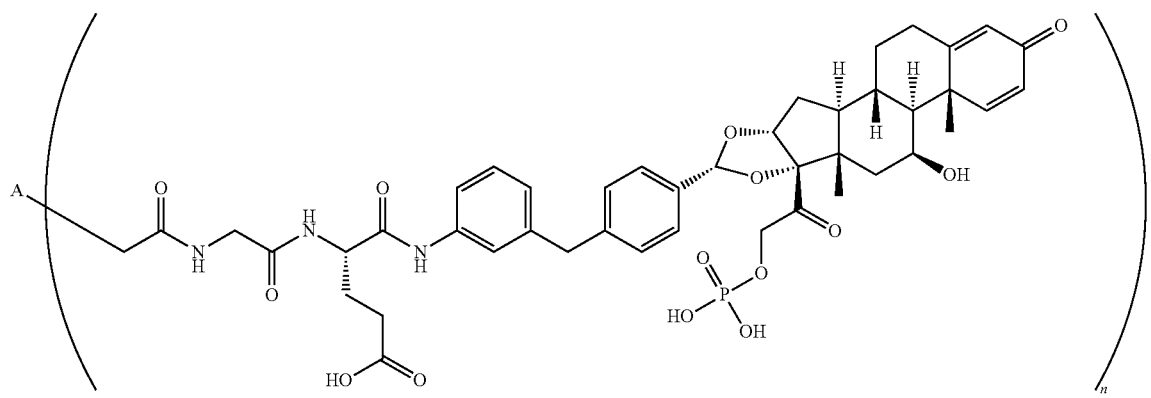

wherein:
A is adalimumab; and
n is 1-10,
the method comprising:
a) conjugating a compound of Formula VII-a:

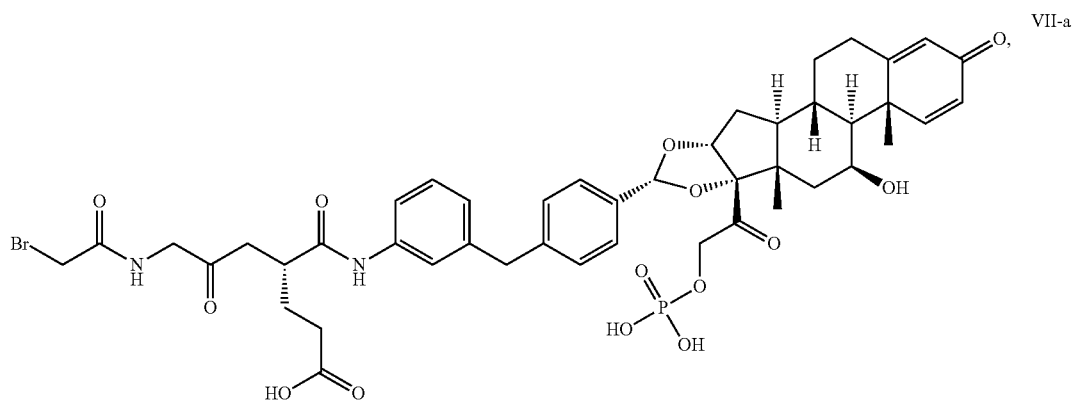

with partially-reduced adalimumab; and
b) isolating, e.g., by chromatography, the compound having Formula VI-a.

In another embodiment, disclosed herein is a method of making a compound having Formula IV-a or Formula VI-a, wherein n is 1-7. In another embodiment, n is 1-5. In another embodiment, n is 2-4. In another embodiment, n is 1. In another embodiment, n is 2. In another embodiment, n is 3. In another embodiment, n is 4. In another embodiment, n is 5. In another embodiment, n is 6. In another embodiment, n is 7. In another embodiment, n is 8.

In another embodiment, disclosed herein is a compound having Formula IV-a or VI-a, wherein:
A is adalimumab; and
n is 1-10.

In another embodiment, disclosed herein is a compound having Formula IV-a or VI-a, wherein n is 1-7. In another embodiment, n is 1-5. In another embodiment, n is 2-4. In another embodiment, n is 1. In another embodiment, n is 2. In another embodiment, n is 3. In another embodiment, n is 4. In another embodiment, n is 5. In another embodiment, n is 6. In another embodiment, n is 7. In another embodiment, n is 8.

Also provided herein are synthetic intermediates that are useful for the preparation of immunoconjugates.

In one embodiment, the synthetic intermediate disclosed herein is a compound having any one of Formulae V or VII-a.

VI. Methods of Use and Pharmaceutical Compositions

Provided herein are conjugates having Formula I-a (e.g., having the formulas shown in Table 3) that can be used in vitro or in vivo. Accordingly, also provided are compositions, e.g., pharmaceutical compositions for certain in vivo uses, comprising a conjugate or a glucocorticoid receptor agonist having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed.

The compositions (e.g., pharmaceutical compositions) to be used for in vivo administration can be sterile, which can be accomplished by filtration through, e.g., sterile filtration membranes. The compositions (e.g., pharmaceutical compositions) to be used for in vivo administration can comprise a preservative.

Antibody drug conjugates and/or pharmaceutical compositions comprising antibody drug conjugates described herein can be useful in lysing a cell expressing surface TNFα (in vitro or in vivo) and/or for the treatment of diseases or disorders characterized by increased TNFα (e.g., increased TNFα in synovial fluid). In some embodiments, the antibody drug conjugates and/or compositions are useful in inhibiting cytokine release (in vitro or in vivo) and/or for the treatment of autoimmune or inflammatory diseases. In some embodiments, the antibody drug conjugates and/or compositions are used for the treatment of Crohn's disease (e.g., moderate to severely active Crohn's disease involving the ileum and/or the ascending colon and/or the maintenance of clinical remission of moderate to severely active Crohn's disease involving the ileum and/or the ascending colon for up to 3 months). In some embodiments, the antibody drug conjugates and/or compositions are used for the treatment of ulcerative colitis (e.g., for the induction of remission in patients with active, moderate to severe ulcerative colitis). In some embodiments, the antibody drug conjugates and/or compositions are used for the treatment of rheumatoid arthritis (RA). In some embodiments, the antibody drug conjugates and/or compositions are used for the treatment of juvenile idiopathic arthritis (JA). In some embodiments, the antibody drug conjugates and/or compositions are used for the treatment of psoriatic arthritis (PsA). In some embodiments, the antibody drug conjugates and/or compositions are used for the treatment of a spondyloarthropathy such as ankylosing spondylitis (AS) or axial spondyloarthritis (ax-SpA). In some embodiments, the antibody drug conjugates and/or compositions are used for the treatment of adult Crohns' disease (CD). In some embodiments, the antibody drug conjugates and/or compositions are used for the treatment of pediatric Crohn's disease. In some embodiments, the antibody drug conjugates and/or compositions are used for the treatment of ulcerative colitis (UC). In some embodiments, the antibody drug conjugates and/or compositions are used for the treatment of plaque psoriasis (Ps). In some embodiments, the antibody drug conjugates and/or compositions are used for the treatment of hidradenitis suppurativa (HS). In some embodiments, the antibody drug conjugates and/or compositions are used for the treatment of uveitis. In some embodiments, the antibody drug conjugates and/or compositions are used for the treatment of Behcets disease. In some embodiments, the antibody drug conjugates and/or compositions are used for the treatment of psoriasis, including plaque psoriasis. Some embodiments comprise use of drug conjugates and/or pharmaceutical compositions for the preparation of a medicament for treating the diseases or disorders described herein.

Some embodiments comprise methods of delivering a glucocorticoid receptor agonist to a TNFα-expressing cell. Such methods can include a step of contacting a TNFα-expressing cell with an antibody drug conjugate as described herein. Some embodiments comprise an in vitro method of delivering a glucocorticoid receptor agonist to a TNFα-expressing cell.

Also provided are methods of determining anti-inflammatory activity of an antibody drug conjugate. Such methods can include a step of contacting a TNFα-expressing cell with an antibody drug conjugate as described herein. Some embodiments comprise contacting a TNFα-expressing cell with an antibody drug conjugate as described herein and determining reduced release of pro-inflammatory cytokines from the cell as compared to a control cell. Some embodiments comprise an in vitro method of determining anti-inflammatory activity of an antibody drug conjugate.

Some embodiments comprise screening methods (e.g. in vitro methods) that include contacting, directly or indirectly, cells (e.g., TNFα-expressing cells) with an antibody drug conjugate and determining if the antibody drug conjugate modulates an activity or function of the cells, as reflected for example by changes in cell morphology or viability, expression of a marker, differentiation or de-differentiation, cell respiration, mitochondrial activity, membrane integrity, maturation, proliferation, viability, apoptosis or cell death. One example of a direct interaction is physical interaction, while an indirect interaction includes, for example, the action of a composition upon an intermediary molecule that, in turn, acts upon the referenced entity (e.g., cell or cell culture).

VII. Articles of Manufacture

The disclosure also includes pharmaceutical packs and kits comprising one or more containers, wherein a container can comprise one or more doses of an antibody drug conjugate or composition as described herein. In certain embodiments, the pack or kit contains a unit dosage, meaning a predetermined amount of a composition or antibody drug conjugate, with or without one or more additional agents.

The kit can comprise one or multiple containers and a label or package insert in, on or associated with the container(s), indicating that the enclosed composition is used for treating the disease condition of choice. Suitable containers include, for example, bottles, vials, syringes, etc. The containers can be formed from a variety of materials such as glass or plastic. The container(s) can comprise a sterile access port, for example, the container may be an intravenous solution bag or a vial having a stopper that can be pierced by a hypodermic injection needle.

In some embodiments the kit can contain a means by which to administer the antibody and any optional components to a patient, e.g., one or more needles or syringes (pre-filled or empty), an eye dropper, pipette, or other such like apparatus, from which the formulation may be injected or introduced into the subject or applied to a diseased area of the body. The kits of the disclosure will also typically include a means for containing the vials, or the like, and other components in close confinement for commercial sale, such as, e.g., blow-molded plastic containers into which the desired vials and other apparatus are placed and retained.

EXAMPLES

It is understood that the examples and embodiments described herein are for illustrative purposes only and that various modifications or changes in light thereof will be suggested to persons skilled in the art and are to be included within the spirit and purview of this disclosure.

Starting materials are commercially available, may be prepared by the procedures described herein, by literature procedures, or by procedures that would be well known to one skilled in the art of organic chemistry. Reagent/reactant names given are as named on the commercial bottle or as generated by IUPAC conventions, CambridgeSoft® Chem-Draw Ultra 12.0, CambridgeSoft® Chemistry E-Notebook 11, or AutoNom 2000. It is understood that the examples and embodiments described herein are for illustrative purposes only and that various modifications or changes in light thereof will be suggested to persons skilled in the art and are to be included within the spirit and purview of this disclosure.

Analytical Methods for Compound Synthesis and Characterization

Analytical data is included within the procedures below, in the illustrations of the general procedures, or in the tables of examples. Unless otherwise stated, all $^1$H and $^{13}$C NMR data were collected on a Varian Mercury Plus 400 MHz or a Bruker AVIII 300 MHz instrument; chemical shifts are quoted in parts per million (ppm). HPLC analytical data are either detailed within the experimental or referenced to the table of LC/MS and HPLC conditions, using the method provided in Table 4.

TABLE 4

| Method | Conditions |
|---|---|
| a | The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% TFA in H$_2$O, mobile phase B was 0.018% TFA in MeCN. The column used for the chromatography was a 2.0 × 50 mm Phenomenex Luna-C18 column (5 μm particles). Detection methods are DAD and ELSD as well as positive electrospray ionization. |

Abbreviations used in the examples that follow are:

| | |
|---|---|
| ACTH | Adrenocorticotropic Hormone |
| BrAc | Bromo acetamide |
| CV | Column volumes |
| DAD | Diode array |
| DAR | Drug to antibody ratio |
| DBP | Dibutyl phthalate |
| DCM | Dichloromethane |
| DMA | Dimethyl acetamide |
| DMF | Dimethyl formamide |
| DMSO | Dimethyl sulfoxide |
| DTT | Dithiothreitol |
| EEDQ | 2-Ethoxy-1-ethoxycarbonyl-1,2-dihydroquinoline |
| ELSD | Evaporative light scattering detector |
| Eq | Equivalents |
| EtOAc | Ethyl acetate |
| FBS | Fetal Bovine Serum |
| Fmoc | 9-Fluorenylmethyloxycarbonyl |
| HIC | Hydrophobic Interaction Chromatography |
| HPLC | High performance liquid chromatography |
| LCMS | Liquid chromatography mass spectrometry |
| MeCN | Acetonitrile |
| MEM | Minimal Essential Media |
| MeOH | Methanol |
| MS | Mass spectrometry |
| NEAA | Non-essential amino acids |
| NMR | Nuclear magnetic resonance |
| PBS | Phosphate buffer saline |
| PE | Petroleum ether |
| P1NP | Procollagen type 1 amino-terminal propeptide |
| rt | Room temperature |
| RPMI | Roswell Park Memorial Institute |
| SEC | Size exclusion chromatography |
| TCEP | (tris(2-carboxyethyl)phosphine) |
| TFA | Trifluoro acetic acid |

Example 1

Synthesis of (2S,6aS,6bR,7S,8aS,8bS,10S,11aR, 12aS,12bS)-10-(4-(3-aminobenzyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one Step 1: Synthesis of 4-(bromomethyl)benzaldehyde

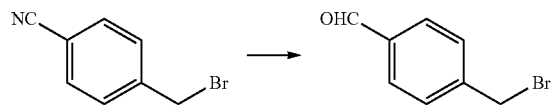 [SMILES: N#Cc1ccc(CBr)cc1 ; O=Cc1ccc(CBr)cc1]

Diisobutylaluminum hydride (153 mL, 153 mmol, 1 M in toluene) was added drop-wise to a 0° C. solution of 4-(bromomethyl)benzonitrile (20 g, 102 mmol) in toluene (400 mL) over 1 hour. Two additional vials were set up as described above. All three reaction mixtures were combined. To the mixture was added 10% aqueous HCl (1.5 L). The mixture was extracted with DCM (3×500 mL). The organic layer was dried over Na$_2$SO$_4$, filtered and concentrated under reduced pressure. The residue was purified by column chromatography on silica gel (eluted with PE:EtOAc=10:1) to obtain the title compound (50 g, yield 82%) as white solid. $^1$H NMR (400 MHz, CDCl$_3$) δ 10.02 (s, 1H), 7.91-7.82 (m, 2H), 7.56 (d, J=7.9 Hz, 2H), 4.55-4.45 (m, 2H).

Step 2: Synthesis of 3-(4,4,5,5-tetramethyl-1,3,2-dioxaborolan-2-yl)aniline

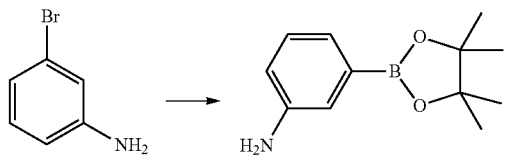

To a solution of 3-bromoaniline (40 g, 233 mmol) in 1,4-dioxane (480 mL) was added 4,4,4',4',5,5,5',5'-tetramethyl-2,2'-bi(1,3,2-dioxaborolane) (94 g, 372 mmol), potassium acetate (45.6 g, 465 mmol), 2-dicyclohexylphosphino-2',4',6'-tri-i-propyl-1,1'-biphenyl (8.07 g, 13.95 mmol), and tris(dibenzylideneacetone)dipalladium(0) (8.52 g, 9.30 mmol). The resulting mixture was heated at 80° C. for 4 hours under nitrogen. An additional vial was set up as described above. The two reaction mixtures were combined and concentrated and the residue was purified by column chromatography on silica gel (eluted with PE:EtOAc=10:1) to obtain the title compound (60 g, yield 55.4%) as a light yellow solid. $^1$H NMR (400 MHz, CDCl$_3$) δ 7.23-7.13 (m, 3H), 6.80 (d, J=7.5 Hz, 1H), 3.82-3.38 (m, 2H), 1.34 (s, 12H).

Step 3: Synthesis of tert-butyl (3-(4,4,5,5-tetramethyl-1,3,2-dioxaborolan-2-yl)phenyl)carbamate

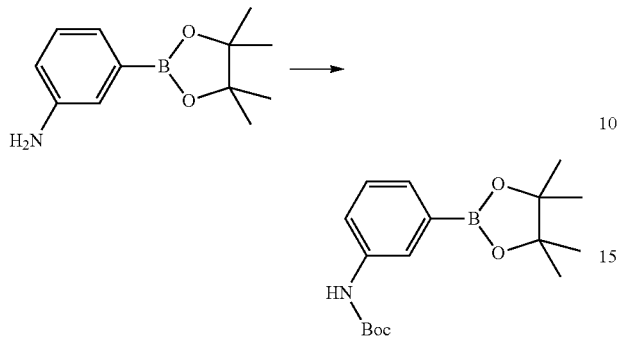

3-(4,4,5,5-Tetramethyl-1,3,2-dioxaborolan-2-yl)aniline (Example 1, Step 2) (30 g, 137 mmol) and di-tert-butyl dicarbonate (38.9 g, 178 mmol) were mixed in toluene (600 mL) at 100° C. for 24 hours. Another vial was set up as described above. The two reaction mixtures were combined and the mixture was evaporated, dissolved in EtOAc (1.5 L), washed with 0.1 N HCl (3×2 L) and brine (3 L), dried over Na$_2$SO$_4$, filtered and concentrated under reduced pressure to give the title compound (50 g, yield 57%) as a red solid. $^1$H NMR (400 MHz, CDCl$_3$) δ 7.63 (br m, 2H), 7.48 (d, J=7.1 Hz, 1H), 7.37-7.28 (m, 1H), 1.52 (s, 9H), 1.34 (s, 12H).

Step 4: Synthesis of tert-butyl (3-(4-formylbenzyl)phenyl)carbamate

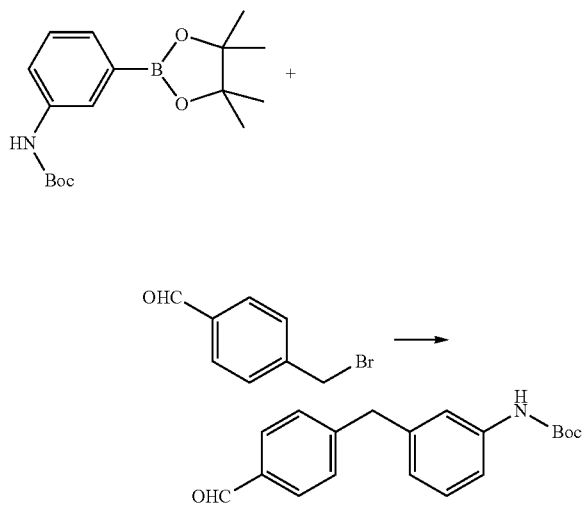

A mixture of 4-(bromomethyl)benzaldehyde (Example 1, Step 1) (24.94 g, 125 mmol), 1,1'-bis(diphenylphosphino) ferrocenedichloro palladium(II) DCM complex (13.75 g, 18.80 mmol), tert-butyl (3-(4,4,5,5-tetramethyl-1,3,2-dioxaborolan-2-yl)phenyl) carbamate (from Example 1, Step 3) (20 g, 62.7 mmol) and potassium carbonate (43.3 g, 313 mmol) in tetrahydrofuran (400 mL) was heated to 80° C. for 12 hours. Another vial was set up as described above. The two reaction mixtures were combined and diluted with water (500 mL). The aqueous mixture was extracted with EtOAc (3×500 mL). The organic layers were combined and dried over Na$_2$SO$_4$, filtered and concentrated under reduced pressure. The residue was purified by column chromatography on silica gel (eluted with PE:EtOAc=10:1) to obtain the title compound (15 g, yield 38.4%) as white solid. $^1$H NMR (400 MHz, CDCl$_3$) δ 9.95 (s, 1H), 7.78 (d, J=7.9 Hz, 2H), 7.33 (d, J=7.9 Hz, 2H), 7.27-7.13 (m, 3H), 6.82 (d, J=7.1 Hz, 1H), 6.47 (br. s., 1H), 4.00 (s, 2H), 1.48 (s, 9H).

Step 5: Synthesis of (6S,8S,9R,10S,11S,13S,14S, 16R,17S)-6,9-difluoro-11,16,17-trihydroxy-17-(2-hydroxyacetyl)-10,13-dimethyl-6,7,8,9,10,11,12,13, 14,15,16,17-dodecahydro-3H-cyclopenta[a] phenanthren-3-one

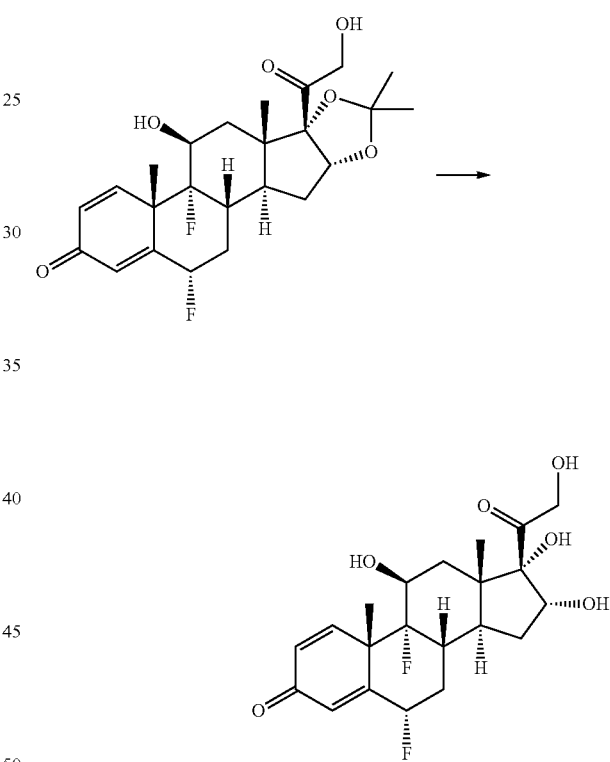

(2S,6aS,6bR,7S,8aS,8bS,11aR,12aS,12bS)-2,6b-Difluoro-7-hydroxy-8b-(2-hydroxyacetyl)-6a,8a,10,10-tetramethyl-1,2,6a,6b,7,8,8a,8b,11a,12,12a,12b-dodecahydro-4H-naphtho[2',1':4,5]indeno[1,2-d][1,3]dioxol-4-one (20 g, 44.2 mmol) was suspended in 40% aqueous HBF$_4$ (440 mL) and the mixture was stirred at 25° C. for 48 hours. After the reaction was complete, 2 L of water was added and the solid was collected by filtration. This solid was washed with water (1 L) and then MeOH (200 mL) to give the title compound (11 g, yield 60.3%) as a white solid. $^1$H NMR (400 MHz, DMSO-d6) δ 7.25 (d, J=10.1 Hz, 1H), 6.28 (d, J=10.1 Hz, 1H), 6.10 (s, 1H), 5.73-5.50 (m, 1H), 5.39 (br. s., 1H), 4.85-4.60 (m, 2H), 4.50 (d, J=19.4 Hz, 1H), 4.20-4.04 (m, 2H), 2.46-2.06 (m, 6H), 1.87-1.75 (m, 1H), 1.56-1.30 (m, 6H), 0.83 (s, 3H).

Step 6: Synthesis of (2S,6aS,6bR,7S,8aS,8bS,10R, 11aR,12aS,12bS)-10-(4-(3-aminobenzyl)phenyl)-2, 6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1, 3]dioxol-4-one

| | Time | | | | | | |
|---|---|---|---|---|---|---|---|
| | 0.0 | 10.5 | 10.6 | 10.7 | 13.7 | 13.8 | 15.0 |
| B % | 15 | 35 | 35 | 100 | 100 | 10 | 10 |

Example 2

Synthesis of (6aR,6bS,7S,8aS,8bS,10R,11aR,12aS, 12bS)-10-(4-(3-aminobenzyl)phenyl)-7-hydroxy-8b-(2-hydroxyacetyl)-6a,8a-dimethyl-1,2,6a,6b,7,8,8a, 8b,11a,12,12a,12b-dodecahydro-4H-naphtho[2',1':4, 5]indeno[1,2-d][1,3]dioxol-4-one.

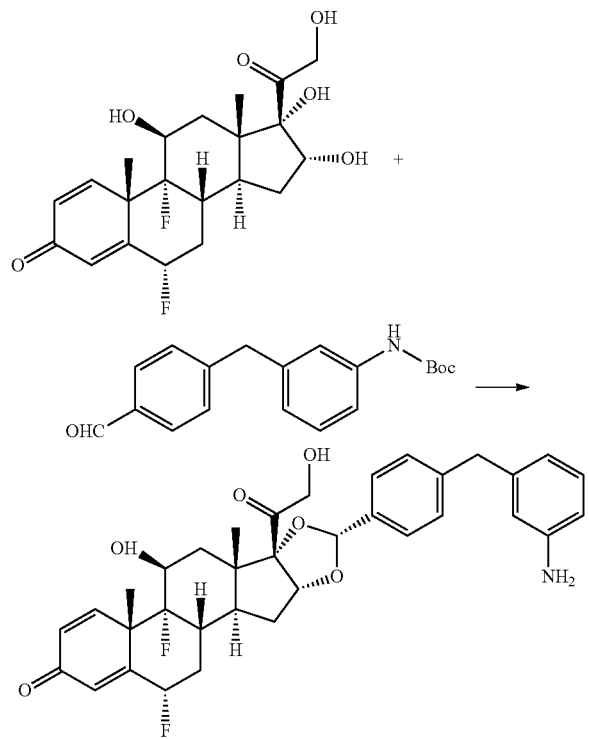

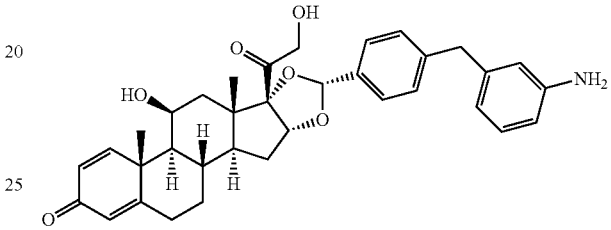

A suspension of (6S,8S,9R,10S,11S,13S,14S,16R,17S)-6, 9-difluoro-11,16,17-trihydroxy-17-(2-hydroxyacetyl)-10, 13-dimethyl-6,7,8,9,10,11,12,13,14,15,16,17-dodecahydro-3H-cyclopenta[a]phenanthren-3-one (Example 1, Step 5) (4.4 g, 10.67 mmol) and MgSO₄ (6.42 g, 53.3 mmol) in MeCN (100 mL) was stirred at 20° C. for 1 hour A solution of tert-butyl (3-(4-formylbenzyl)phenyl)carbamate (Example 1, Step 4) (3.65 g, 11.74 mmol) in MeCN (100 mL) was added in one portion. Trifluoromethanesulfonic acid (9.01 mL, 53.3 mmol) was added dropwise while maintaining an internal temperature below 25° C. using an ice bath. After the addition, the mixture was stirred at 20° C. for 2 hours. Three additional vials were set up as described above. All four reaction mixtures were combined and concentrated and the residue was purified by Prep HPLC to give the title compound (4.5 g, yield 14.2%) as yellow solid. LCMS (Method a, Table 4) $R_t$=2.65 min; MS m/z=606.2 (M+H)⁺; ¹H NMR (400 MHz, DMSO-d6) δ 7.44-7.17 (m, 5H), 6.89 (t, J=7.7 Hz, 1H), 6.44-6.25 (m, 4H), 6.13 (br. s., 1H), 5.79-5.52 (m, 2H), 5.44 (s, 1H), 5.17-4.89 (m, 3H), 4.51 (d, J=19.4 Hz, 1H), 4.25-4.05 (m, 2H), 3.73 (s, 2H), 3.17 (br. s., 1H), 2.75-2.55 (m, 1H), 2.36-1.97 (m, 3H), 1.76-1.64 (m, 3H), 1.59-1.39 (m, 4H), 0.94-0.78 (m, 3H). Prep HPLC Method: Instrument: Gilson 281 semi-preparative HPLC system; Mobile phase: A: Formic Acid/H₂O=0.01% v/v; B: MeCN; Column: Luna C18 150*25 5 micron; Flow rate: 25 mL/min; Monitor wavelength: 220 and 254 nm.

Example 2 was synthesized in a similar procedure to Example 1 using (8S,9S,10R,11S,13S,14S,16R,17S)-11,16, 17-trihydroxy-17-(2-hydroxyacetyl)-10,13-dimethyl-6,7,8, 9,10,11,12,13,14,15,16,17-dodecahydro-3H-cyclopenta[a] phenanthren-3-one.

¹H NMR (400 MHz, DMSO-d₆) δ 7.36 (d, J=7.9 Hz, 2H), 7.31 (d, J=10.1 Hz, 1H), 7.20 (d, J=7.9 Hz, 2H), 6.89 (t, J=7.9 Hz, 1H), 6.39-6.28 (m, 3H), 6.16 (dd, J=1.5, 9.9 Hz, 1H), 5.93 (s, 1H), 5.39 (s, 1H), 5.08 (t, J=5.7 Hz, 1H), 4.98-4.87 (m, 3H), 4.78 (d, J=3.1 Hz, 1H), 4.49 (dd, J=6.2, 19.4 Hz, 1H), 4.29 (br. s., 1H), 4.17 (dd, J=5.5, 19.6 Hz, 1H), 3.74 (s, 2H), 2.61-2.53 (m, 1H), 2.36-2.26 (m, 1H), 2.11 (d, J=11.0 Hz, 1H), 2.07 (s, 1H), 2.02 (d, J=12.8 Hz, 1H), 1.83-1.54 (m, 5H), 1.39 (s, 3H), 1.16-0.96 (m, 2H), 0.85 (s, 3H).

LCMS (Method a, Table 4) $R_t$=2.365 min; m/z=570.2 (M+H)⁺.

Example 3

Synthesis of (6aS,6bR,7S,8aS,8bS,10R,11aR,12aS, 12bS)-10-(4-(3-aminobenzyl)phenyl)-6b-fluoro-7-hydroxy-8b-(2-hydroxyacetyl)-6a,8a-dimethyl-1,2, 6a,6b,7,8,8a,8b,11a,12,12a,12b-dodecahydro-4H-naphtho[2',1':4,5]indeno[1,2-d][1,3]dioxol-4-one.

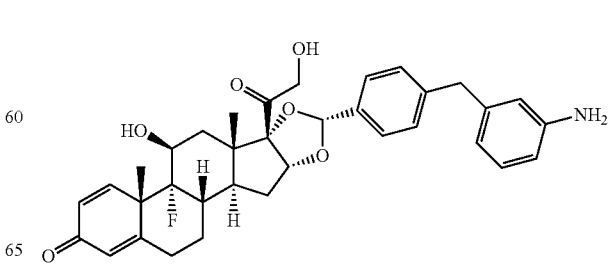

Example 3 was synthesized in a similar procedure to Example 1 using (8S,9R,10S,11S,13S,14S,16R,17S)-9-fluoro-11,16,17-trihydroxy-17-(2-hydroxyacetyl)-10,13-dimethyl-6,7,8,9,10,11,12,13,14,15,16,17-dodecahydro-3H-cyclopenta[a]phenanthren-3-one.

$^1$H NMR (400 MHz, DMSO-d$_6$) δ 7.37-7.26 (m, 3H), 7.21 (d, J=7.9 Hz, 2H), 6.89 (t, J=7.7 Hz, 1H), 6.43-6.30 (m, 3H), 6.23 (d, J=10.1 Hz, 1H), 6.04 (s, 1H), 5.75 (s, 1H), 5.44 (s, 2H), 5.09 (t, J=5.7 Hz, 1H), 4.93 (br. s., 3H), 4.50 (dd, J=6.2, 19.4 Hz, 1H), 4.28-4.09 (m, 2H), 3.74 (s, 2H), 2.73-2.54 (m, 2H), 2.35 (d, J=13.2 Hz, 1H), 2.25-2.12 (m, 1H), 2.05 (d, J=15.0 Hz, 1H), 1.92-1.77 (m, 1H), 1.74-1.58 (m, 3H), 1.50 (s, 3H), 1.45-1.30 (m, 1H), 0.87 (s, 3H). LCMS (Method a, Table 4) R$_t$=2.68 min; m/z=588.1 (M+H)$^+$

Example 4

Synthesis of (S)-4-(2-(2-bromoacetamido)acetamido)-5-((3-(4-((6aR,6bS,7S,8aS,8bS,10R,11aR,12aS,12bS)-7-hydroxy-6a,8a-dimethyl-4-oxo-8b-(2-(phosphonooxy)acetyl)-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-5-oxopentanoic acid Step 1: Synthesis of (S)-2-(2-((((9H-fluoren-9-yl)methoxy)carbonyl)amino)acetamido)-5-(tert-butoxy)-5-oxopentanoic acid

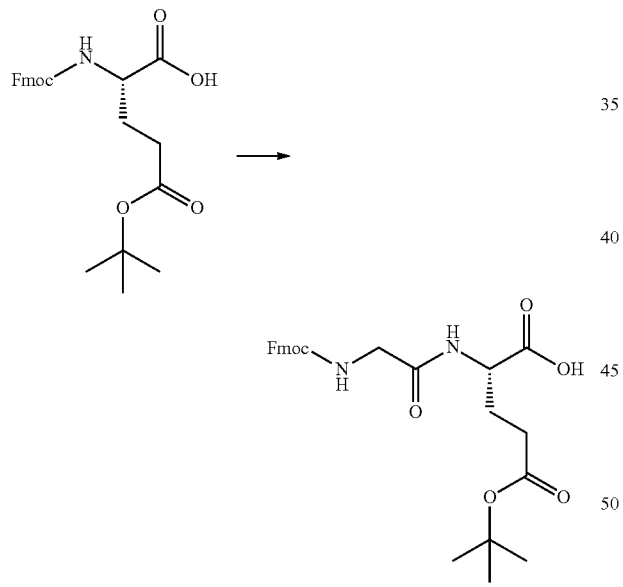

A mixture of 2-chlorotrityl chloride resin (30 g, 92 mmol), triethylamine (46.4 g, 458 mmol) and (S)-2-((((9H-fluoren-9-yl)methoxy)carbonyl)amino)-5-(tert-butoxy)-5-oxopentanoic acid (25.5 g, 60 mmol) in dry DCM (200 mL) was bubbled with N$_2$ at 20° C. for 8 hours. The mixture was filtered and the resin was washed with DCM (2×200 mL), MeOH (2×200 mL), and DMF (2×200 mL). The resin was added a solution of piperidine:DMF (1:4, 400 mL) and the mixture was bubbled with N$_2$ for 8 minutes and then filtered. This operation was repeated five times to give complete removal of the Fmoc protecting group. The resin was washed with DMF (5×500 mL) to afford resin bound (S)-2-amino-5-(tert-butoxy)-5-oxopentanoic acid. A mixture of 2-((((9H-fluoren-9-yl)methoxy)carbonyl)amino)acetic acid (13.38 g, 45.0 mmol), N,N-diisopropylethylamine (7.86 mL, 45 mmol), hydroxybenzotriazole (6.89 g, 45 mmol), 2-(6-chloro-1H-benzo[d][1,2,3]triazol-1-yl)-1,1,3,3-tetramethylisouronium hexafluorophosphate (V) (18.62 g, 45.0 mmol) in DMF (200 mL) was stirred at 20° C. for 30 min. To the mixture was added the resin bound (S)-2-amino-5-(tert-butoxy)-5-oxopentanoic acid and the resulting mixture was bubbled with N$_2$ at 25° C. for 1.5 hours. The mixture was filtered and the resin was washed with DMF (4×500 mL), and DCM (2×500 mL). To the mixture was added 1% TFA/DCM (5×500 mL) and bubbled with N$_2$ for 5 minutes. The mixture was filtered and the filtrate was added to saturated solution of NaHCO$_3$ (200 mL) directly. The combined mixture was separated, and the organic phase was washed with saturated citric acid water solution (4×400 mL) and brine (2×300 mL). The final organic solution was dried over Na$_2$SO$_4$ (20 g), filtered, concentrated under reduced pressure to afford the title compound (10 g, yield 20%) as a light yellow solid.

$^1$H NMR: (CDCl$_3$, 400 MHz) δ=7.75 (d, J=7.5 Hz, 2H), 7.59 (br d, J=7.5 Hz, 2H), 7.41-7.36 (m, 2H), 7.30 (t, J=7.0 Hz, 2H), 5.82 (br s, 1H), 4.57 (br d, J=4.8 Hz, 1H), 4.38 (br d, J=7.5 Hz, 2H), 4.27-4.15 (m, 1H), 4.06-3.83 (m, 2H), 2.50-2.29 (m, 2H), 2.26-2.13 (m, 1H), 2.06-2.02 (m, 1H), 1.43 (s, 9H).

Step 2: Synthesis of tert-butyl (S)-4-(2-((((9H-fluoren-9-yl)methoxy)carbonyl)amino)acetamido)-5-((3-(4-((6aR,6bS,7S,8aS,8bS,10R,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-5-oxopentanoate

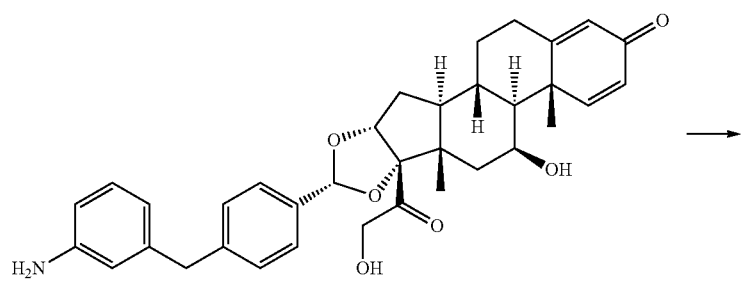

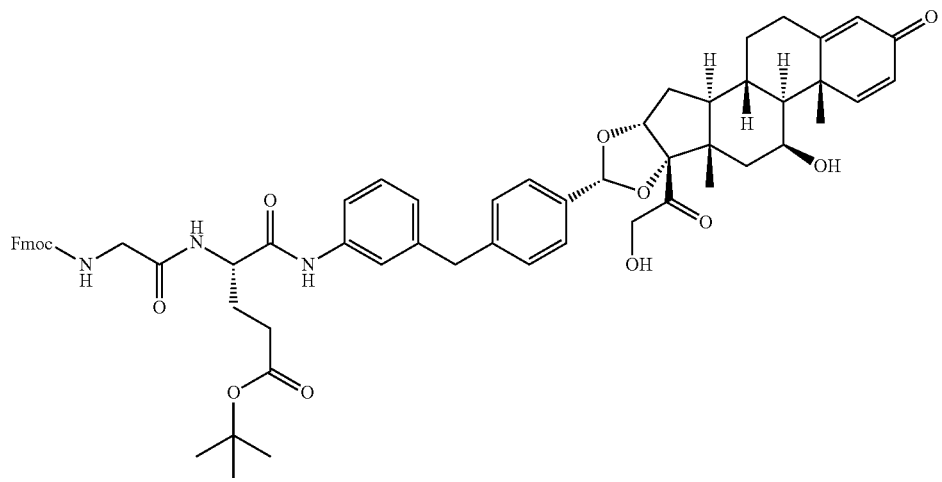

To a solution of (S)-2-(2-(((((9H-fluoren-9-yl)methoxy)carbonyl)amino)acetamido)-5-(tert-butoxy)-5-oxopentanoic acid (Example 4, step 1) (424 mg, 0.878 mmol) in DMF (3.5 mL) was added (6aR,6bS,7S,8aS,8bS,10R,11aR,12aS,12bS)-10-(4-(3-aminobenzyl)phenyl)-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (Example 2) (500 mg, 0.878 mmol) and triethylamine (0.3 mL, 2.63 mmol) at 25° C. The solution was cooled to 0° C. and then 2,4,6-tripropyl-1,3,5,2,4,6-trioxatriphosphinane 2,4,6-trioxide (1.12 g, 1.755 mmol) was added. The reaction mixture was stirred for 12 hours at 25° C. LCMS showed the reaction was complete. Fourteen additional vials were set up as described above. All fifteen reaction mixtures were combined. The mixture was purified by reverse phase column to afford the title compound (5 g, yield 38.4%) as a yellow solid. Reverse phase column method: Instrument: Shimadzu LC-8A preparative HPLC; Column: Phenomenex Luna C18 200*40 mm*10 μm; Mobile phase: A for $H_2O$ (0.05% TFA) and B for MeCN; Gradient: B from 30% to 100% in 30 min; Flow rate: 60 mL/min; Wavelength: 220 & 254 nm.

LCMS (Method a, Table 4) $R_f$=1.34 min; m/z 1016.6 (M+H−18)$^+$.

Step 3: Synthesis of tert-butyl (S)-4-(2-(((((9H-fluoren-9-yl)methoxy)carbonyl)amino)acetamido)-5-((3-(4-((6aR,6bS,7S,8aS,8bS,10R,11aR,12aS,12bS)-8b-(2-((di-tert-butoxyphosphoryl)oxy)acetyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-5-oxopentanoate

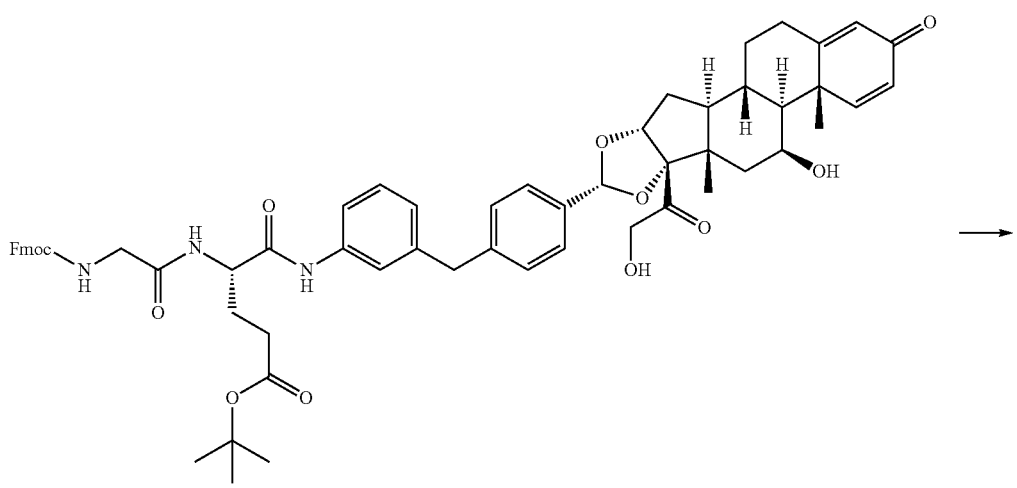

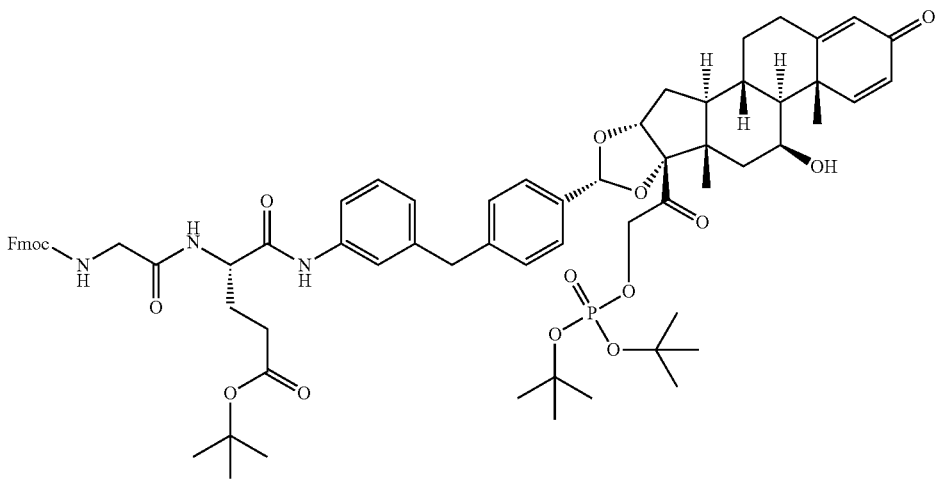

To a solution of tert-butyl (S)-4-(2-((((9H-fluoren-9-yl)methoxy)carbonyl)amino)acetamido)-5-((3-(4-((6aR,6bS,7S,8aS,8bS,10R,11aR,12aS,12S)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-5-oxopentanoate (Example 4, step 2) (400 mg, 0.387 mmol) in DMF (2.5 mL) was added 1H-tetrazole (271 mg, 3.87 mmol) and di-tert-butyl diethylphosphoramidite (1.16 g, 4.64 mmol). The reaction was stirred at rt for 2.5 hours then cooled to 0° C. Hydrogen peroxide (241 mg, 2.127 mmol) was added to the resulting mixture allowed to warm to rt and stirred for 1 hour after which time LCMS showed the reaction was complete. Eleven additional vials were set up as described above. All twelve reaction mixtures were combined. The mixture was purified by reverse phase column to afford the title compound (4.4 g, yield 64.2%) as a yellow solid. Reverse phase column method: Instrument: Shimadzu LC-8A preparative HPLC; Column: Phenomenex Luna C18 200*40 mm*10 μm; Mobile phase: A for H$_2$O and B for MeCN; Gradient: B from 50% to 100% in 30 min; Flow rate: 60 mL/min; Wavelength: 220 & 254 nm. LCMS (Method a, Table 4) R$_t$=1.41 min; m/z 1226.7 (M+H)$^+$.

Step 4: Synthesis of tert-butyl (S)-4-(2-aminoacetamido)-5-((3-(4-((6aR,6bS,7S,8aS,8bS,10R,11aR,12aS,12bS)-8b-(2-((di-tert-butoxyphosphoryl)oxy)acetyl)-7-hydroxy-6a,8a-dimethyl- 4-oxo-2,4,6a,6b,7,8,8a,8b,11 a,12,12a,12b-dodecahydro-1H-naphtho[2',1':4,5]indeno[1,2-d][1,3]dioxol-10-yl)benzyl)phenyl)amino)-5-oxopentanoate

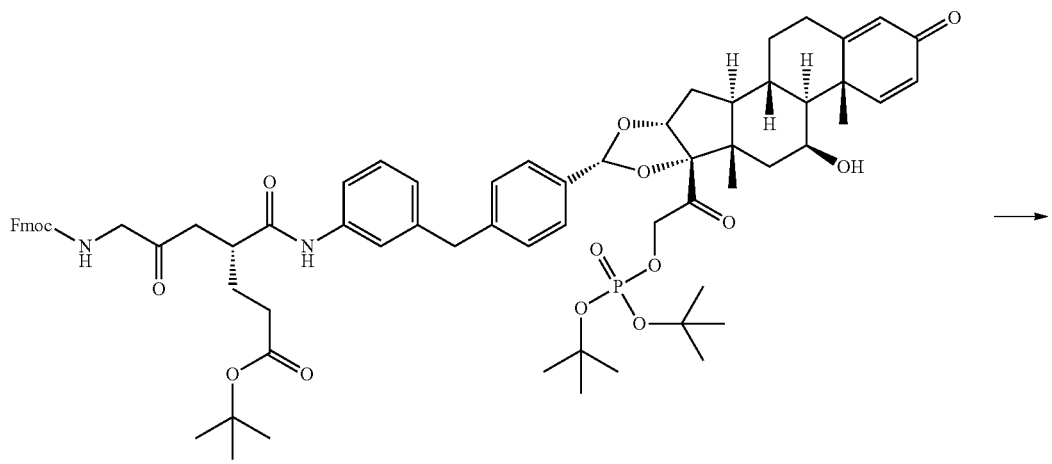

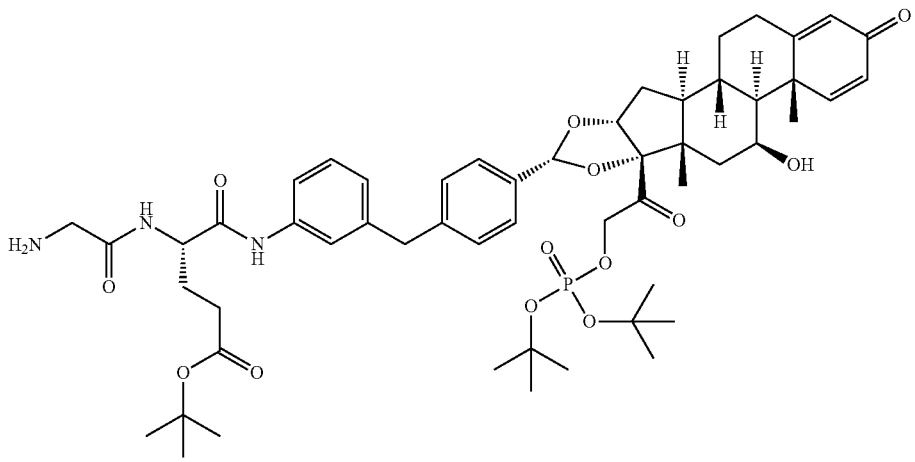

To a solution of tert-butyl (S)-4-(2-((((9H-fluoren-9-yl)methoxy)carbonyl)amino)acetamido)-5-((3-(4-((6aR,6bS,7S,8aS,8bS,10R,11aR,12aS,12bS)-8b-(2-((di-tert-butoxyphosphoryl)oxy)acetyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-5-oxopentanoate (Example 4, Step 3) (1.1 g, 0.897 mmol) in MeCN (6 mL) was added piperidine (0.75 mL, 7.58 mmol) at 25° C. The reaction was stirred at rt for 20 minutes after which time LCMS showed the reaction was complete. Three additional vials were set up as described above. All four reaction mixtures were combined. The mixture was concentrated to afford a residue, which was treated with PE (10 mL) under stirring for 2 hours. The resulting solid was collected by filtration, and dried under reduced pressure to afford the title compound (3.8 g, yield 90%) as a yellow solid.

LCMS (Method a, Table 4) $R_t$=1.16 min; m/z 1004.6 (M+H)$^+$.

Step 5: Synthesis of tert-butyl (S)-4-(2-(2-bromoacetamido)acetamido)-5-((3-(4-((6aR,6bS,7S,8aS,8bS,10R,11aR,12aS,12bS)-8b-(2-((di-tert-butoxyphosphoryl)oxy)acetyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-5-oxopentanoate

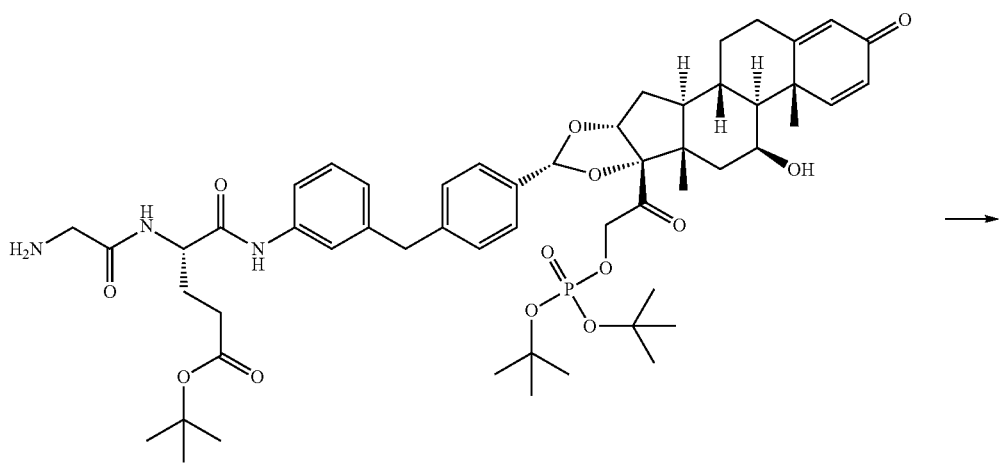

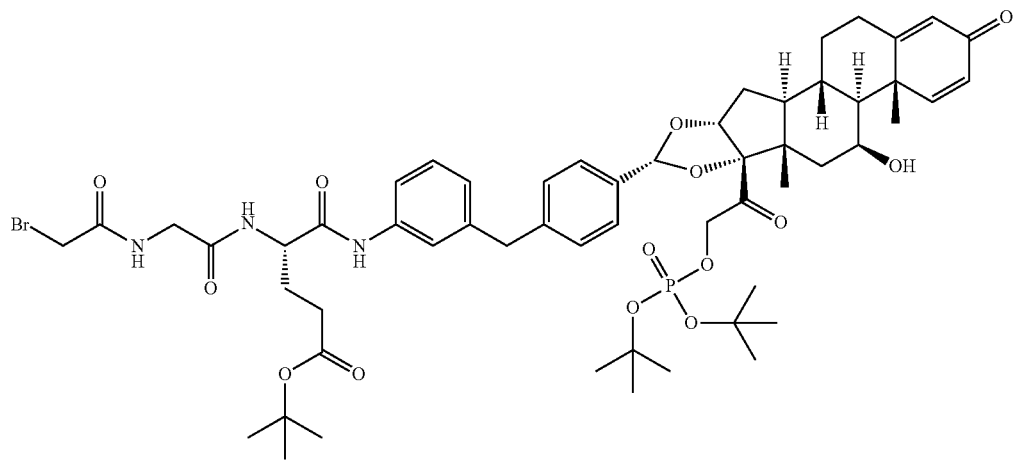

To a solution of 2-bromoacetic acid (97 mg, 0.697 mmol) in DMF (2.5 mL) was added EEDQ (172 mg, 0.697 mmol) at rt. The mixture was stirred at rt for 1 hour. tert-Butyl (S)-4-(2-aminoacetamido)-5-((3-(4-((6aR,6bS,7S,8aS,8bS,10R,11aR,12aS,12bS )-8b-(2-((di-tert-butoxyphosphoryl)oxy)acetyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-5-oxopentanoate (Example 4, Step 4) (350 mg, 0.349 mmol) was added and the resulting solution was stirred for 2.5 hours after which time LCMS showed the reaction was complete. Seven additional vials were set up as described above. All eight reaction mixtures were combined. The reaction was diluted with DCM (100 mL), washed with aqueous HBr (1 M, 2×80 mL), aqueous NaHCO$_3$ (60 mL), and brine (60 mL). The organic layer was dried over Na$_2$SO$_4$, filtered and concentrated under reduced pressure to afford the title compound (2 g, yield 63.7%) as yellow oil.

LCMS (Method a, Table 4) R$_t$=1.30 min; m/z 1124.2, 1125.9 (M+H)$^+$.

Step 6: Synthesis of (S)-4-(2-(2-bromoacetamido)acetamido)-5-((3-(4-((6aR,6bS,7S,8aS,8bS,10R,11aR,12aS,12S)-7-hydroxy-6a,8a-dimethyl-4-oxo-8b-(2-(phosphonooxy)acetyl)-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-5-oxopentanoic acid

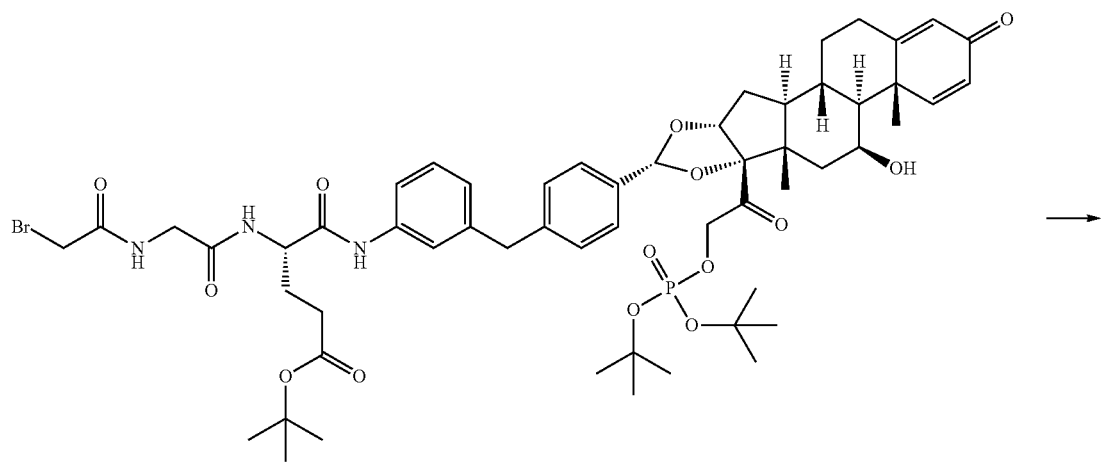

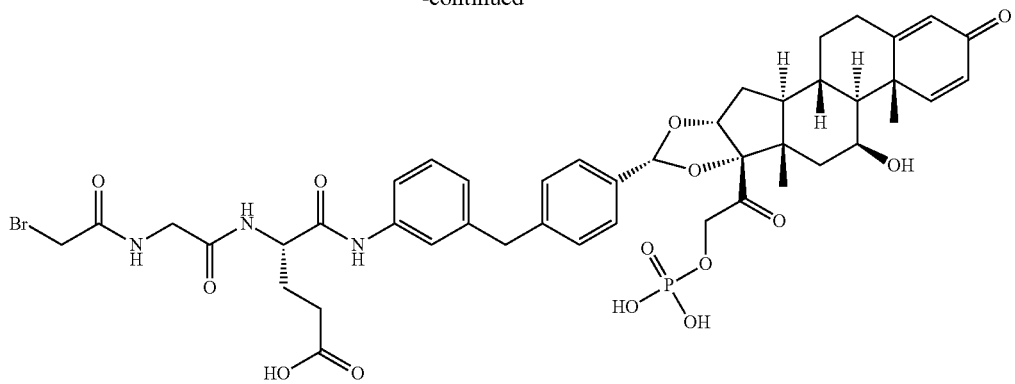

To a solution of tert-butyl (S)-4-(2-(2-bromoacetamido)acetamido)-5-((3-(4-(((6aR,6bS,7S,8aS,8bS,10R,11aR,12aS,12bS)-8b-(2-((di-tert-butoxyphosphoryl)oxy)acetyl)-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-5-oxopentanoate (Example 4, Step 5) (2 g, 1.778 mmol) in DCM (16 mL) was added TFA (8 mL, 104 mmol) and the resulting mixture was stirred at rt for 40 minutes after which time LCMS showed the reaction was complete. The solvent was removed under reduced pressure. The resulting residue was purified by Prep HPLC. The mobile phase was lyophilized directly to afford the title compound (640 mg, yield 35.3%) as yellow solid. Prep HPLC method: Instrument: Shimadzu LC-8A preparative HPLC; Column: Phenomenex Luna C18 200*40 mm*10 μm; Mobile phase: A for H₂O (0.09% TFA) and B for MeCN; Gradient: B from 30% to 40% in 20 min; Flow rate: 60 mL/min; Wavelength: 220 & 254 nm.

¹H NMR: (DMSO-d6, 400 MHz) δ=9.88 (s, 1H), 8.52 (s, 1H), 8.24 (br d, J=8.4 Hz, 1H), 7.46 (br d, J=7.9 Hz, 1H), 7.42 (s, 1H), 7.36 (br d, J=7.9 Hz, 2H), 7.30 (br d, J=9.7 Hz, 1H), 7.23-7.17 (m, 3H), 6.90 (br d, J=6.8 Hz, 1H), 6.16 (br d, J=10.4 Hz, 1H), 5.93 (s, 1H), 5.47 (s, 1H), 4.96-4.85 (m, 3H), 4.58 (br dd, J=7.9, 18.7 Hz, 1H), 4.38 (br d, J=5.3 Hz, 1H), 4.29 (br s, 1H), 3.93 (s, 2H), 3.89 (s, 2H), 3.80 (br s, 2H), 2.30-2.22 (m, 2H), 2.16-1.91 (m, 4H), 1.85-1.62 (m, 6H), 1.39 (s, 3H), 1.00 (br s, 2H), 0.87 (s, 3H). LCMS (Method a, Table 4) $R_t$=2.86 min; m/z 956.0, 958.0 (M+H)⁺.

Example 5

Synthesis of 2-(2S,6aS,6bR,7S,8aS,8bS,10R,11aR,12aS,12bS)-10-(4-(3-((S)-6-amino-2-(2-(2-bromoacetamido)acetamido)hexanamido)benzyl)phenyl)-2,6b-difluoro-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethyl dihydrogen phosphate.

Step 1: Synthesis of tert-butyl ((S)-5-(2-((((9H-fluoren-9-yl)methoxy)carbonyl)amino)acetamido)-6-((3-(4-((2S,6aS,6bR,7S,8aS,8bS,10R,11aR,12aS,12S)-2,6b-difluoro-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-6-oxohexyl)carbamate

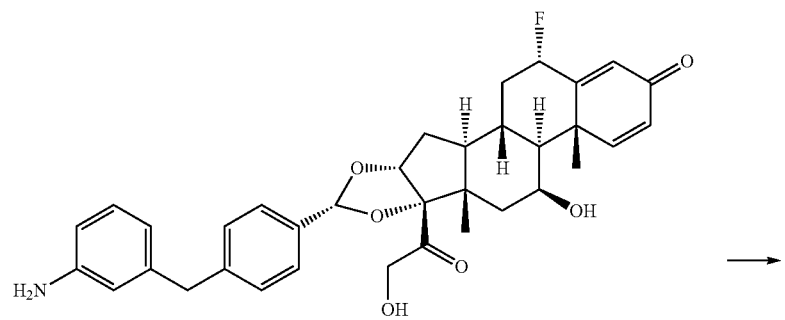

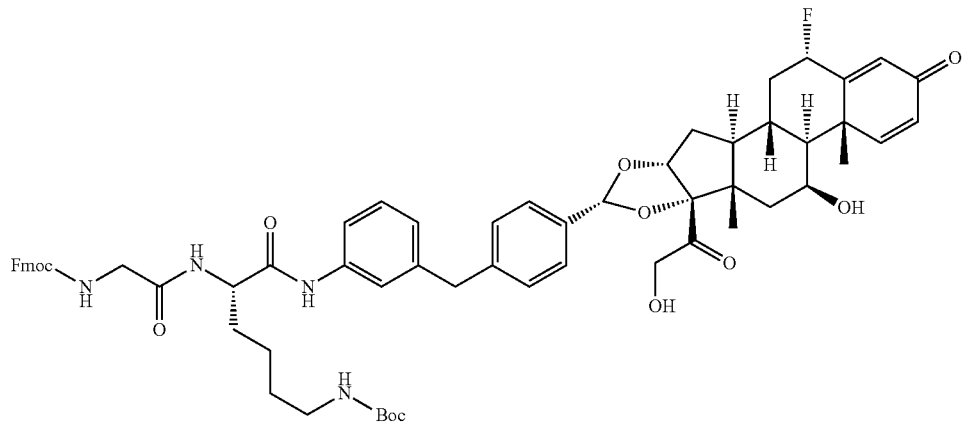

To a solution of N²-((((9H-fluoren-9-yl)methoxy)carbonyl)glycyl)-N6-(tert-butoxycarbonyl)-L-lysine (5.58 g, 8.26 mmol) in DMF (60 mL) at 0° C. was added 2,4,6-tripropyl-1,3,5,2,4,6-trioxatriphosphinane 2,4,6-trioxide (10.51 g, 16.51 mmol) and triethylamine (3.45 mL, 24.77 mmol). The resulting mixture was stirred at rt for 1 hour (2S,6aS,6bR,7S,8aS,8bS,10R,11aR,12aS,12bS)-10-(4-(3-aminobenzyl)phenyl)-2,6b-difluoro-7-hydroxy-8b-(2-hydroxyacetyl)-6a,8a-dimethyl-1,2,6a,6b,7,8,8a,8b,11a,12,12a,12b-dodecahydro-4H-naphtho[2',1':4,5]indeno[1,2-d][1,3]dioxol-4-one (Example 1, Step 6) (5 g, 8.26 mmol) was added. The resulting mixture was stirred for 5 hours at rt after which time LCMS showed the reaction was complete. Six additional vials were set up as described above. All seven reaction mixtures were combined. The reaction was purified by reverse phase column to afford the title compound (24 g, yield 24.62%) as a white solid. Reverse phase column method: Instrument: Shimadzu LC-8A prep HPLC; Column: Phenomenex Luna C18 200*40 mm*10 µm; Mobile phase: A for H₂O (0.05% TFA) and B for MeCN; Gradient: B from 30% to 100% in 30 min; Flow rate: 60 mL/min; Wavelength: 220 & 254 nm.

LCMS (Method a, Table 4) R$_f$=1.29 min; m/z 1095.6 (M+H−18)⁺.

Step 2: Synthesis of tert-butyl ((S)-5-(2-((((9H-fluoren-9-yl)methoxy)carbonyl)amino)acetamido)-6-((3-(4-((2S,6aS,6bR,7S,8aS,8bS,10R,11aR,12aS,12S)-8b-(2-((di-tert-butoxyphosphoryl)oxy)acetyl)-2,6b-difluoro-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-6-oxohexyl)carbamate

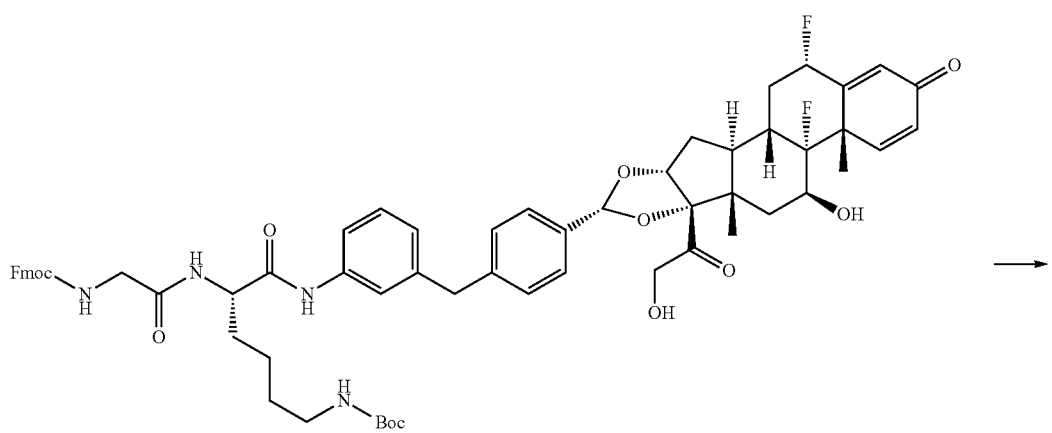

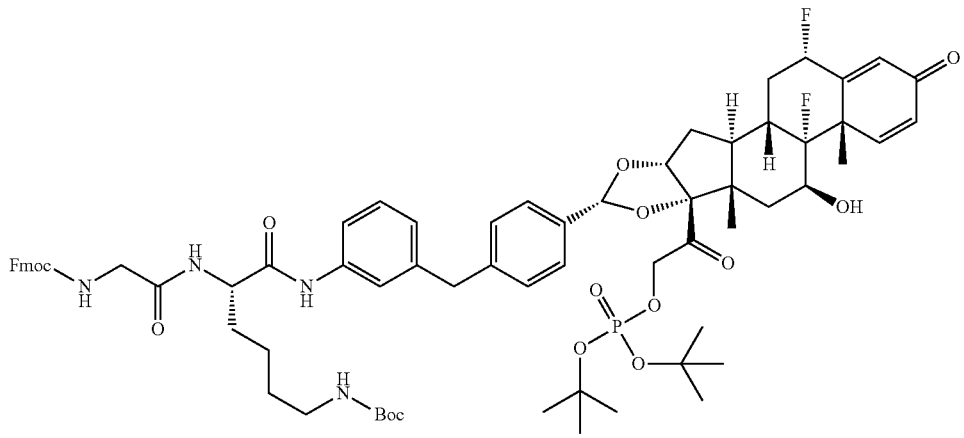

To a solution of tert-butyl ((S)-5-(2-((((9H-fluoren-9-yl)methoxy)carbonyl)amino)acetamido)-6-((3-(4-((2S,6aS,6bR,7S,8aS,8bS,10R,11aR,12aS,12bS)-2,6b-difluoro-7-hydroxy-8b-(2-hydroxyacetyl)-6a,8a-dimethyl-4-oxo-2,4,6a,6b,7,8,8a,8b,11 a,12,12a,12b-dodecahydro-1H-naphtho[2',1':4,5]indeno[1,2-d][1,3]dioxol-10-yl)benzyl)phenyl)amino)-6-oxohexyl)carbamate (Example 5, Step 1) (3 g, 2.69 mmol) in DMF (30 mL) was added 1H-tetrazole (1.888 g, 26.9 mmol) and di-tert-butyl diethylphosphoramidite (8.06 g, 32.3 mmol) and the reaction was stirred at rt for 3.5 hours. Hydrogen peroxide (224 mg, 1.97 mmol) was added to the reaction and stirred for 0.5 hours after which time LCMS showed the reaction was complete. Six additional vials were set up as described above. All seven reaction mixtures were combined. The reaction was purified by reverse phase column to afford the title compound (10 g, purity: 78%, yield 37.1%) as a white solid. Reverse phase column method: Instrument: Shimadzu LC-8A prep HPLC; Column: Phenomenex Luna C18 200*40mm*10 μm; Mobile phase: A for $H_2O$ and B for MeCN; Gradient: B from 50% to 100% in 30 min; Flow rate: 60 mL/min; Wavelength: 220 & 254 nm.

LCMS (Method a, Table 4) $R_f$=1.42 min; m/z 1305.7 $(M+H)^+$.

Step 3: Synthesis of tert-butyl ((S)-5-(2-aminoacetamido)-6-((3-(4-((2S,6aS,6bR,7S,8aS,8bS,10R,11aR,12aS,12bS)-8b-(2-((di-tert-butoxyphosphoryl)oxy)acetyl)-2,6b-difluoro-7-hydroxy-6a,8a-dimethyl-4-oxo-2,4,6a,6b,7,8,8a,8b,11 a,12,12a,12b-dodecahydro-1H-naphtho[2',1':4,5]indeno [1,2-d][1,3] dioxol-10-yl)benzyl)phenyl)amino)-6-oxohexyl)carbamate

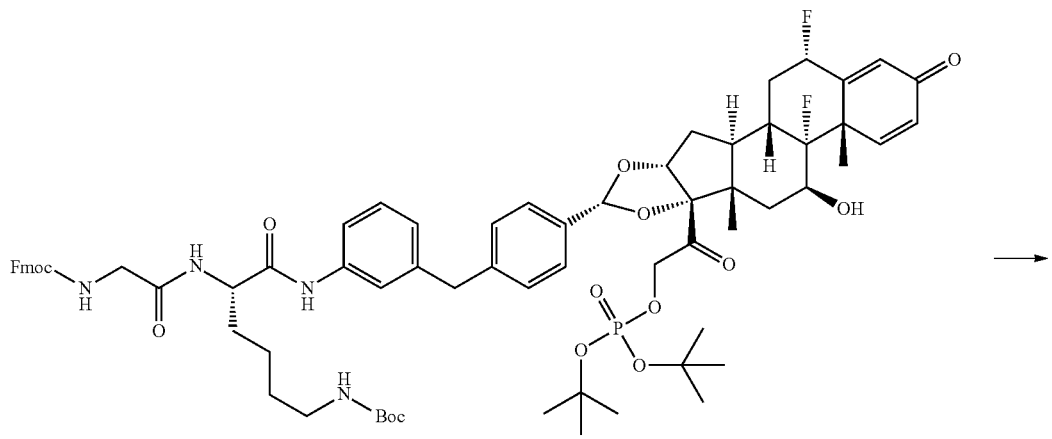

-continued

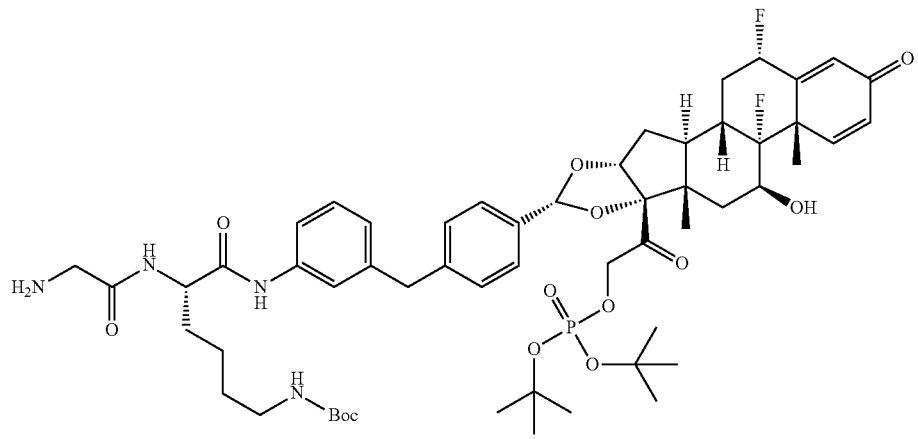

To a solution of tert-butyl ((S)-5-(2-((((9H-fluoren-9-yl)methoxy)carbonyl)amino)acetamido)-6-((3-(4-((2S,6aS,6bR,7S,8aS,8bS,10R,11aR,12aS,12bS)-8b-(2-((di-tert-butoxyphosphoryl)oxy)acetyl)-2,6b-difluoro-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-6-oxohexyl)carbamate (Example 5, Step 2) (2.5 g, 1.969 mmol) in MeCN (10 mL) was added piperidine (2 mL, 1.969 mmol) and the reaction stirred at rt for 1 hour after which time LCMS showed the reaction was complete. Three additional vials were set up as described above. All four reaction mixtures were combined. The reaction was concentrated to afford a crude product, which was stirred in PE (30 mL) for 2 hours. The resulting solid was collected by filtration, and dried under reduced pressure to afford the title compound (7 g, purity: 83%, yield 70.4%) as a yellow solid.

LCMS (Method a, Table 4) $R_t$=1.17 min; m/z 1083.5 (M+H)$^+$.

Step 4: Synthesis of tert-butyl ((S)-5-(2-(2-bromoacetamido)acetamido)-6-((3-(4-((2S,6aS,6bR,7S,8aS,8bS,10R,11aR,12aS,12bS)-8b-(2-((di-tert-butoxyphosphoryl)oxy)acetyl)-2,6b-difluoro-7-hydroxy-6a,8a-dimethyl-4-oxo-2,4,6a,6b,7,8,8a,8b,11a,12,12a,12b-dodecahydro-1H-naphtho[2',1':4,5]indeno [1,2-d][1,3] dioxol-10-yl)benzyl)phenyl)amino)-6-oxohexyl)carbamate

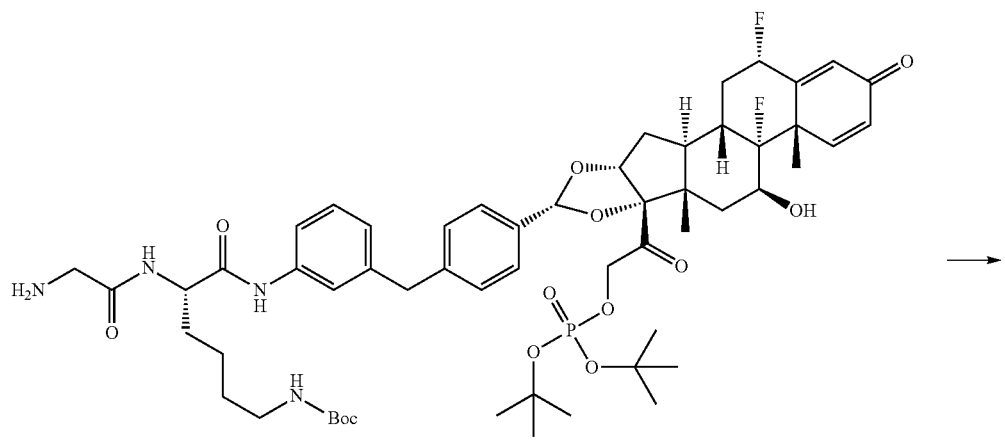

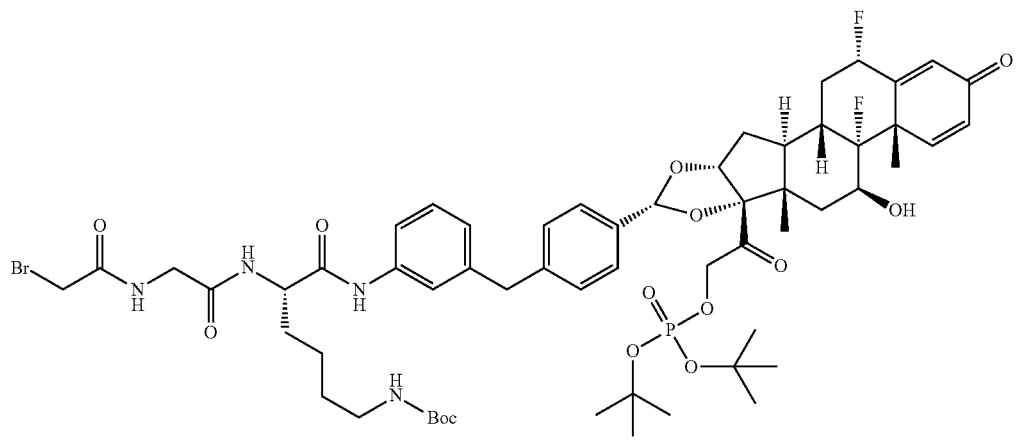

To a solution of 2-bromoacetic acid (0.929 g, 6.68 mmol) in DMF (35 mL) was added 2-ethoxy-1-ethoxycarbonyl-1,2-dihydroquinoline (1.653 g, 6.68 mmol) and the resulting mixture stirred at rt for 1 hour. The product from Example 5, Step 3 (3.5 g, 3.34 mmol) was added and the resulting mixture stirred at rt for 2 hours. LCMS showed the reaction was completed. The reaction was diluted with DCM (100 mL), washed with aqueous HBr (1 M, 2×80 mL), aqueous NaHCO$_3$ (60 mL) and brine (60 mL). The organic layer was dried over Na$_2$SO$_4$, filtered and concentrated under reduced pressure to afford the title compound (2 g, yield 51.2%) as yellow oil.

LCMS (Method a, Table 4) R$_t$=1.32 min; m/z 1205.5 (M+H)$^+$.

Step 5: Synthesis of 2-((2S,6aS,6bR,7S,8aS,8bS,10R,11aR,12aS,12S)-10-(4-(3-(S)-6-amino-2-(2-(2-bromoacetamido)acetamido)hexanamido)benzyl)phenyl)-2,6b-difluoro-7-hydroxy-6a,8a-dimethyl-4-oxo-1,2,4,6a,6b,7,8,8a,11a,12,12a,12b-dodecahydro-8bH-naphtho[2',1':4,5]indeno[1,2-d][1,3]dioxol-8b-yl)-2-oxoethyl dihydrogen phosphate

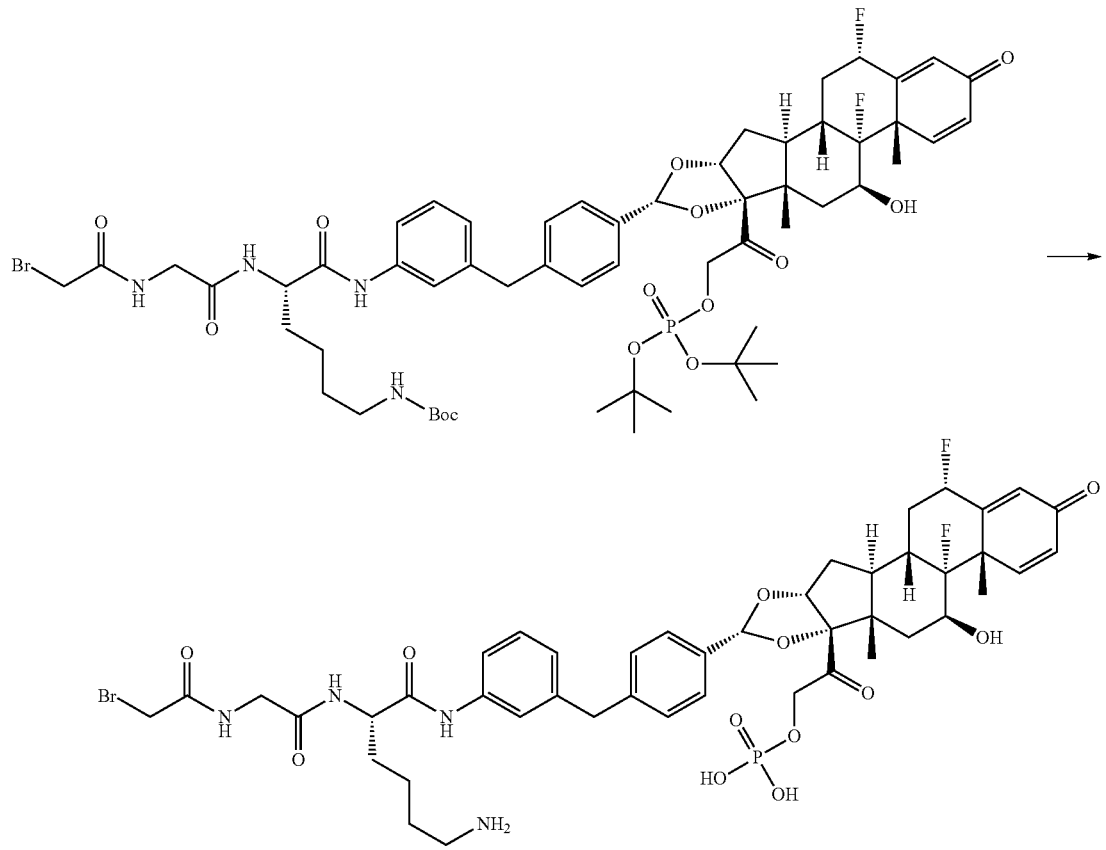

To a solution of tert-butyl ((S)-5-(2-aminoacetamido)-6-((3-(4-((2S,6aS,6bR,7S,8aS,8bS,10R,11aR,12aS,12S)-8b-(2-((di-tert-butoxyphosphoryl)oxy)acetyl)-2,6b-difluoro-7-hydroxy-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-6-oxohexyl)carbamate (Example 5, Step 3) (2 g, 1.661 mmol) in DCM (10 mL) was added TFA (5 mL, 64.9 mmol) and the reaction stirred at rt for 40 min after which time LCMS showed the reaction was complete. The solvent was removed under reduced pressure and the crude product purified by Prep HPLC. The mobile phase was lyophilized directly to afford the title compound (550 mg, purity: 96.9%, yield 32.3%) as an off-white solid. Prep-HPLC method: Instrument: Shimadzu LC-8A prep HPLC; Column: Phenomenex Luna C18 200*40 mm*10 μm; Mobile phase: A for $H_2O$ (0.09% TFA) and B for MeCN; Gradient: B from 30% to 40% in 20 min; Flow rate: 60 mL/min; Wavelength: 220 & 254 nm.

$^1$H NMR: (DMSO-d6, 400 MHz) δ ppm 0.90 (s, 3 H) 1.19-1.41 (m, 2 H) 1.43-1.62 (m, 7 H) 1.64-1.77 (m, 3 H) 1.84 (br d, J=14.55 Hz, 1 H) 1.95-2.07 (m, 1 H) 2.18-2.36 (m, 3 H) 2.65-2.78 (m, 3 H) 3.71-3.86 (m, 3 H) 3.89 (s, 2 H) 3.93 (s, 2 H) 4.20 (br d, J=9.48 Hz, 1 H) 4.33-4.41 (m, 1 H) 4.59 (br dd, J=18.41, 8.05 Hz, 1 H) 4.81 (br dd, J=18.52, 8.60 Hz, 1 H) 4.94 (d, J=4.63 Hz, 1 H) 5.50 (s, 1 H) 5.54-5.76 (m, 1 H) 6.13 (s, 1 H) 6.29 (dd, J=10.14, 1.32 Hz, 1 H) 6.95 (d, J=7.72 Hz, 1 H) 7.15-7.28 (m, 4 H) 7.30-7.41 (m, 3 H) 7.51 (br d, J=7.94 Hz, 1 H) 7.72 (br s, 3 H) 8.21 (br d, J=7.72 Hz, 1 H) 8.54 (t, J=5.62 Hz, 1 H) 9.93 (br d, J=2.65 Hz, 1 H) LCMS (Method a, Table 4) $R_t$=2.31 min.

Example 6

Synthesis of (S)-2-((2-(2-bromoacetamido)ethyl)amino)-N-((S)-1-((3-(4-((6aR,6bS,7S,8aS,8bS,10R,11aR,12aS,12bS)-7-hydroxy-8b-(2-hydroxyacetyl)-6a,8a-dimethyl-4-oxo-2,4,6a,6b,7,8,8a,8b,11a,12,12a,12b-dodecahydro-1H-naphtho[2',1':4,5]indeno[1,2-d][1,3]dioxol-10-yl)benzyl)phenyl)amino)-1-oxopropan-2-yl)propanamide.

Example 6 product may be synthesized from coupling of N-(2-((((9H-fluoren-9-yl)methoxy)carbonyl)amino)ethyl)-N-(tert-butoxycarbonyl)-L-alanyl-L-alanine (the product of steps S1 and S2 below) to the amino product of Example 2, followed by steps S4-S6: (1) Fmoc deprotection, (2) coupling with 2-bromoacetic acid, and (3) Boc deprotection. Fmoc=Fluorenylmethyloxycarbonyl; Boc=tertbutoxycarbonyl.

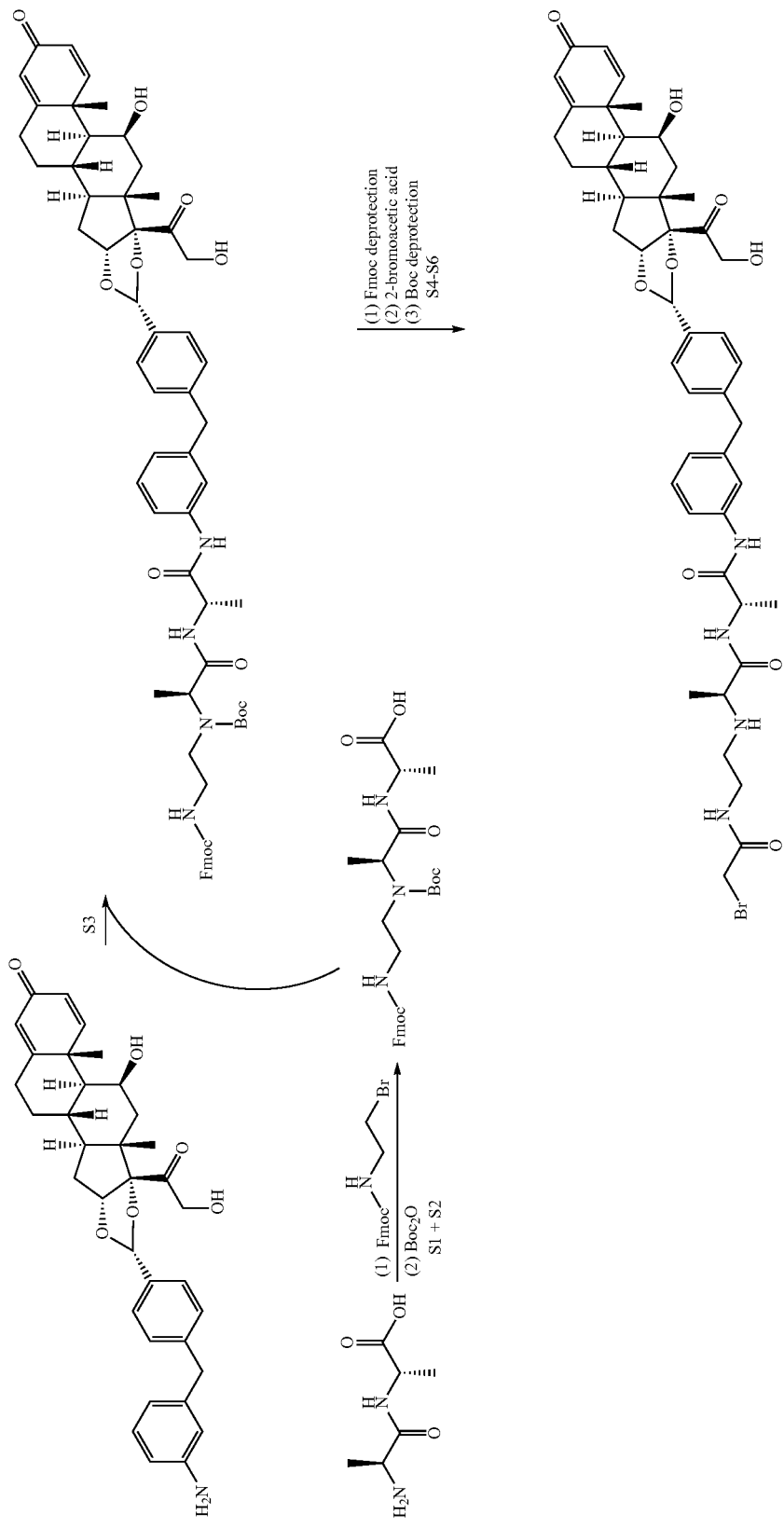

General Cysteine Conjugation Protocol

An approximate 5-20 mg/mL solution of the desired antibody was prepared in PBS buffer, pH 6 -7.4. A reducing agent of choice, such as TCEP, was diluted or dissolved in solvents like $H_2O$, DMSO, DMA or DMF to give a solution with concentration range between 1 to 25 mM. Antibodies (anti-hTNF hIgG1 (D2E7) or anti-mTNF mIgG2a (8C11; McRae B L et al. *J Crohns Colitis* 10 (1): 69-76 (2016)) were then partially reduced by adding about 2-3.5 equivalents of reducing agent, briefly mixing, and incubating overnight at 0-4° C. Tris buffer, pH 8-8.5 (20-50 mM) was then added, followed by the linker-drug in DMSO or DMA (less than 15% total) and the mixture was incubated for 2-3 hours at rt. Excess linker-drug and organic solvent were then removed by purification. Purified ADC samples were then analyzed by SEC, HIC and reduced mass spectrometry.

ADC Analytical Procedures

ADCs were profiled by either anionic exchange chromatography (AEC) or hydrophobic interaction chromatography (HIC) to determine the degree of conjugation and purity of ADC.

AEC. Approximately 20 μg of ADC was loaded onto an Ultimate 3000 Dual LC system (Thermo Scientific) equipped with a 4×250 mm Propac™ WAX-10 column (Tosoh Bioscience, cat. 054999). Column was equilibrated with 100% buffer A and eluted using a linear gradient from 100% buffer A to 100% buffer B over 18 min at 1.0 mL/min, where buffer A is 20 mM MES, pH 6.7 and buffer B is 20 mM MES, 500 sodium chloride, pH 6.7.

HIC. Approximately 20 μg of the ADC was loaded onto an Ultimate 3000 Dual LC system (Thermo Scientific) equipped with a 4.6×35 mm butyl-NPR column (Tosoh Bioscience, cat. 14947). Column was equilibrated in 100% buffer A and eluted using a linear gradient from 100% buffer A to 100% buffer B over 12 min at 0.8 mL/min, where buffer A is 25 mM sodium phosphate, 1.5 M ammonium sulfate, pH 7.0 and buffer B is 25 mM sodium phosphate, 25% isopropanol, pH 7.0.

SEC. Size distributions of the ADCs were profiled by size exclusion SEC using an Ultimate 3000 Dual LC system (Thermo Scientific) equipped with a 7.8×300 mm TSK-gel $3000SW_{XL}$ column (Tosoh Bioscience, cat. 08541). Approximately 20 μg of ADC was loaded onto the column and eluted over 17 min using an isocratic gradient of 100 mM sodium sulfate, 100 mM sodium phosphate, pH 6.8 at a flow rate of 1.0 mL/min.

MS. Reduced samples (10 μL) were injected to an Agilent 6550 QT of LC/MS system through a temperature controlled (5° C.) CTC autosampler. Sample elution was achieved on a Waters C-4, 3.5 μm, 300 Å, 2.1×50 mm i.d. HPLC column. The mobile phases were: A: 0.1% formic acid in water, and B: 0.1% formic acid in MeCN; the flow rate was 0.45 mL/min, and the column compartment was maintained at 40° C.

The HPLC gradient is as set forth in Table 5:

TABLE 5

| Time (min) | % A | % B |
|---|---|---|
| 0 | 95 | 5 |
| 0.6 | 95 | 5 |
| 1.1 | 10 | 90 |
| 2.2 | 10 | 90 |
| 2.4 | 95 | 5 |
| 3.5 | 95 | 5 |

Example 7

Preparation of Adalimumab Conjugated with a Glucocorticosteroid to Provide an Antibody Drug Conjugate Adalimumab BrAc-Gly-Glu-Steroid-$PO_4$ ADC having a population DAR 4.0 was prepared by a two-step chemical process: disulfide reduction of adalimumab followed by alkylation (conjugation) with bromoacetamido glycine-glutamic acid steroid Example 4.

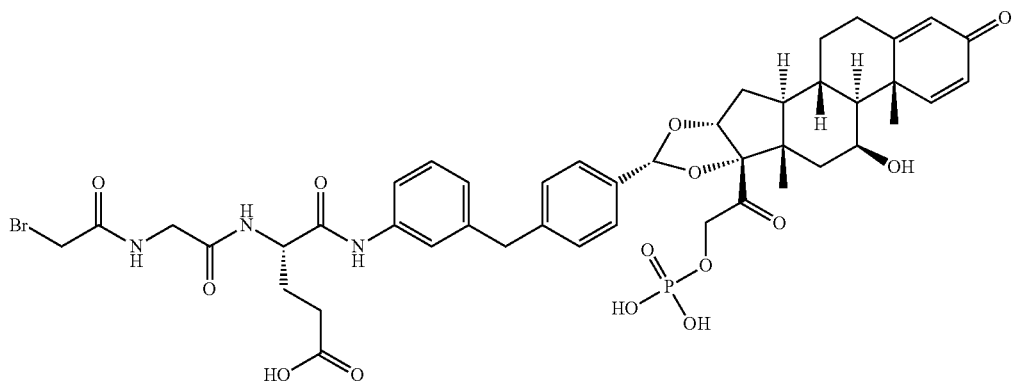

100 mg of adalimumab at a concentration of 20 mg/mL were reduced with diphenylphosphinoacetic acid (2.9-3.0 eq) at 0° C. overnight. Partially-reduced adalimumab was then conjugated to Example 4 (10 eq) in DMSO for 3 hours at rt. The conjugation mixture was first buffer exchanged into 20 mM Tris Buffer, 50 mM NaCl, pH 7.8 using multiple NAP 25 desalting columns. The desalted ADC solution was purified by AEC to afford the DAR4 components of the ADC. AEC chromatography method: Instrument: Akta pure; Column: 2X Hitrap Q HP 5 mL; Mobile phase: A for 20 mM Tris Buffer, pH 7.8; B for 20 mM Tris Buffer, 1 M NaCl, pH 7.8; Gradient: B from 0% to 25% in 60 min; Flow rate: 5 mL/min; Wavelength: 280 & 214 nm.

Referring to FIG. 1, which shows a chromatographic resolution of the resultant ADC preparation, the ADC is a heterogeneous mixture containing antibodies having two drug linker molecules attached ("DAR2" peak), four drug linker molecules attached ("DAR4" peak), depending upon the number of interchain disulfide bonds reduced. The AEC conditions used in FIG. 1 were as follows:

The column was Propac™ WAX-10, 4×250 mm (Thermo Fisher Scientific, cat. 054999) and the column temperature was 37° C. Wavelength was 280 nm, run time was 18 minutes, injection amount was 20 μg, and flow rate was 1.0 mL/minute. Mobile Phase A: 20 mM MES, pH 6.7, Mobile Phase B: 20 mM MES, 500 mM NaCl, pH 6.7. Gradient Profile (Table 6):

TABLE 6

| Time (min) | Mobile Phase A (%) | Mobile Phase B (%) |
| --- | --- | --- |
| 0 | 75 | 25 |
| 14 | 5 | 95 |

TABLE 6-continued

| Time (min) | Mobile Phase A (%) | Mobile Phase B (%) |
| --- | --- | --- |
| 16 | 0 | 100 |
| 18 | 0 | 100 |

Figure 2:
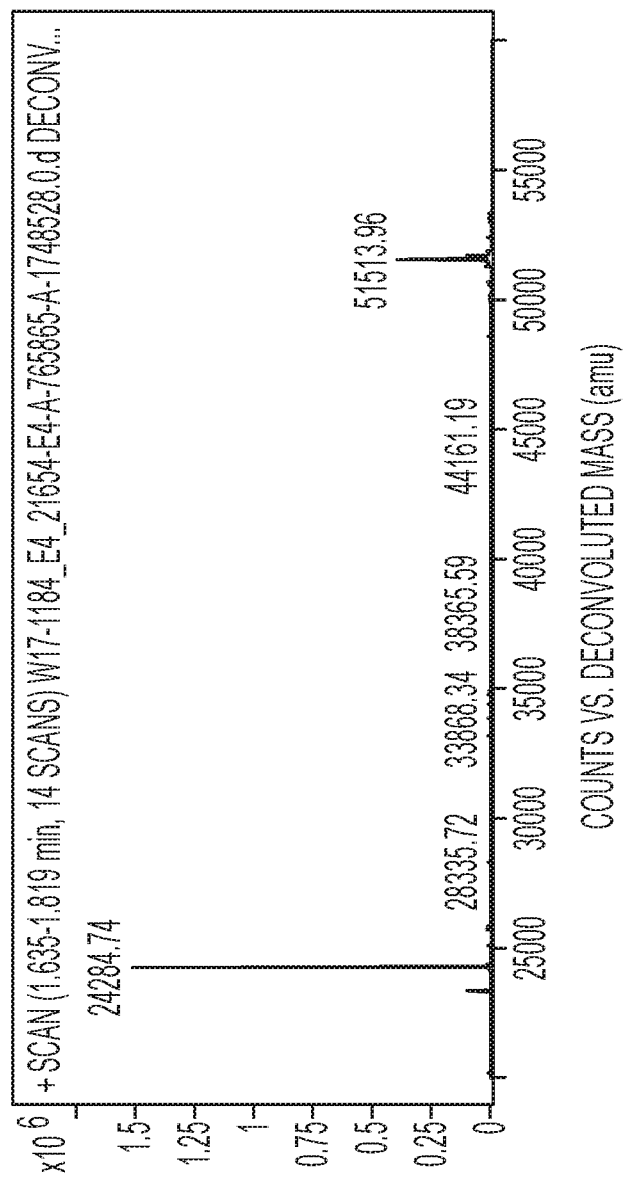
FIG. 2 sets forth deconvoluted MS data of adalimumab conjugated with BrAc-Gly-Glu-glucocorticosteroid-PO$_4$. As shown, conjugation was achieved.

FIG. 2 shows a deconvoluted mass spectrum of the purified ADC. This ADC has 4 drug linker molecules conjugated to each antibody. The peak on the left has molecular weight of 24284.74 Da, which is the result of one drug linker attached to single light chain. The peak on the right has molecular weight of 51513.96 Da, which is the result of one drug linker attached to single heavy chain. ADCs in Table 7 and 8 were prepared according to the procedure described above.

TABLE 7

Anti-mouse TNFa antibody drug conjugates. X refers to the anti-murine TNFa antibody 8C11

| ID NO. | Structure | DAR |
| --- | --- | --- |
| ADC1 | 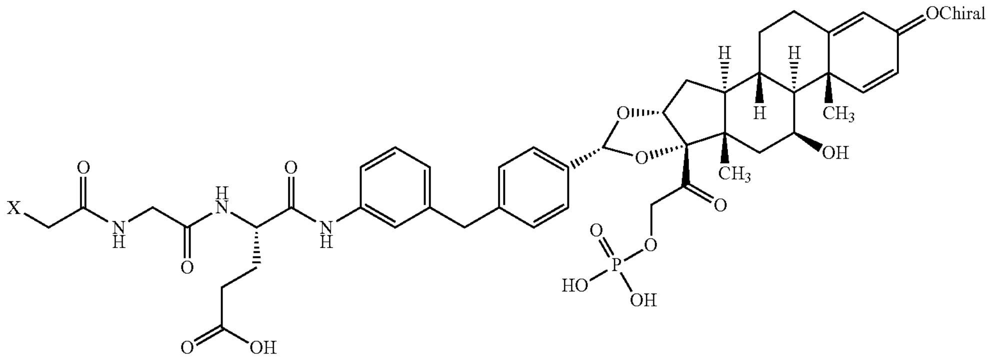 | 4 |
| ADC2 | 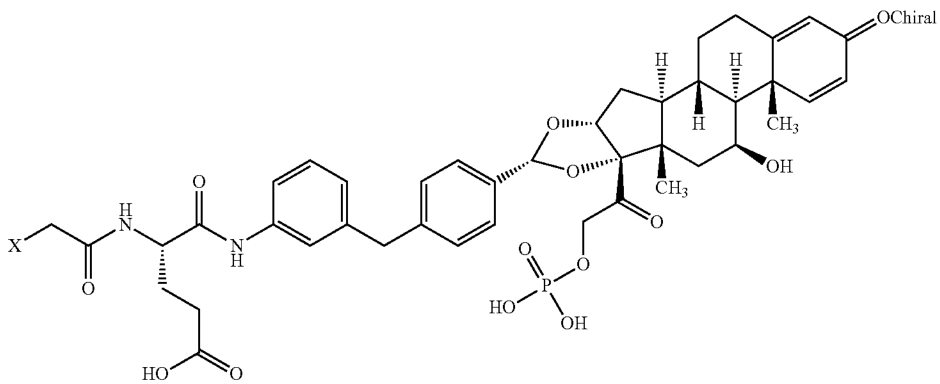 | 4 |
| ADC3 | 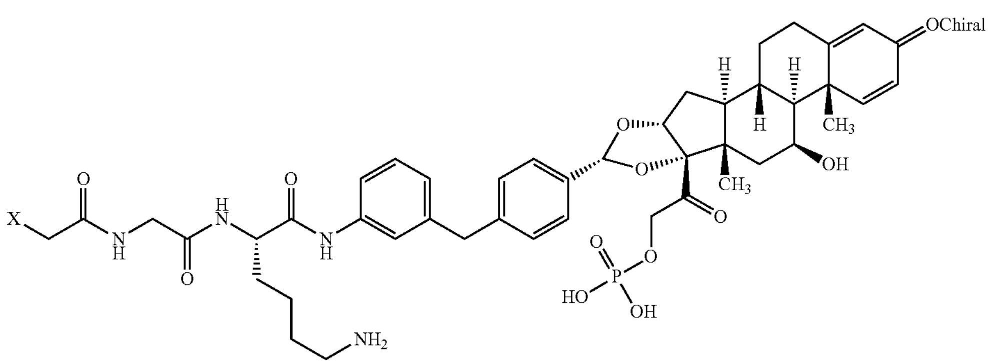 | 4 |

TABLE 8

Anti-human TNFa antibody drug conjugates. X refers to the anti-human TNFa antibody adalimumab

| Corporate ID | Structure | DAR |
|---|---|---|
| ADC4 | 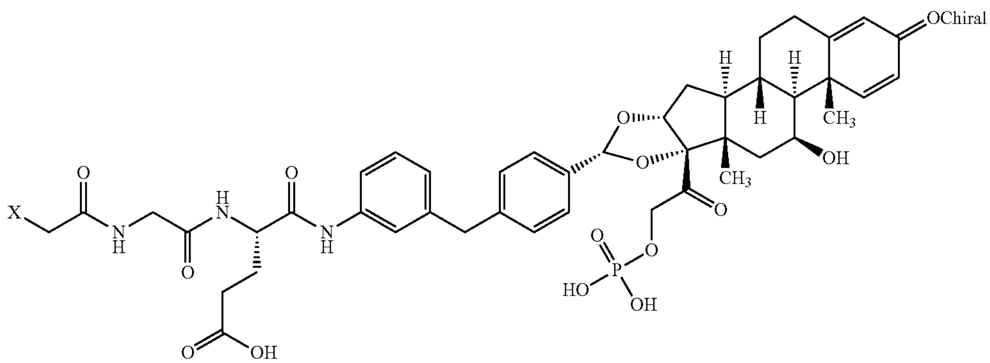 | 4 |
| ADC5 | 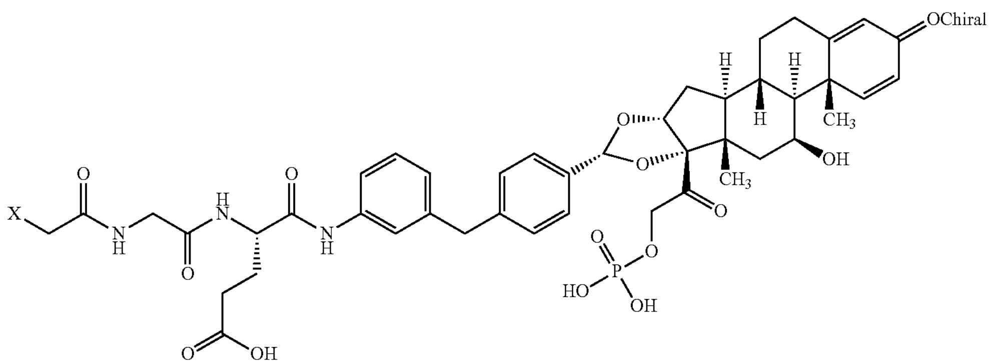 | 2 |
| ADC6 | 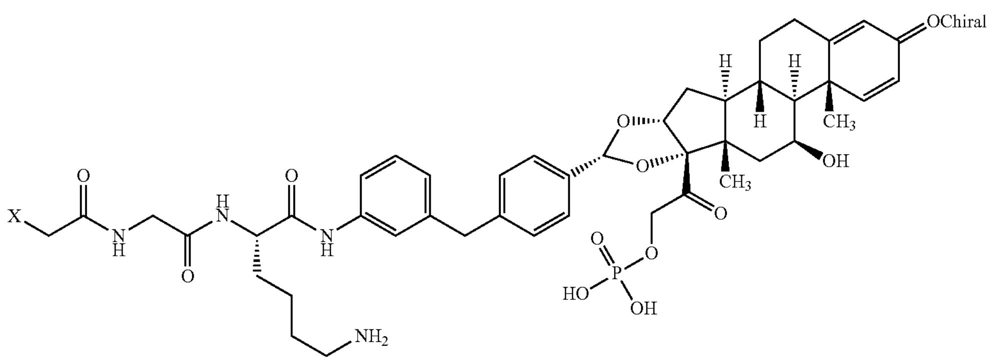 | 4 |

Generation of Human and Mouse Transmembrane TNF-Alpha GRE Reporter Cell Lines

In order to create a parental cell line, K562 cells were seeded onto a 6 well dish (Costar: 3516) with 2 mL of complete growth medium (RPMI, 10% FBS, 1% L-glutamine, 1% Na Pyruvate and 1% MEM NEAA) at 500,000 cells per well for 24 hours at 37°, 5% $CO_2$. The next day, 1.5 µg of pGL4.36[Luc2P/MMTV/Hygro] (Promega: E316), 1.5 ug pG14.75 [hRLuc/CMV] (Promega: E639A), and 3 uL of PLUS reagent (Invitrogen: 10964-021) were diluted into 244 µL Opti-MEM (Gibco: 31985-070) and incubated at rt for 15 minutes. The pGL4.36 [luc2P/MMTV/Hygro] vector contains MMTV LTR (Murine Mammary Tumor Virus Long Terminal Repeat) that drives the transcription of the luciferase reporter gene luc2P in response to activation of several nuclear receptors such as glucocorticoid receptor and androgen receptor. The pGL4.75[hRLuc/CMV] Vector encodes the luciferase reporter gene hRluc (*Renilla reniformis*) and is designed for high expression and reduced anomalous transcription.

After incubation, diluted DNA solution was pre-incubated with 1:1 Lipofectamine LTX solution (Invitogen: 94756) (13.2 µL+256.8 µL Opti-MEM) and incubated at room temperature for 25 minutes to form DNA-Lipofectamine LTX complexes. After incubation, 500 µL of DNA-Lipofectamine complexes were added directly to the well containing cells. K562 cells were transfected for 24 h at 37° C., 5% $CO_2$. After incubation, cells were washed with 3 mL of PBS and selected with complete growth medium containing 125 µg/mL of hygromycin B (Invitrogen: 10687-010) for two weeks. "K562 pGL4.36[Luc2P/MMTV/Hygro]_pGL4.75[hRLuc/CMV]" cells were produced.

In order to create a murine transmembrane TNF-alpha GRE reporter cell line, the parental cells, K562 pGL4.36

[Luc2P/MMTV/Hygro]_pGL4.75[hRLuc/CMV], were seeded onto 6 well dish (Costar: 3516) with 2 mL of complete growth medium (RPMI, 10% FBS, 1% L-glutamine, 1% Na Pyruvate and 1% MEM NEAA) at 500,000 cells per well for 24 h at 37°, 5% $CO_2$. The next day, 3 µg of mFL_TNFα DNA (Origene: MC208048), which encodes untagged mouse TNF, and 3 µL of PLUS reagent (Invitogen: 10964-021) were diluted into 244 µL Opti-MEM (Gibco: 31985-070) and incubated at rt for 15 minutes. After incubation, diluted DNA solution was pre-incubated with 1:1 Lipofectamine LTX solution (Invitogen: 94756) (13.2 µL+256.8 µL Opti-MEM) and incubated at rt for 25 minutes to form DNA-Lipofectamine LTX complexes. After incubation, 500 µL of DNA-Lipofectamine complexes were added directly to the well containing cells. The parental K562 pGL4.36[Luc2P/MMTV/Hygro]_pGL4.75[hRLuc/CMV] cells were transfected for 24 h at 37° C., 5% $CO_2$. After incubation, cells were washed with 3 mL of PBS and selected with complete growth medium containing 125 µg/mL of hygromycin B (Invitrogen: 10687-010) and 250 µg/mL G418 (Gibco: 10131-027) for two weeks. "K562 mouse FL-TNFα GRE (pGL4.36[luc2P/MMTV/Hygro])" cells were produced.

In order to create a human transmembrane TNF-alpha GRE reporter cell line, the parental cells, K562 pGL4.36 [Luc2P/MMTV/Hygro]_pGL4.75[hRLuc/CMV], were transfected with the plasmid hTNF delta 1-12 C-Myc pcDNA3.1(−) plasmid construct. This plasmid is pcDNA 3.1 (Thermofisher cat# V79020) encoding tace resistant transmembrane TNF (i.e., SEQ ID NO:1 lacking amino acids 77-88). (See Perez C et al. *Cell* 63 (2): 251-8 (1990) discussing tace resistant transmembrane TNF.) These cell lines were then used in the TNF-alpha reporter assays described in the subsequent examples.

Activity of Anti-TNF-Alpha Immunoconjugates in GRE Transmembrane TNF-Alpha Reporter Assays K562 parental GRE (pGL4.36[luc2P/MMTV/Hygro]) cells and K562 mFL-TNF-α or hTNF delta 1-12 GRE (pGL4.36[luc2P/MMTV/Hygro]) cells were plated onto 96 well tissue culture treated white plates (Costar: 3917) at 50,000 cells per well in 50 µL of assay medium (RPMI, 1% CSFBS, 1% L-glutamine, 1% Na Pyruvate and 1% MEAA). The cells were treated with 25 µL of 3X serial diluted murine or human anti-TNF-α antibody drug conjugates in assay medium, steroid compound, or media alone and incubated for 48 hours at 37° C., 5% $CO_2$. After 48 hours of incubation, cells were treated with 75 µL of Dual-Glo Luciferase Assay System (Promega-E2920) for 10 min and analyzed for luminescence using the Microbeta (PerkinElmer). Data were analyzed using a four parameter curve fit to generate $EC_{50}$ values. % maximum activation was normalized to 100 nM dexamethasone. The results using the murine TNF-alpha cell line are shown in Table 9 below, and the results using the human TNF-alpha cell line are shown in Table 10 below. In Table 9 below, the antibody in the ADC is the anti-murine TNFα antibody 8C11. In Table 10 below, the antibody in the ADC is the anti-human TNFα antibody adalimumab. Percent (%) monomer was determined by SEC as previously described (see ADC analytical procedures).

TABLE 9

In vitro activity of anti-murine TNFa antibody drug conjugate in mouse transmembrane TNFa GRE reporter assay

| ADC | % Monomer | mTNFa GRE $EC_{50}$ (µg/mL) | mTNFa GRE (% max) | K562 GRE $EC_{50}$ (µg/mL) | K562 GRE (% max) |
|---|---|---|---|---|---|
| ADC1 | 99.9 | 0.06 | 150 | >50 | 63 |
| ADC2 | 99.3 | 0.39 | 164 | >50 | 72 |
| ADC3 | 100 | 0.04 | 104 | 3.9 | 84 |

TABLE 10

In vitro activity of anti-human TNFa antibody drug conjugate in human transmembrane TNFa GRE reporter assay

| ADC | % Monomer | hTNFa GRE $EC_{50}$ (µg/mL) | hTNFa GRE (% max) | K562 GRE $EC_{50}$ (µg/mL) | K562 GRE (% max) |
|---|---|---|---|---|---|
| ADC4 | 99.9 | 0.03 | 118 | >50 | 63 |
| ADC5 | 100 | 0.03 | 126 | >50 | 28 |
| ADC6 | 100 | 0.05 | 97 | >50 | 83 |

Activity of Anti-hTNF Alpha Immunoconjugates in Lipopolysacharride Stimulated Human PBMC Cytokine Release Assay Primary human peripheral blood mononuclear cells (PBMCs) were purchased from Biological Specialty Corporation (cat# 214-00-10), washed in 50 mL PBS, re-suspended in FBS with 5% DMSO, aliquoted and cryopreserved in liquid nitrogen until use. The PBMCs were thawed, re-suspended in RPMI media supplemented with 2% FBS, and 1% Penicillin-Streptomycin, and plated into a cell assay plate (Costar #3799). Then the cells were incubated varying concentration of anti-TNF ADC at 37° C. and 5% $CO_2$ for 4 hours. Cells were then stimulated with 100 ng/mL LPS overnight. On the following day, plate was spun for five minutes at 1000 rpm, and 100 µL of supernatant media was directly transferred to an additional 96-well plate and analyzed for IL-6 (MSD, #K151AKB) and IL-1 beta(MSD, #K151AGB) concentrations. The dose response data were fitted to a sigmoidal curve using nonlinear regression, and the $IC_{50}$ values calculated with the aid of GraphPad 5.0 (GraphPad Software, Inc.). The results shown in Table 11 demonstrate that the anti-TNF ADC has potent activity in inhibiting the release of pro-inflammatory cytokines IL-6 and IL-1beta from activated primary immune cells.

TABLE 11

In vitro activity of anti-TNF steroid ADC in stimulated PBMC cytokine release assay

| ADC | IL-1 beta $IC_{50}$ (ng/mL) | IL-6 $IC_{50}$ (ng/ml) |
|---|---|---|
| ADC4 | 44 | 265 |

Activity of Anti-mTNF-Alpha Immunoconjugate in Contact Hypersensitivity Model

Anti-TNFα steroid ADC was evaluated in an acute contact hypersensitivity model, an elicitation of acute skin inflammation using delayed-type hypersensitivity (DTH) response (T-cell driven) via application of a sensitizing agent (fluorescein isothiocyanate (FITC)). The efficacy of anti-TNFα steroid ADCs was measured by the ability to reduce ear swelling. The steroid biomarkers corticosterone and procollagen type 1 N-terminal propeptide (P1NP) were included as readouts to assess the putative impact of anti-TNFa steroid ADC treatment on the Hypothalamus-Pituitary-Adrenal (HPA) axis and bone turnover respectively.

Ear Swelling

On day 0 mice were placed under general anesthesia and the abdomens were shaved. Using a micropipettor, mice were sensitized by epicutaneous application of 400 μL of FITC solution (1.5% solution in 1:1 acetone:DBP) on the abdomen. Six days later mice were dosed with vehicle or therapeutic agent 1 hour prior to ear challenge with FITC. For ear challenge, mice were placed under general anesthesia and were challenged with 20 μL FITC applied onto right ear. Twenty-four hours after challenge mice were placed under general anesthesia and their ear thickness is measured by caliper. Difference between challenged and unchallenged ears was calculated. Seventy-two hours after ear challenge, mice were injected with ACTH at 1 mpk IP, and terminally bled at 30 min post-ACTH. Plasma was collected and analyzed P1NP, corticosterone, free steroid, and large molecule levels.

Quantification of Released Free Steroid and Endogenous Corticosterone

Calibration curve of steroid was prepared in mouse plasma with final concentrations from 0.03 nM to 0.1 μM at 8 different concentration levels. Corticosterone calibration curve ranging from 0.3 nM to 1 μM final corticosterone concentrations was prepared in 70 mg/mL bovine serum albumin solution in PBS buffer. A solution of 160 μL MeCN with 0.1% formic acid was added to 40 μL study plasma samples or calibration standards. Supernatants were diluted with distilled water and 30 μL final sample solution was injected for LC/MS analysis.

Quantification of released free steroid and corticosterone was conducted on an AB Sciex 5500 triple quadruple mass spectrometer connected to a Shimadzu AC20 HPLC system interfaced with an electrospray ionization source operating in positive mode. A Waters XBridge BEH C18, 2.1×30 mm, 3.5 μm column was used for chromatography separation. The mobile phase A was 0.1% formic acid in Milli Q HPLC water, and mobile phase B was 0.1% formic acid in MeCN. A linear gradient from 2% of mobile phase B to 98% mobile phase B was applied from 0.6 to 1.2 min. The total run time was 2.6 min at a flow rate of 0.8 mL/min. The mass spectrometer was operated in positive MRM mode at source temperature of 700° C.

Quantification of Plasma P1NP

Quantification of plasma P1NP was conducted on a LCMS platform based on protein trypsin digestion. Plasma samples were partially precipitated and fully reduced by adding MeCN/0.1M ammonium bicarbonate/DTT mixture. Supernatant was collected and alkylated by adding iodoacetic acid. The alkylated proteins were digested by trypsin and resulting tryptic peptides were analyzed by LCMS. Calibration curve were generated by using synthetic tryptic peptide spiked into horse serum (non-interfering surrogate matrix). Stable isotope labeled flanking peptide (3-6 amino acids extension on both termini of the tryptic peptide) was used as internal standard added in the MeCN/DTT protein precipitation mixture to normalize both digestion efficiency and LCMS injection.

A Columnex Chromenta BB-C18, 2.1×150 mm, 5 μm column was used for chromatography separation. The mobile phase A was 0.1% formic acid in Milli Q HPLC water and mobile phase B was 0.1% formic acid in MeCN. A linear gradient from 2% of mobile phase B to 65% mobile phase B was applied from 0.6 to 3 min. The total run time was 8 min at a flow rate of 0.45 mL/min. An AB Sciex 4000Q trap mass spectrometer was used in positive MRM mode to quantify P1NP peptides, at source temperature of 700° C.

Results

The results are shown in Table 12 below:

TABLE 12

Comparison of anti-mTNF alpha steroid ADC activity on ear swelling and steroid biomarkers in CHS model of inflammation

| ADC | Ear swelling (% inhib @ 10 mpk ± SEM) | P1NP (% inhib. @ 10 mpk ± SEM) | Corticosterone (% inhib @ 10 mpk ± SEM) |
| --- | --- | --- | --- |
| ADC1 | 82.8 ± 2.3 | 32.6 ± 3.8 | 4.7 ± 10.5 |

Activity of Anti-mTNF-Alpha Immunoconjugates in Collagen-Induced Arthritis

The ability of anti-mTNFa steroid ADC (ADC1) to impact disease was assessed in the collagen-induced arthritis (CIA) model of arthritis.

In these experiments, male DBA/1J mice were obtained from Jackson Labs (Bar Harbor, Me.). Mice were used at 6 to 8 weeks of age. All animals were maintained at constant temperature and humidity under a 12 hour light/dark cycle and fed with rodent chow (Lab Diet 5010 PharmaServ, Framingham, Mass.) and water ad libitum. AbbVie is AAALAC (Association for Assessment and Accreditation of Laboratory Animal Care) accredited, and all procedures were approved by the Institutional Animal Care and Use Committee (IACUC) and monitored by an attending veterinarian. Body weight and condition were monitored, and animals were euthanized if exhibiting >20% weight loss.

The male DBA/J mice were immunized intradermally (i.d.) at the base of the tail with 100 μL of emulsion containing 100 μg of type II bovine collagen (MD Biosciences) dissolved in 0.1 N acetic acid and 200 μg of heat-inactivated Mycobacterium tuberculosis H37Ra (Complete Freund's Adjuvant, Difco, Laurence, Kans.). Twenty-one days after immunization with collagen, mice were boosted IP with 1 mg of Zymosan A (Sigma, St. Louis, Mo.) in PBS. Following the boost, mice were monitored 3 to 5 times per week for arthritis. Rear paws were evaluated for paw swelling using Dyer spring calipers (Dyer 310-115)

Mice were enrolled between days 24 and 28 at the first clinical signs of disease and distributed into groups of equivalent arthritic severity. Early therapeutic treatment began at the time of enrollment.

Animals were dosed once intraperitoneal (i.p.) with anti-mTNF mAb (high dose) or anti-mTNF steroid ADC (high and low dose—mpk) in 0.9% saline. Blood was collected for antibody exposure by tail nick at 24 and 72 hours after dose. Paws were collected at the terminal time-point for histopathology. Blood was collected at the terminal time-point by cardiac puncture for complete blood counts (Sysmex XT-2000iV). Statistical significance was determined by ANOVA.

Figure 3:
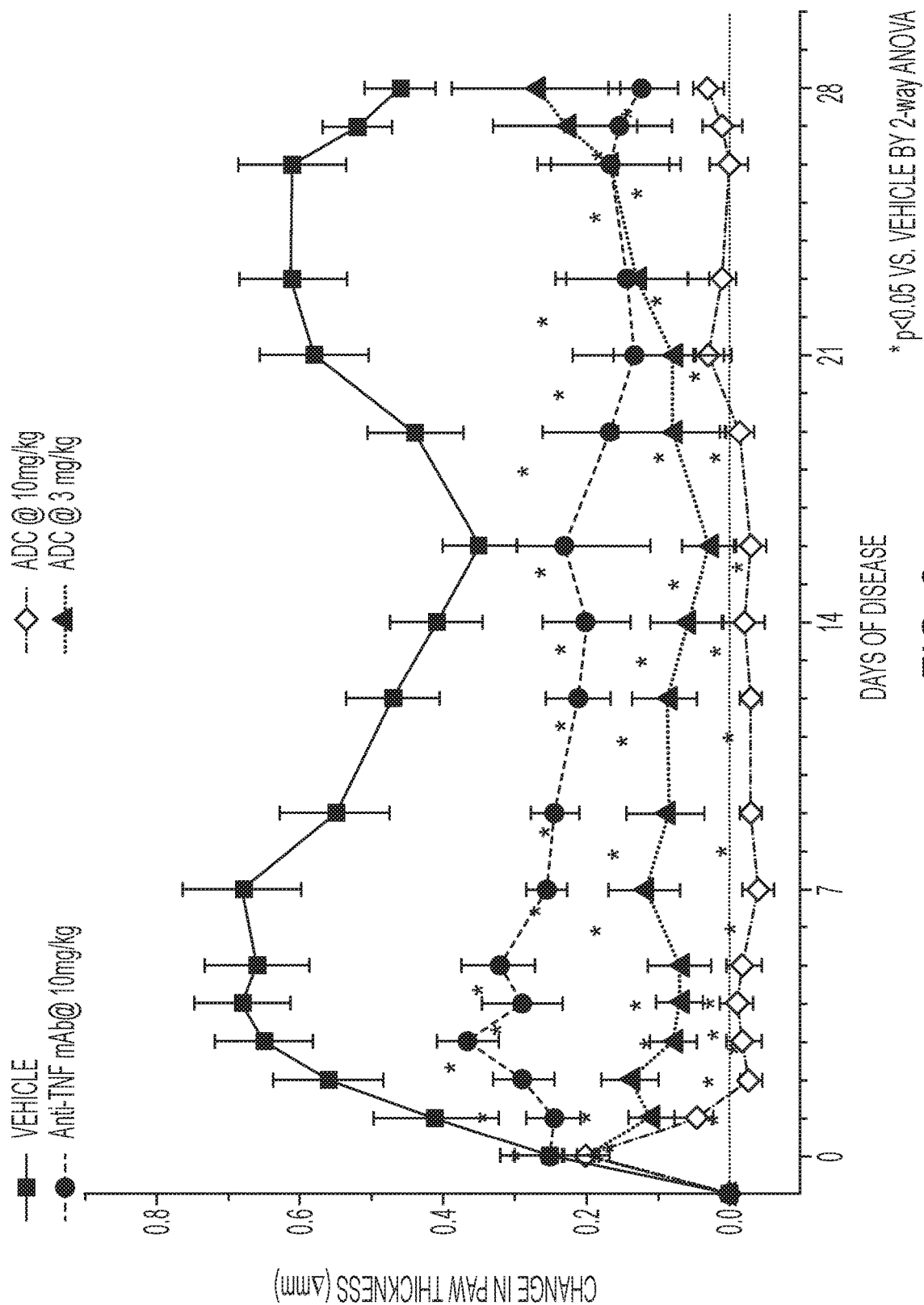
FIG. 3 provides a graph demonstrating the efficacy of a high and low dose of ADC1 compared to anti-TNFα mAb (high dose) or vehicle in a mouse collagen-induced arthritis (CIA) model of arthritis, as performed and described in Example 7. As shown, a single dose of anti-TNFα glucocorticosteroid ADC1 exhibited an extended duration of action through amelioration of paw swelling for ~28 days compared to anti-TNFα mAb or vehicles alone.

The results are shown in FIG. 3 and demonstrate that a single dose of anti-TNFα steroid ADC can exhibit an extended duration of action through amelioration of paw swelling for ~28 days compared to anti-TNFα mAb or vehicle alone.

ADC Stability in Plasma

Although hydrolysis has been employed to increase in vivo stability of maleimide-based linkers, it generally requires exposure to basic pH, which may lead to modifications in the antibody (e.g., deamidation), increased heterogeneity, decreased yield and the like. (Shen et al., *Nature Biotechnology* 30:184-189 (2012) (hydrolyzing maleimides avoids premature release of the drug and systemic exposure to the drug); Strop et al., *Chemistry & Biology* 20(2):161-167 (2013) (a similar study); Tumey et al., *Bioconjugate Chem* 25(10):1871-1880 (2014) (use of a proximal PEG chain to enable ring hydrolysis under basic conditions); Lyon et al., *Nature Biotechnology* 32:1059-1062 (2014) (processes for facilitating the creation of hydrolyzed succinimide); Christie et al., *J Control Release* 220(PtB):660-70 (28 Dec 2015) (use of N-aryl maleimides to facilitate succinimide ring hydrolysis under basic conditions); Dovgan et al., *Scientific Reports* 6:1 (2016)(use of 2-(maleimidomethyl)-1,3-dioxane for facilitating ring hydrolysis under mildly basic conditions for a prolonged period of time); and J Pharm Sci 2013: 102 (6) 1712-1723 (asparagine deamidation dependence on buffer type, pH and temperature). In contrast, typical conditions for conjugation using bromo acetamide are complete within a few hours, compared to multiple days for maleimide (conjugation and subsequent ring hydrolysis at basic pH). In addition, the 2-mercaptoacetamide formed during reaction of cysteine with the bromo acetamide is not susceptible to the reverse Michael reaction and affords a stable attachment of the linker to the antibody as demonstrated in Table 13 below for ADC4.

TABLE 13

| % SM released from ADC in plasma after 4 d @ 37° C. | | | | |
|---|---|---|---|---|
| PBS1X buffer | Mouse | Rat | Cyno | Human |
| BLQ | BLQ | BLQ | BLQ | BLQ |

BLQ—Below level of quantification (<1.0 nM)

ADC Stability in Solution

To assess long-term stability, a biologic is subjected to an accelerated stress test. The protocol for this test is 100 mg/mL of the biologic in 15 mM histidine at 40° C. for 21 days. When ADC4 was subjected to this test the percent increase in aggregate was <5% compared to ADC203 of US Patent Application Publication no. 2018/012600, published May 10, 2018, which saw an increase in aggregation of 18% (Table 14). This demonstrates the improved properties imparted to ADC4 by the Gly-Glu linker with the phosphate prodrug of the payload. ADC203 of US2018/0126000 is:

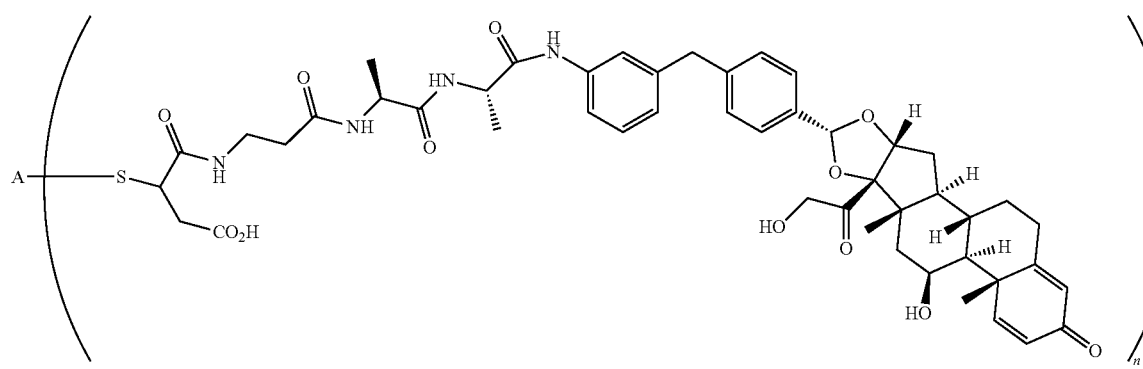

203 where n=4 and A refers to the anti-human TNFα antibody adalimumab.

TABLE 14

| ADC | Monomer Loss at 5° C. for 21 Days | Monomer Loss at 25° C. for 21 Days | Monomer Loss at 40° C. for 21 Days |
|---|---|---|---|
| ADC203 | 1.43% | 2.26% | 17.56% |
| ADC4 | <0.5% | <0.5% | 3.46% |

An additional benefit of the phosphate prodrug is it enables the use of anion exchange chromatography for the DAR purification. This results in improved peak resolution compared to hydrophobic interaction chromatography resulting in higher yields of DAR purified ADC.

Figure 4:
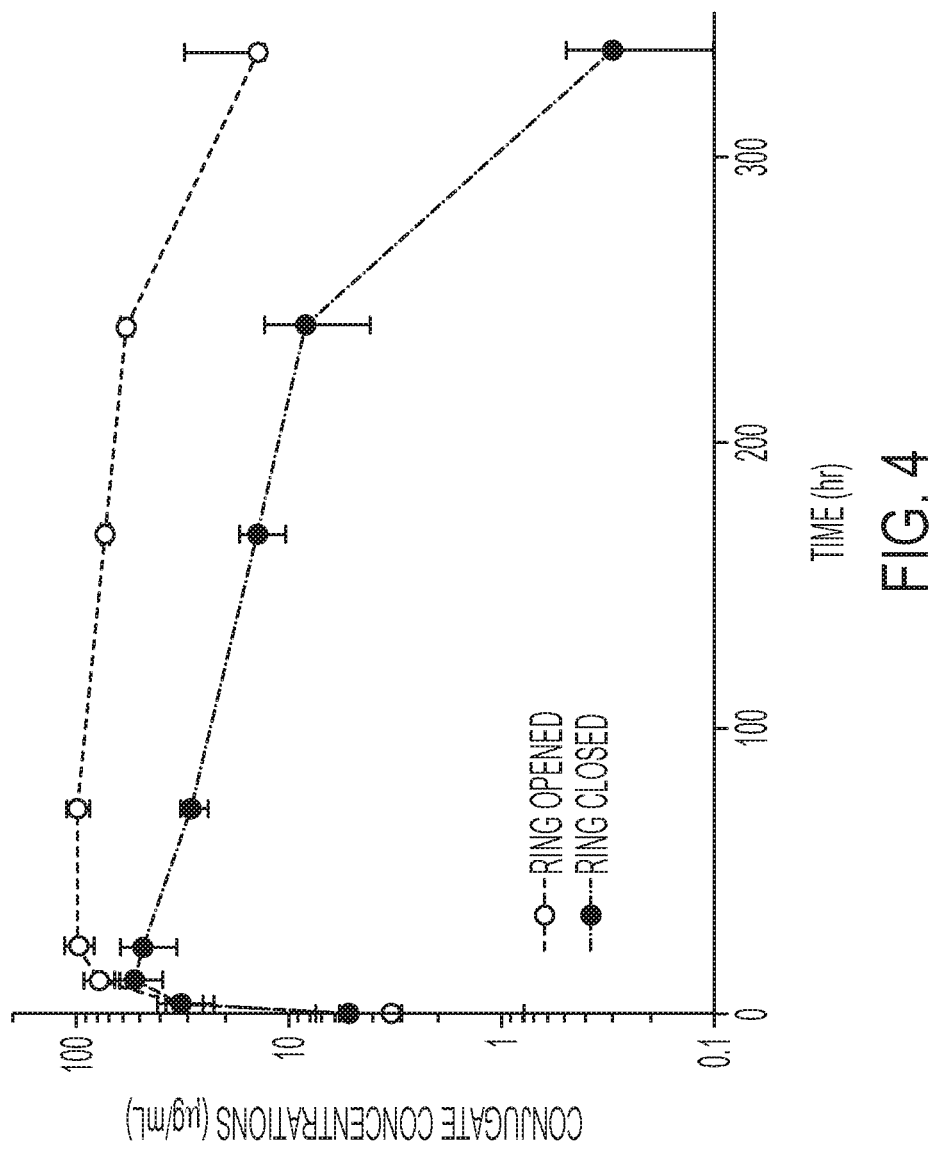
FIG. 4 is a graph of concentration (ug/ml) for closed and open ring ADC in cynomolgus monkeys over time, as performed and described in Example 7. As shown, the ring closed form is susceptible to the reverse Michael reaction and subsequent loss of linker-drug in vivo.

In formulation buffer the hydrolyzed succinimide ring of ADC203 is in equilibrium with the ring closed form. The ring closed form is susceptible to the reverse Michael reaction and subsequent loss of linker-drug in vivo in cynomolgus monkeys (FIG. 4).

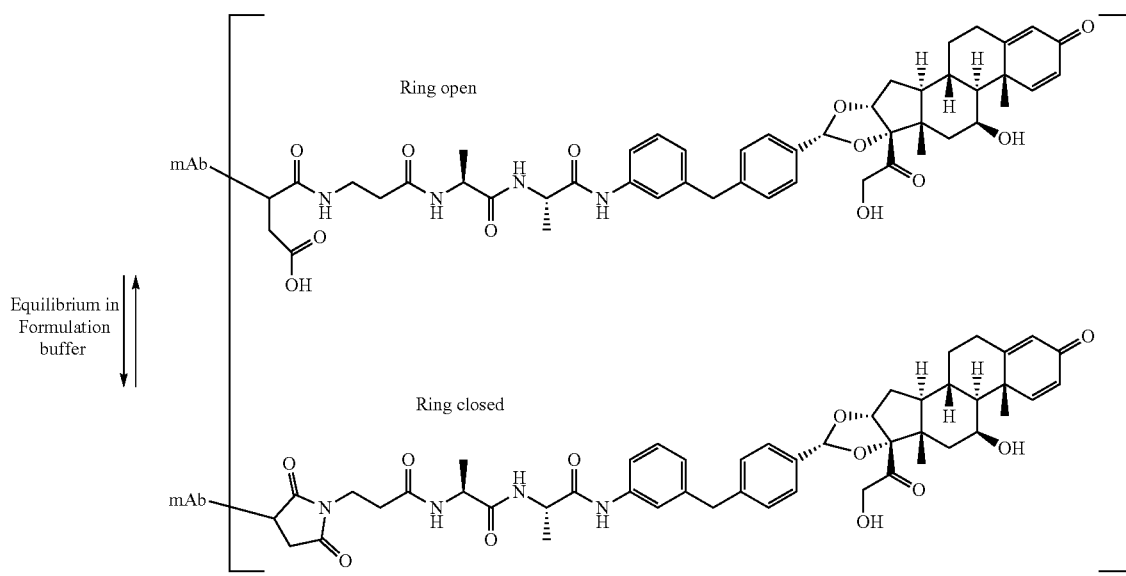

Under nominal liquid storage conditions the succinimide attachment in the open conformation will reform the closed conformation greater than 5% at 5° C. and greater than 15% at 25° C. after 6 months (Table 15).

TABLE 15

| | % Closed Succinimide Ring | |
|---|---|---|
| Time/Temp | Light Chain | Heavy Chain |
| 3 Months/5° C. | 2.2 | 4.6 |
| 6 Months/5° C. | 3.2 | 6.9 |
| 3 Months/25° C. | 10.1 | 13.3 |
| 6 Months/25° C. | 16.6 | 24.1 |
| 3 Months/40° C. | 26.2 | 33.7 |
| 3 Months/40° C. | 26.8 | 39.0 |

It is to be appreciated that the Detailed Description section, and not the Summary and Abstract sections, is intended to be used to interpret the claims. The Summary and Abstract sections sets forth one or more, but not all, exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

INCORPORATION BY REFERENCE

All publications, including patents and published applications, referred to in the Detailed Description are incorporated by reference herein in their entirety.

What is claimed is:

1. An antibody drug conjugate comprising:
   (a) an anti-TNFα antibody comprising a heavy chain set forth as SEQ ID NO: 3 and a light chain set forth as SEQ ID NO: 4; and
   (b) a glucocorticoid receptor agonist comprising a radical represented by the formula:

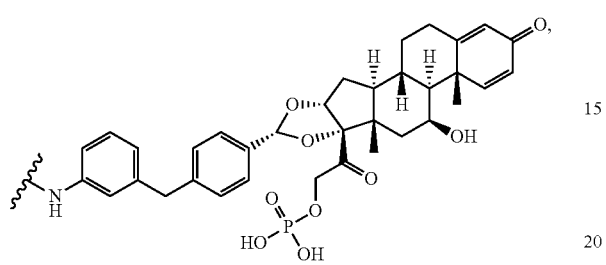

wherein the antibody is conjugated to the glucocorticoid receptor agonist via a linker represented by the formula:

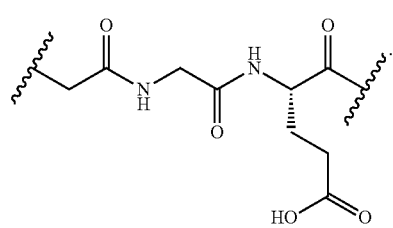 [SMILES: *CC(=O)NCC(=O)N[C@@H](CCC(=O)O)C(*)=O]

2. The antibody drug conjugate of claim 1, according to the formula:

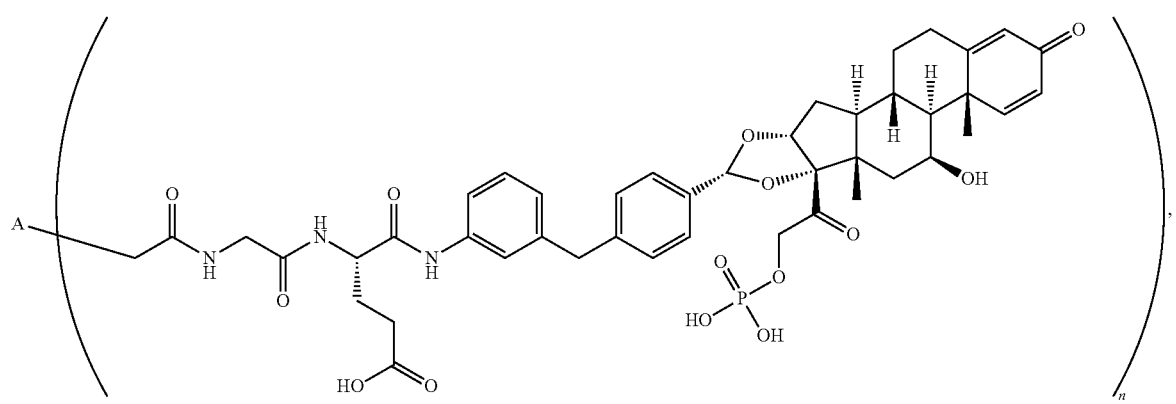

wherein A is the antibody and n is an integer from 1-10.

3. The antibody drug conjugate of claim 2, wherein n is 4.
4. The antibody drug conjugate of claim 2, wherein n is 2.
5. An antibody drug conjugate according to the formula:
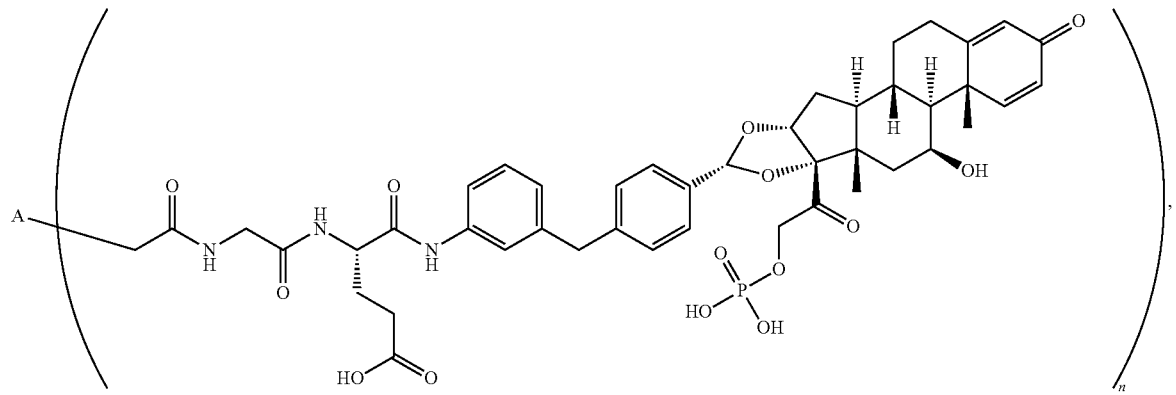
wherein A is adalimumab and n is 4.
6. An antibody drug conjugate according to the formula:
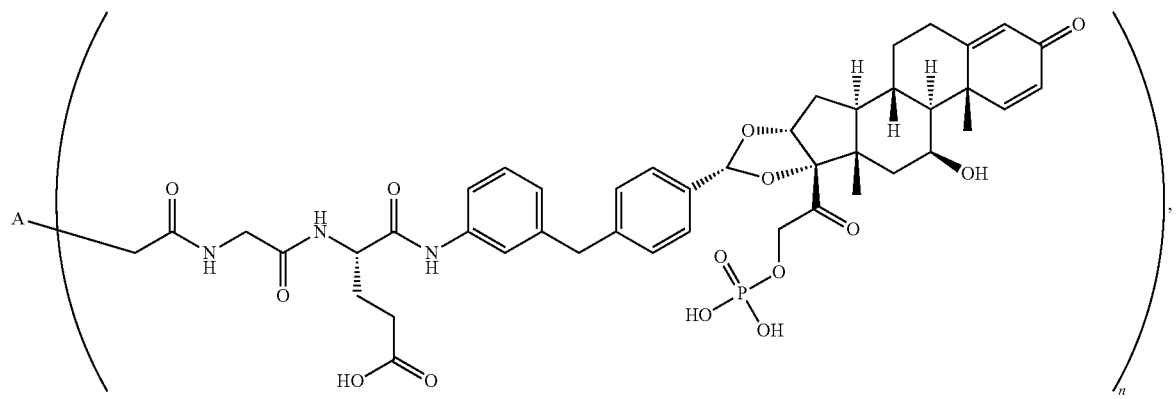
wherein A is adalimumab and n is 2.
* * * * *

```
SEQUENCE LISTING

<160> NUMBER OF SEQ ID NOS: 14

<210> SEQ ID NO 1
<211> LENGTH: 233
<212> TYPE: PRT
<213> ORGANISM: Homo sapiens

<400> SEQUENCE: 1

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
        130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
        210                 215                 220

Gln Val Tyr Phe Gly Ile Ile Ala Leu
225                 230

<210> SEQ ID NO 2
<211> LENGTH: 235
<212> TYPE: PRT
<213> ORGANISM: Mus sp.
```

<400> SEQUENCE: 2

```
Met Ser Thr Glu Ser Met Ile Arg Asp Val Glu Leu Ala Glu Ala
1               5                   10                  15

Leu Pro Gln Lys Met Gly Gly Phe Gln Asn Ser Arg Arg Cys Leu Cys
                20                  25                  30

Leu Ser Leu Phe Ser Phe Leu Leu Val Ala Gly Ala Thr Thr Leu Phe
            35                  40                  45

Cys Leu Leu Asn Phe Gly Val Ile Gly Pro Gln Arg Asp Glu Lys Phe
        50                  55                  60

Pro Asn Gly Leu Pro Leu Ile Ser Ser Met Ala Gln Thr Leu Thr Leu
65                  70                  75                  80

Arg Ser Ser Ser Gln Asn Ser Ser Asp Lys Pro Val Ala His Val Val
                85                  90                  95

Ala Asn His Gln Val Glu Gln Leu Glu Trp Leu Ser Gln Arg Ala
            100                 105                 110

Asn Ala Leu Leu Ala Asn Gly Met Asp Leu Lys Asp Asn Gln Leu Val
        115                 120                 125

Val Pro Ala Asp Gly Leu Tyr Leu Val Tyr Ser Gln Val Leu Phe Lys
130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
                165                 170                 175

Ser Pro Cys Pro Lys Asp Thr Pro Glu Gly Ala Glu Leu Lys Pro Trp
            180                 185                 190

Tyr Glu Pro Ile Tyr Leu Gly Gly Val Phe Gln Leu Glu Lys Gly Asp
        195                 200                 205

Gln Leu Ser Ala Glu Val Asn Leu Pro Lys Tyr Leu Asp Phe Ala Glu
    210                 215                 220

Ser Gly Gln Val Tyr Phe Gly Val Ile Ala Leu
225                 230                 235
```

<210> SEQ ID NO 3
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
```

```
            100                 105                 110
Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 4
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65              70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
50                  55                  60

Glu Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120
```

```
<210> SEQ ID NO 6
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 7
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Asp Tyr Ala Met His
1               5

<210> SEQ ID NO 8
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Phe Thr Phe Asp Asp Tyr Ala Met His
1               5                   10

<210> SEQ ID NO 9
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ala Ile Thr Trp Asn Ser Gly His Ile Asp Tyr Ala Asp Ser Val Glu
1               5                   10                  15

Gly
```

```
<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Val Ser Tyr Leu Ser Thr Ala Ser Ser
1               5

<210> SEQ ID NO 11
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Val Ser Tyr Leu Ser Thr Ala Ser Ser Leu Asp Tyr
1               5                   10

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Arg Ala Ser Gln Gly Ile Arg Asn Tyr Leu Ala
1               5                   10

<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ala Ala Ser Thr Leu Gln Ser
1               5

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gln Arg Tyr Asn Arg Ala Pro Tyr Thr
1               5
```